United States Patent
Vayser et al.

(10) Patent No.: US 9,718,130 B1
(45) Date of Patent: Aug. 1, 2017

(54) ILLUMINATED AND MODULAR SOFT TISSUE RETRACTOR

(71) Applicant: Invuity, Inc., San Francisco, CA (US)

(72) Inventors: Alex Vayser, Mission Viejo, CA (US); Douglas Rimer, Los Altos Hills, CA (US); Stephen DeSantis, Laguna Niguel, CA (US)

(73) Assignee: Invuity, Inc., San Francisco, CA (US)

( * ) Notice: Subject to any disclaimer, the term of this patent is extended or adjusted under 35 U.S.C. 154(b) by 0 days.

(21) Appl. No.: 15/598,120

(22) Filed: May 17, 2017

Related U.S. Application Data

(60) Continuation of application No. 15/439,527, filed on Feb. 22, 2017, which is a continuation of application
(Continued)

(51) Int. Cl.
*A61B 17/02* (2006.01)
*B22F 5/04* (2006.01)
(Continued)

(52) U.S. Cl.
CPC ............... *B22F 5/04* (2013.01); *A61B 1/06* (2013.01); *B22D 25/02* (2013.01); *B22D 29/002* (2013.01); *B22F 3/1055* (2013.01); *B22F 7/062* (2013.01); *B22F 7/08* (2013.01); *B33Y 10/00* (2014.12); *B33Y 80/00* (2014.12); *F01D 5/12* (2013.01); *A61B 17/0218* (2013.01); *B22F 2007/068* (2013.01); *F05D 2230/21* (2013.01);
(Continued)

(58) Field of Classification Search
CPC ...... A61B 1/06; A61B 17/0218; A61B 3/0016
See application file for complete search history.

(56) References Cited

U.S. PATENT DOCUMENTS 2,646,037 A   7/1953   Cook et al.
3,532,088 A   10/1970  John
(Continued)

FOREIGN PATENT DOCUMENTS

EP   0101781 A1   3/1984
GB   2078526 A    1/1982
(Continued)

OTHER PUBLICATIONS

Co-pending U.S. Appl. No. 15/439,527, filed Feb. 22, 2017.
(Continued)

*Primary Examiner* — Karabi Guharay
(74) *Attorney, Agent, or Firm* — Wilson Sonsini Goodrich & Rosati

(57) ABSTRACT

A surgical retractor for illuminating a surgical field includes an ergonomic handle, a retractor blade coupled with the handle, a quick release mechanism, and an illuminator blade. The retractor blade is adapted to engage and retract tissue, and the quick release mechanism is adapted to couple the handle with the retractor blade. The illuminator blade acts as a waveguide to transmit light by total internal reflection. Light is extracted from the illuminator to illuminate the surgical field. The retractor blade is releasable from the handle without requiring uncoupling of the illuminator blade from the handle and also without requiring optical uncoupling of the illuminator blade from a light source. The retractor may also be adapted to evacuate smoke from the surgical field.

11 Claims, 52 Drawing Sheets

Related U.S. Application Data

No. 14/872,482, filed on Oct. 1, 2015, now Pat. No. 9,610,130, which is a continuation of application No. 14/500,605, filed on Sep. 29, 2014, now Pat. No. 9,173,648, which is a division of application No. 13/624,622, filed on Sep. 21, 2012, now Pat. No. 8,876,709.

(60) Provisional application No. 61/538,675, filed on Sep. 23, 2011.

(51) Int. Cl.
  *B22F 3/105* (2006.01)
  *B22F 7/08* (2006.01)
  *B22F 7/06* (2006.01)
  *B22D 29/00* (2006.01)
  *B22D 25/02* (2006.01)
  *B33Y 80/00* (2015.01)
  *F01D 5/12* (2006.01)
  *B33Y 10/00* (2015.01)
  *A61B 1/06* (2006.01)

(52) U.S. Cl.
  CPC .... *F05D 2230/31* (2013.01); *F05D 2300/175* (2013.01); *F05D 2300/607* (2013.01)

(56) References Cited

U.S. PATENT DOCUMENTS

| | | | |
|---|---|---|---|
| 3,638,644 A | 2/1972 | Reick | |
| 3,641,332 A | 2/1972 | Reick et al. | |
| 3,766,910 A | 10/1973 | Lake | |
| 3,890,960 A | 6/1975 | Wunsch et al. | |
| 4,226,228 A | 10/1980 | Shin et al. | |
| 4,300,541 A | 11/1981 | Burgin | |
| 4,344,419 A | 8/1982 | Burgin | |
| 4,562,832 A | 1/1986 | Wilder et al. | |
| 4,574,784 A | 3/1986 | Soloway | |
| 4,592,344 A | 6/1986 | Scheer | |
| 4,597,030 A | 6/1986 | Brody et al. | |
| 4,605,990 A | 8/1986 | Wilder et al. | |
| 4,643,172 A | 2/1987 | Taff et al. | |
| 4,697,578 A | 10/1987 | Burgin | |
| 4,807,599 A | 2/1989 | Robinson et al. | |
| 4,842,356 A | 6/1989 | Mori | |
| 4,947,829 A | 8/1990 | Bullard | |
| 4,961,617 A | 10/1990 | Shahidi et al. | |
| 5,035,232 A | 7/1991 | Lutze et al. | |
| 5,353,786 A | 10/1994 | Wilk | |
| 5,873,818 A | 2/1999 | Rothfels | |
| 6,042,540 A | 3/2000 | Johnston et al. | |
| 6,080,105 A | 6/2000 | Spears | |
| 6,174,281 B1 | 1/2001 | Abramowitz | |
| 6,185,356 B1 | 2/2001 | Parker et al. | |
| 6,241,658 B1 | 6/2001 | Goodrich | |
| 6,280,379 B1 | 8/2001 | Resnick | |
| 6,322,499 B1 | 11/2001 | Evans et al. | |
| 6,504,985 B2 | 1/2003 | Parker et al. | |
| 6,554,768 B1 | 4/2003 | Leonard | |
| 6,817,978 B2 | 11/2004 | Holland et al. | |
| 7,261,689 B2 | 8/2007 | Holland et al. | |
| 7,306,559 B2 | 12/2007 | Williams | |
| 7,311,663 B2 | 12/2007 | Marcotte | |
| 7,766,825 B2 | 8/2010 | Hamel | |
| 7,850,608 B2 | 12/2010 | Hamada | |
| 7,935,053 B2 | 5/2011 | Karpowicz et al. | |
| 7,946,982 B2 | 5/2011 | Hamada | |
| 7,988,625 B2 | 8/2011 | Abdelgany et al. | |
| 8,876,709 B2 | 11/2014 | Vayser et al. | |
| 9,011,323 B2 | 4/2015 | Vayser et al. | |
| 9,173,648 B2 | 11/2015 | Vayser et al. | |
| 9,610,130 B2 | 4/2017 | Vayser et al. | |
| 2005/0119530 A1 | 6/2005 | Douglas et al. | |
| 2005/0240081 A1 | 10/2005 | Eliachar | |
| 2007/0055110 A1 | 3/2007 | Bass | |
| 2007/0208226 A1 | 9/2007 | Grey et al. | |
| 2007/0293729 A1 | 12/2007 | Grey et al. | |
| 2008/0200758 A1 | 8/2008 | Orbay et al. | |
| 2009/0112068 A1 | 4/2009 | Grey et al. | |
| 2009/0216088 A1 | 8/2009 | Danna et al. | |
| 2009/0227845 A1 | 9/2009 | Lo et al. | |
| 2009/0312610 A1 | 12/2009 | Buchok et al. | |
| 2010/0041955 A1 | 2/2010 | Grey et al. | |
| 2010/0113885 A1 | 5/2010 | McBride et al. | |
| 2010/0249528 A1 | 9/2010 | Vayser et al. | |
| 2010/0256454 A1 | 10/2010 | Farley et al. | |
| 2011/0106122 A1 | 5/2011 | Cetola | |
| 2011/0144440 A1 | 6/2011 | Cropper et al. | |
| 2012/0116170 A1 | 5/2012 | Vayser et al. | |
| 2013/0267786 A1 | 10/2013 | Vayser et al. | |

FOREIGN PATENT DOCUMENTS

| | | |
|---|---|---|
| GB | 2133694 A | 8/1984 |
| GB | 2406793 A | 4/2005 |
| WO | WO-015274 A1 | 7/2001 |
| WO | WO-0195810 A2 | 12/2001 |
| WO | WO-0195810 A3 | 6/2002 |
| WO | WO-2004077922 A2 | 9/2004 |
| WO | WO-2005016131 A2 | 2/2005 |
| WO | WO-2004077922 A3 | 3/2005 |
| WO | WO-2005016131 A3 | 12/2005 |
| WO | WO-2007084641 A2 | 7/2007 |
| WO | WO-2009055713 A1 | 4/2009 |
| WO | WO-2011087462 A1 | 7/2011 |

OTHER PUBLICATIONS

"European search report dated May 18, 2015 for EP Application No. 12833542.9."

European search report (Extended) dated Feb. 5, 2016 for EP Application No. 12833542.9.

International search report and written opinion dated Nov. 30, 2012 for PCT/US2012/056734.

Notice of allowance dated Jun. 27, 2014 for U.S. Appl. No. 13/624,622.

Notice of allowance dated Jul. 1, 2015 for U.S. Appl. No. 14/500,605.

Notice of allowance dated Nov. 23, 2016 for U.S. Appl. No. 14/872,482.

Office action dated Feb. 3, 2014 for U.S. Appl. No. 13/624,622.

Office action dated Mar. 22, 2016 for U.S. Appl. No. 14/872,482.

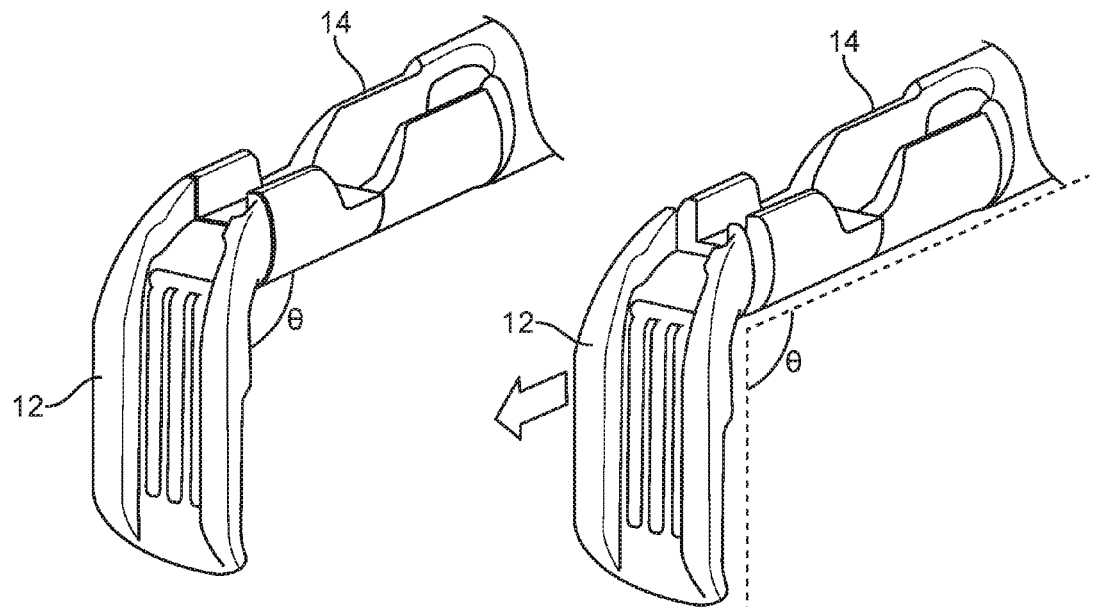
FIG. 6A
FIG. 6B
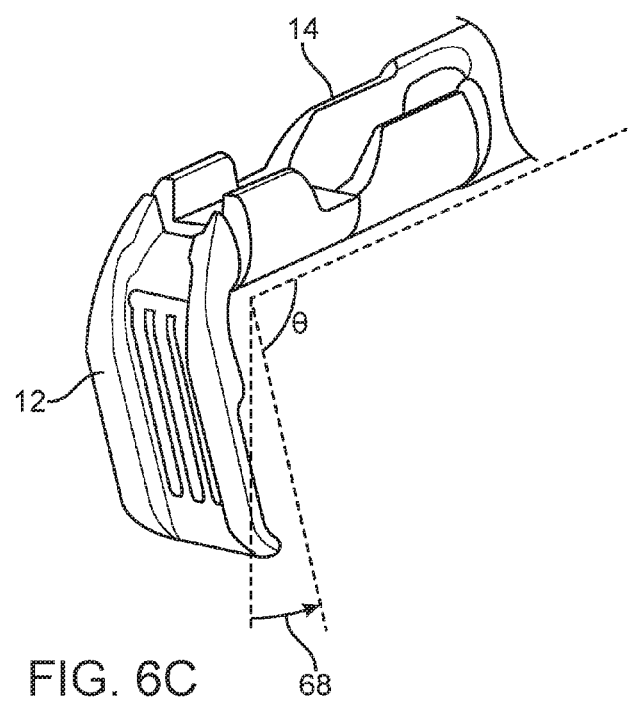
FIG. 6C

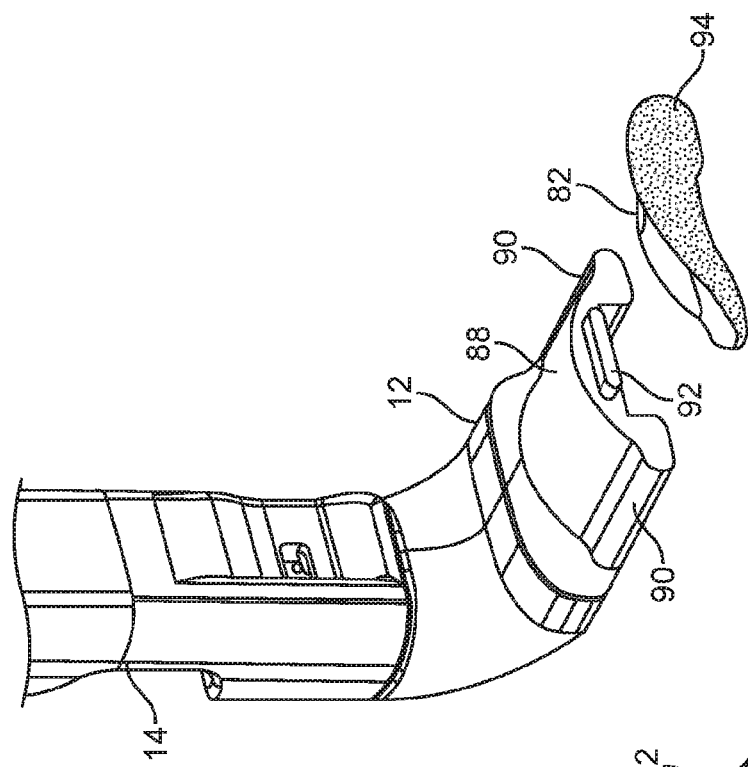
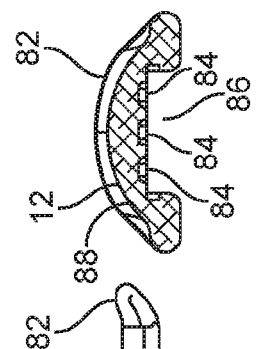
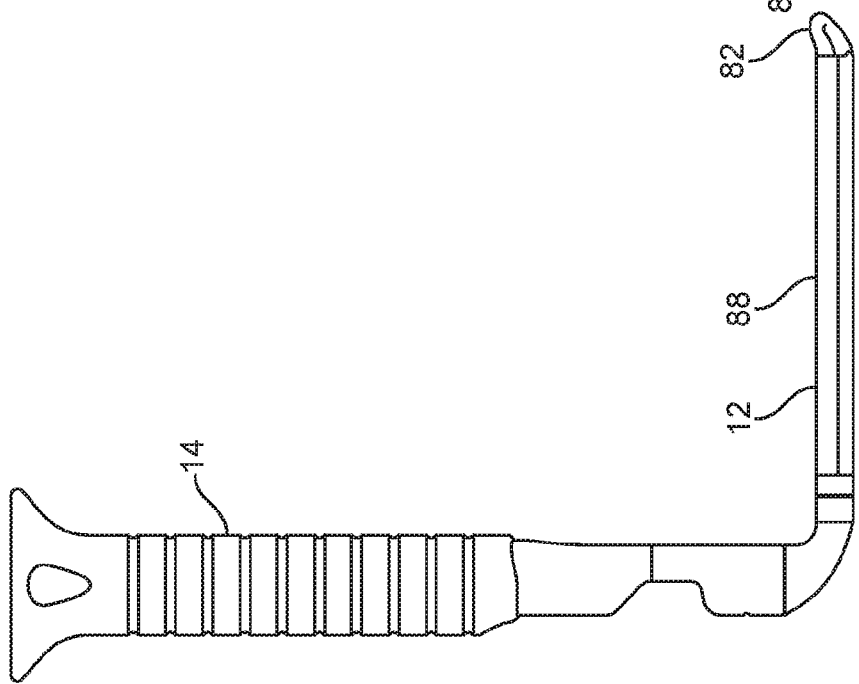
FIG. 9
FIG. 8B
FIG. 8A

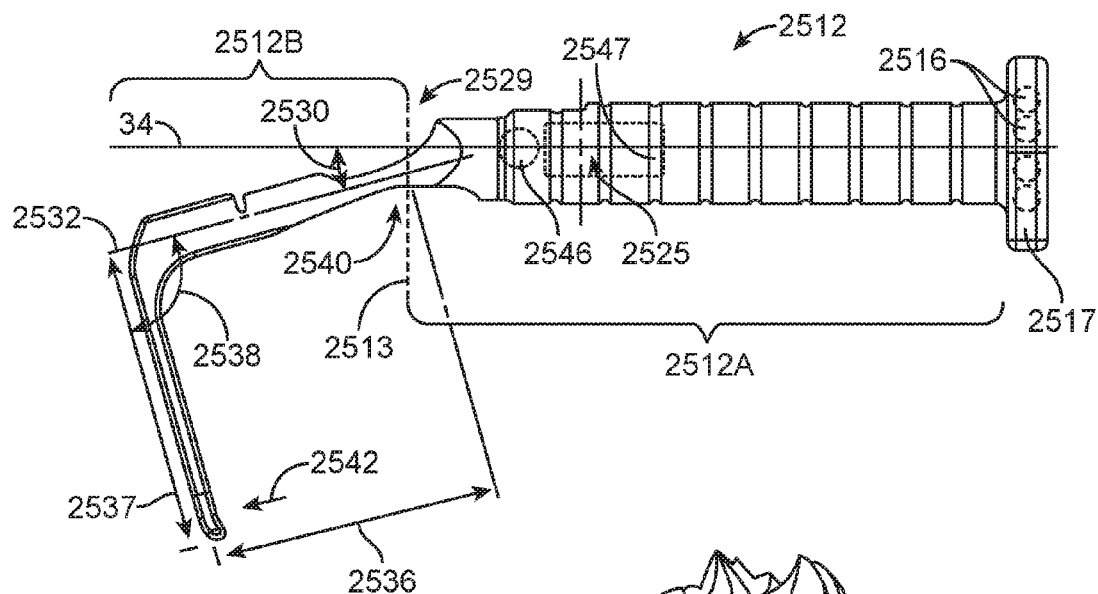
FIG. 28
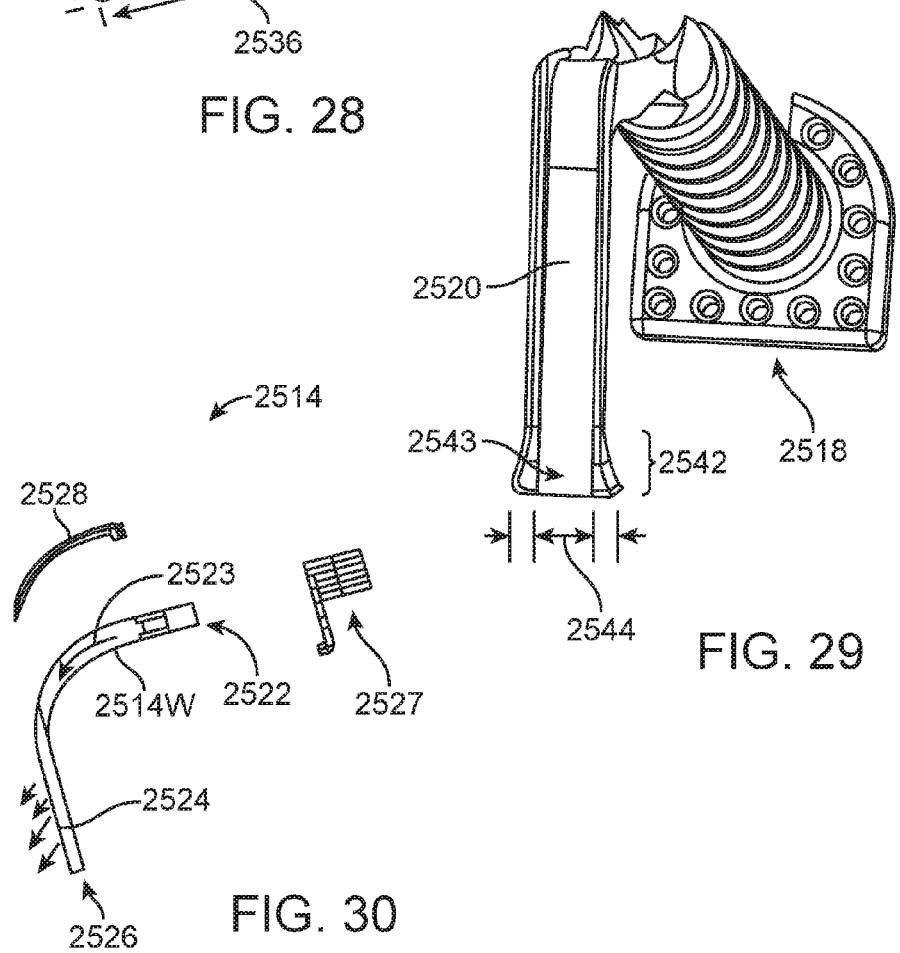
FIG. 29
FIG. 30

ILLUMINATED AND MODULAR SOFT TISSUE RETRACTOR

CROSS-REFERENCE

The present application is a continuation of U.S. patent application Ser. No. 15/439,527 filed Feb. 22, 2017, which is a continuation of U.S. patent application Ser. No. 14/872,482 now U.S. Pat. No. 9,610,130 filed on Oct. 1, 2015, which is a continuation of U.S. patent application Ser. No. 14/500,605 now U.S. Pat. No. 9,173,648 filed on Sep. 29, 2014, which is a divisional of, and claims the benefit of U.S. patent application Ser. No. 13/624,622 now U.S. Pat. No. 8,876,709 filed on Sep. 21, 2012, which is a non-provisional of, and claims the benefit of U.S. Provisional Patent Application No. 61/538,675 filed on Sep. 23, 2011; the entire contents of which are incorporated herein by reference.

This application is related to U.S. patent application Ser. Nos. 11/654,874; 11/432,898; 11/818,090; 12/750,581; 11/805,682; 11/923,483; 12/191,164; 13/026,910; and Ser. No. 13/253,785; the entire contents of each of which is incorporated herein by reference.

BACKGROUND OF THE INVENTION

Illumination of body cavities for diagnosis and or therapy is typically provided by overhead lighting or by headlamps. These forms of illumination can be challenging to use under certain situations. For example, overhead lighting must constantly be adjusted as the physician's position changes relative to the patient, as well as to illuminate different parts of the surgical field. Also, overhead lighting devices may require sterile handles to be attached to the lights in order for the physician to make adjustments without breaching the sterile field. Even then, the light provided by the overhead lamp may not illuminate the work space adequately. Head lamps can be heavy and uncomfortable to use, may require an assistant to help a physician put the headlamp on, and they often generate considerable amounts of heat during use which further limits comfort and can cause burns if an operator accidentally mishandles the head lamp. Head lamps also require the physician to constantly adjust head position in order to illuminate the work space, and this can be uncomfortable to the physician.

In an attempt to address some of these issues, surgical instruments such as retractors have been coupled with light pipes such as fiber optics to conduct light from a light source such as a halogen light or a LED light source in order to illuminate a surgical field. For example, some conventional illuminated soft tissue retractors utilize a fiber optic light bundle attached to a retractor handle. The fiber optic bundle provides a very focused light with a significant amount of heat. The fiber optics tube is also typically in the line of sight of the user, thereby obstructing a surgeon's view in use. Also, the fiber optic bundle only provides a narrow spot of light and must be constantly adjusted to illuminate the surgical field and minimize glare or shadows. Additionally, the fiber optic bundle requires precision manufacturing and polishing, and the fibers are fragile and can be easily scratched, occluded by blood or other debris, or otherwise damaged in use. Thus fiber optic bundles can also be challenging to use in illuminated surgical systems.

Other materials may be used as waveguides that overcome some of the challenges associated with fiber optic bundles. Exemplary materials such as acrylic or polycarbonate have also been used as waveguides, but these materials have unstable light transmission characteristics under extended use, and the transmission characteristics may change after sterilization using conventional techniques. For example, many polymers cross-link and turn yellow or become brittle after terminal sterilization with radiation. Heat from autoclaving or ethylene oxide sterilization can deform the waveguide. Additionally, precision optical polymers have limited mechanical properties which can limit their use in medical and surgical procedures. For example, some polymers are brittle and can easily shatter during use, or are difficult to process during manufacturing (e.g. hard to injection mold).

In addition to some of the challenges with illumination of a surgical field, surgical instruments such as retractor blades do not always accommodate the anatomy being treated, and the handles are not always ergonomically shaped for operator comfort in various positions. Conventional retractors also can interfere with electrosurgical devices and result in unwanted electrical arcing. Also smoke or other fumes created during electrosurgery can be toxic, and/or unpleasant and distracting for a physician. Current smoke evacuation devices can be cumbersome and obstruct visualization of the surgical process.

Therefore, it would be desirable to provide improved illuminated medical devices that provide better illumination of a work space and that reduce or eliminate some of the weight and heat constraints of traditional headlamps and overhead lighting. Such devices avoid interfering with electrosurgical devices and can evacuate smoke or noxious fumes generated by the electrosurgical device while maintaining a very low profile so as not to obscure visualization of the surgical procedure. Such devices preferably provide superior lighting to allow visualization of the surgical field, including adjacent tissues such as nerves or blood vessels. Additionally, it would also be desirable to provide improved illuminated medical instruments that are easy to manufacture (e.g. do not require optical polishing, can be injection molded), sterilizable, and have desired mechanical properties in service. It would also be desirable to provide illuminated medical devices that are ergonomically designed for operator comfort, and that can easily be adjusted or changed out with other attachments that accommodate various anatomies and operator positions. Such devices preferably include interchangeable handles and attachments such as retractor blades that can accommodate various waveguide illuminators. It would also be desirable to interchange handles and retractor blades with an easily actuated release mechanism that facilitates reliable interchangeability with minimal operator effort in slippery conditions which are typically encountered in surgery. Such instruments also have low profiles so the instrument can fit through small incisions or be positioned in small surgical fields which reduce scarring, improve healing time, and reduce hospital stay. At least some of these objectives will be addressed by the embodiments disclosed herein.

SUMMARY OF THE INVENTION

The present invention generally relates to medical devices and methods, and more particularly relates to illuminated medical devices and methods. These devices are preferably modular and can be interchanged with different handles and blades and may have other features such as the ability to evacuate smoke.

In a first embodiment, an illuminated and modular surgical retractor for illuminating a surgical field comprises a handle ergonomically designed to fit in a surgeon's hand, a retractor blade releasably coupled with the handle, a quick release mechanism coupled with the handle and retractor blade, and an illuminator blade releasably coupled with the handle and disposed adjacent the retractor blade. The retractor blade is adapted to engage tissue and retract the tissue in a retraction direction, and the quick release mechanism is adapted to couple the handle with the retractor blade. The illuminator blade has a light input portion, a light conducting portion, and a light output portion, and acts as a waveguide to transmit light from the light input portion through the light conducting portion to the light output portion by total internal reflection. Light is extracted from the light output portion to illuminate the surgical field. The retractor blade is releasable from the handle in a direction transverse to the retraction direction, and also without requiring uncoupling of the illuminator blade from the handle. The retractor blade is also releasable from the handle without requiring optical uncoupling of the illuminator blade from a light source. The light source may be an external light source such as a halogen light, or the light source may be an LED that may be coupled to or integrated into the handle. Rechargeable or disposable batteries may be disposed in the handle for energizing the light source. The light source may also be programmable to provide different lighting.

The handle may comprise a proximal end and a distal end, and the handle may further comprise a flared region adjacent the proximal end to facilitate handling by the surgeon. The handle may also comprise other ergonomic features such as scalloped regions adjacent the proximal end, a hub disposed adjacent the proximal end thereof that is releasably coupled to the handle, or a textured outer surface. The textured surface may comprise a plurality of finger grooves disposed circumferentially around the handle that are adapted to facilitate handling of the handle by a physician. The handle may comprise a substantially cylindrical body, and also may have a first channel extending between the proximal and distal ends thereof that are sized to receive a cable for optically coupling the light input portion of the illuminator blade with the light source. The handle may comprise a plurality of cable positioning apertures disposed adjacent the proximal end of the handle, and the apertures may be sized to slidably receive the cable for optically coupling the illuminator blade with the light source. The handle may also have a second channel that extends between the proximal and distal ends thereof, and that is sized to receive a suction tube that fluidly coupled the retractor blade with a source of vacuum. The cable positioning apertures may communicate with the first channel and dispose the cable laterally to a side of the handle. The retractor blade may also be pivotably coupled with the handle. The handle may also be modular such that different proximal, distal, or middle portions may be connected together to form a custom handle that ergonomically fits in an operator's hand, has the appropriate length or shape to fit the anatomy being treated, and has the appropriate mechanical and electrical elements for coupling with other retractor blades or illuminator blades.

The retractor blade may be formed from a metal such as stainless steel or aluminum, or it may be injection molded from a polymer or composite material. The blade may comprise a plurality of vacuum channels disposed therealong, and the handle may have a second channel extending between the proximal and distal ends thereof, sized to receive a suction tube for fluidly coupling the plurality of vacuum channels with a vacuum source. The retractor blade may comprise at least one vacuum channel disposed therein. The illuminator blade may be disposed in a channel in the retractor blade and may be sealingly engaged with the retractor blade to prevent vacuum leakage along seal. The retractor blade may comprise one or more channels therein for delivering a vacuum, and a cover may be disposed thereover in sealing engagement. The cover may be slidably engaged with the retractor blade or it may be fixedly coupled thereto. The retractor blade may have a constant cross-sectional geometry or it may change from proximal to distal ends. For example, the thickness may decrease distally, and the width may increase or decrease distally. The retractor blade may have a channel for receiving the illuminator blade and the channel depth may decrease until the channel disappears and becomes flush with the retractor blade surface on a distal portion of the retractor blade.

The illuminator blade may be an optical waveguide that transmits light therethrough via total internal reflection. The optical waveguide may be a non-fiber optic waveguide that may be injection molded and therefore is a single integral component fabricated from a single homogenous material such as polycarbonate, polymethyl methacrylate, cylco olefin polymer or cyclo olefin copolymer.

The retractor blade may comprise a distal tip that is releasably coupled to a distal portion of the retractor blade and that is adapted to engage and grasp tissue during retraction. The retractor blade may comprise an extension blade that is releasably coupled to a distal portion of the retractor blade. The distal tip may comprise a textured surface and may be curved upwards in the retraction direction. The distal tip may have a covering disposed thereover, and the covering may have a textured surface adapted to engage and grasp tissue during retraction. The retractor blade may comprise an alignment feature disposed on the retractor blade or on the handle, and this alignment feature is adapted to linearly align the retractor blade with the handle during engagement therebetween. The alignment feature may comprise a rail disposed on the retractor blade or the handle. The retractor blade may have a proximal region and a distal region, and the proximal region may be disposed in a first plane substantially parallel with the handle, and the second region in a second plane transverse to the first plane. A portion of the retractor blade may be electrically insulated.

The quick release mechanism may comprise an engagement element disposed on either the handle or the retractor blade, and the mechanism may also have a receptacle on the other of the handle or the retractor blade. The receptacle may be sized to receive the engagement element. The engagement element may be slidably received in the receptacle or it may be rotatably engageable with the receptacle. The engagement element may comprise a T-shaped bar rotationally engageable with the receptacle, or it may comprise an enlarged head, and the receptacle may have a flanged portion sized to receive the enlarged head. The quick release mechanism may comprise an actuator mechanism for sliding or otherwise moving the engagement element between engaged and disengaged positions. The engaged or disengaged positions may comprise a switch or lever or other actuation mechanism that is retracted or advanced into position. In the advanced position the engagement element may be coupled with the receptacle. The engagement element may be biased to return to the retracted position. The quick release mechanism may comprise a detent on either the handle or the retractor blade, and the mechanism may also comprise a receptacle for receiving the detent on the other of the handle or retractor blade. The quick release mechanism may further comprise a locking mechanism for locking the quick release mechanism to prevent disengagement of the retractor blade from the handle. The locking mechanism may have a rotatable cam having a first position and a second position. In the first position the rotatable cam prevents actuation of the quick release mechanism thereby preventing disengagement of the retractor blade from the handle, and in the second position, the rotatable cam allows actuation of the quick release mechanism thereby permitting disengagement of the retractor blade from the handle. The quick release mechanism may comprise a rotatable lever disposed on either the handle or the retractor blade, and the rotatable lever may have a first position and a second position. In the first position the lever prevents slidable movement between the retractor blade and the handle, and in the second position the lever permits slidable movement between the retractor blade and the handle. The surgical retractor may further comprise a suction tube that is fluidly coupled with the retractor blade, and the quick release mechanism may comprise an aperture disposed in the retractor blade for receiving the suction tube.

The retractor blade may comprise a channel extending from a proximal end thereof toward a distal end thereof, and the illuminator blade may be disposed in the channel. The illuminator blade may have active zones and dead zones. Light passes through the active zones by total internal reflection, and substantially no light passes through the dead zones by total internal reflection. The illuminator blade may have engagement elements in the dead zones that allow the illuminator blade to be disposed against the retractor blade while maintaining an air gap between active zones of the illuminator blade and the retractor blade. The light input portion of the blade illuminator may also comprise active zones and dead zones. Light passes through the active zones by total internal reflection, and substantially no light passes through the dead zones by total internal reflection. The light input portion may comprise a cylindrical proximal portion adapted to be coupled with a light source, and a rectangular distal portion optically coupled with the light conducting portion. A shield having a collar may be disposed over the cylindrical proximal portion such that an air gap is maintained therebetween. The shield may be disposed over the light conducting portion. The shield preferably protects the blade illuminator from damage caused by other surgical instruments in the surgical field and also preferably shields a physician from glare emitted from the blade illuminator. The shield may comprise a tab that is adapted to releasably couple the blade illuminator with the handle. The light output portion may comprise a plurality of surface features for extracting light from the blade illuminator and for directing the extracted light laterally and/or distally toward the surgical field. Some of the surface features may comprise parallel prism shapes with a primary facet and a secondary facet. The light input portion may comprise a generally cylindrical input zone transitioning to a generally rectangular neck. The blade illuminator may have a width and a thickness, and the width may be generally greater than the thickness. The light input portion may be disposed in a plane substantially parallel with the handle, and the light output portion may be in a plane transverse thereto. The surgical retractor may further comprise a light input cable optically and releasably coupled with the light input portion of the blade illuminator. The light input cable optically couples the blade illuminator with the light source.

The surgical retractor may further comprise a vacuum channel for extracting smoke from the surgical field. The vacuum channel may comprise a plurality of channels disposed in the retractor blade that are also fluidly coupled with a vacuum source. A first cover or vane which may be integrated into the waveguide may be disposed over the channels thereby forming a plenum therebetween for extracting the smoke while maintaining the minimal profile. A second cover or vane may be disposed over the channels. The first cover may be disposed end-to-end with the second cover, or it may be disposed on top of the second cover, or the two covers may have a joint connecting them together. The first cover or the second cover may be linearly slidable relative to the channels thereby adjusting vacuum strength. The first cover may comprise a plurality of apertures extending therethrough, and the second cover may be slidably disposed over the first cover such that vacuum strength may be adjusted by sliding the second cover relative to the first cover to adjust exposure of the apertures. The retractor blade may comprise an elongate channel, and the first cover and the second cover may be disposed in the channel. The first and second covers may be slidably disposed in a slot in the retractor blade. A vacuum hose may be disposed in the handle and it may be coupled with the retractor blade so that the vacuum hose fluidly couples the plurality of channels with the vacuum source. The vacuum hose may need to be uncoupled from the retractor blade prior to disengagement of the retractor blade from the handle. The surgical retractor may also have a pivot mechanism coupled with the handle. The pivot mechanism allows adjustment of an angle between the retractor blade and the handle.

In another aspect of the present invention, a surgical method for retracting soft tissue comprises providing a handle with an illuminator blade coupled thereto, selecting a retractor blade from a plurality of retractor blades, and releasably coupling the retractor blade with the handle. The method also includes the steps of positioning the retractor blade in a surgical field, illuminating the surgical field with light extracted from a light output portion of the illuminator blade, wherein light is transmitted from a proximal end of the illuminator blade to the light output portion by total internal reflection, retracting the soft tissue with the retractor blade in a retraction direction, and releasing the retractor blade from the handle in a direction transverse to the retraction direction. The retractor blade is released from the handle without requiring uncoupling of the illuminator blade from the handle, and the retractor blade is released from the handle without requiring optical decoupling of the illuminator blade from a light source.

Releasing the retractor blade may comprise actuating an actuator mechanism, releasing a detent mechanism, rotating a lever, or disengaging the retractor blade in a direction toward a distal end of the retractor blade. The cable may optically couple the light source with the blade illuminator, and releasing the retractor blade from the handle may not require decoupling of the cable from the blade illuminator. The retractor blade may also be released from the handle by rotating the retractor blade relative to the handle. A suction tube may be uncoupled from the retractor blade and retracted through the handle in order to release the retractor blade from the handle. Coupling the retractor blade with the handle may comprise sliding an enlarged head into a receptacle, and the enlarged head may be disposed on the retractor blade or the handle with the receptacle being disposed on the other of the retractor blade or the handle. The method may further comprise locking the retractor blade with the handle after coupling therebetween, or unlocking the retractor blade from the handle prior to release therebetween.

The method may also include releasably coupling a hub with a proximal portion of the handle. Other aspects of the method may include pivoting the retractor blade relative to the handle, and extracting smoke from the surgical field. The smoke may be evacuated from the surgical field by applying suction through a plurality of channels in the retractor blade.

Suction strength may be adjusted by moving a plate over the plurality of channels to control exposure thereof. The method may also comprise coupling or decoupling a distal retractor tip with the retractor blade. A cover may be applied to a distal portion of the retractor blade and the cover may have surface features that are adapted to grasp tissue. The cable may be positioned laterally to one side of the handle by positioning the cable in one of a plurality of cable positioning apertures disposed adjacent a proximal end of the handle.

These and other aspects and advantages of the invention are evident in the description which follows and in the accompanying drawings.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 6A-6C illustrate adjustment of the retractor blade relative to the handle.

FIG. 8A illustrates a side view of a surgical retractor.

FIG. 8B illustrates an end view of the surgical retractor in FIG. 8A.

FIG. 9 illustrates a perspective view of a retractor blade.

FIG. 28 is a side view of the illuminated soft tissue retractor of FIG. 25.

FIG. 29 is an end view of the illuminated soft tissue retractor of FIG. 25.

FIG. 30 is an exploded side view of the illumination waveguide assembly of FIG. 27.

DETAILED DESCRIPTION OF THE INVENTION

Modular Soft Tissue Retractor

Figure 1:
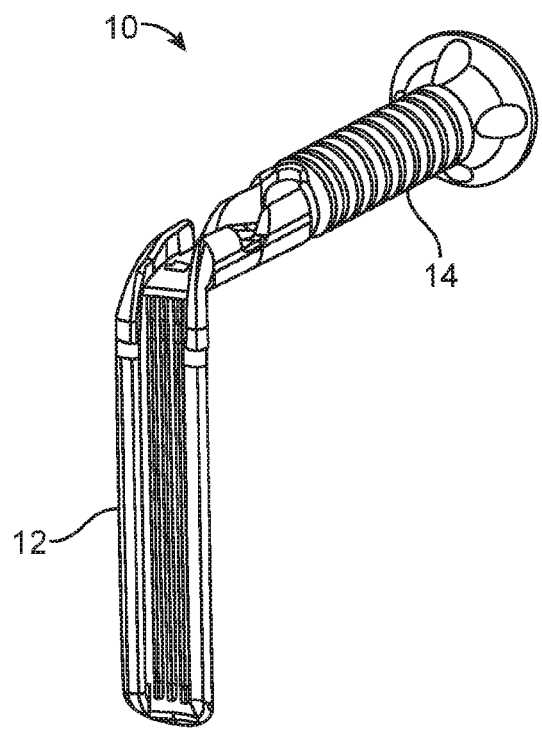
FIG. 1 illustrates a perspective view of a soft tissue retractor.

FIG. 1 illustrates a perspective view of a soft tissue retractor 10. The retractor 10 includes a handle 14 and a retractor blade 12 releasably coupled to the handle 14. The retractor may be used to retract any tissue, but is preferably used to retract tissue during breast surgery or thyroid surgery. Various retractor blades 12 may be coupled with the handle 14 in order to accommodate variety of situations including different tissues, anatomies, and physician position. The soft tissue retractor may also include lighting elements for illuminating the surgical field, a suction mechanism for evacuating smoke or other noxious fumes, as well as any of the other features discussed herein. Any of the components of the soft tissue retractor (e.g. retractor blade, handle, blade illumination device, etc.) may be single-use disposable, or they may be easily cleaned and re-sterilized for multiple use.

Handle

Figure 2:
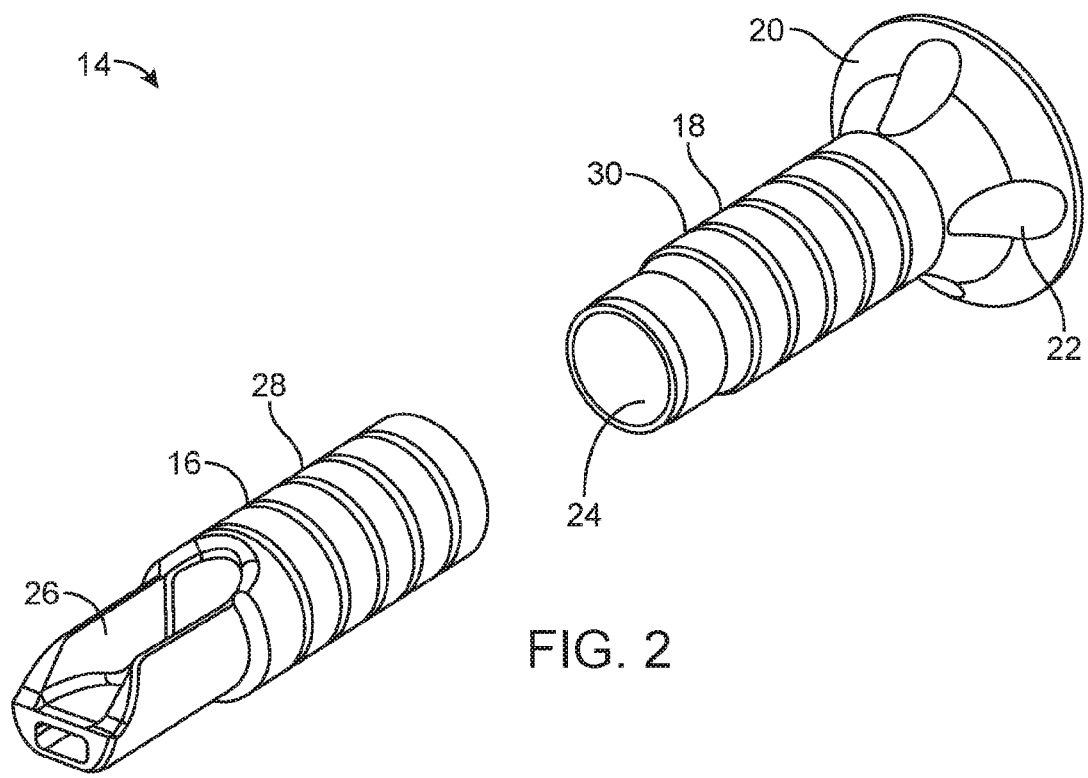
FIG. 2 illustrates a perspective view of a handle.

The handle 14 may be a single piece of unitary construction or it may have several modular sections that are fixedly joined together using techniques known to those of skill in the art such as by welding, using fasteners like screws, adhesively bonding, press-fitting, etc. In other embodiments, the handle includes modular sections which the physician or operator selects based on preference, and then the modular sections are releasably coupled together. For example, FIG. 2 illustrates an exemplary embodiment of a modular handle having a proximal hub section 18 and a distal section 28. Various hub and distal section geometries may be provided. In an exemplary embodiment, the proximal hub section 18 preferably includes a generally cylindrical body 30 sized to comfortably fit in an operator's hand, and having a flared proximal end 20 so that the handle may be firmly grasped when retracting in a proximal direction, thereby helping to prevent the handle from slipping out of the operator's hand. Other handle shapes are also contemplated including oval cross-sections, or flat surfaces. Scallops 22 on the proximal portion of the hub section 18 further help an operator grasp the handle. Finger grooves 16 may be disposed on an outer surface of either or both of the proximal hub section 18 and the distal section 28. In preferred embodiments, the finger grooves 16 are grooves circumferentially disposed around the handle. The handle may also have thumb grips. The handle may also have a central channel 24 extending either partially between the proximal and distal ends of the handle, or entirely therebetween. The central channel allows cables or other tubing to run through the central channel in order to prevent the cables or tubing from becoming damaged, tangled or otherwise interfering with the surgical procedure being performed. The central channel 24 may open up into an open channel 26 near the distal end of the handle to allow coupling with an illumination blade device as will be described below. The distal section 28 may also have a cylindrical body that is sized to fit in an operator's hand. In alternative embodiments, the hub section 18 and distal section 28 are manufactured separately and then fixedly coupled together. The handle may be fabricated out of metals such as stainless steel, cast, or it may be injection molded with a polymer. Some handles may be composite materials or may include ceramics. Handles may be re-sterilizable using ethylene oxide, gamma or e-beam irradiation, plasma, or autoclave sterilization. The handles may also be for single-use and disposable afterwards.

Figure 3:
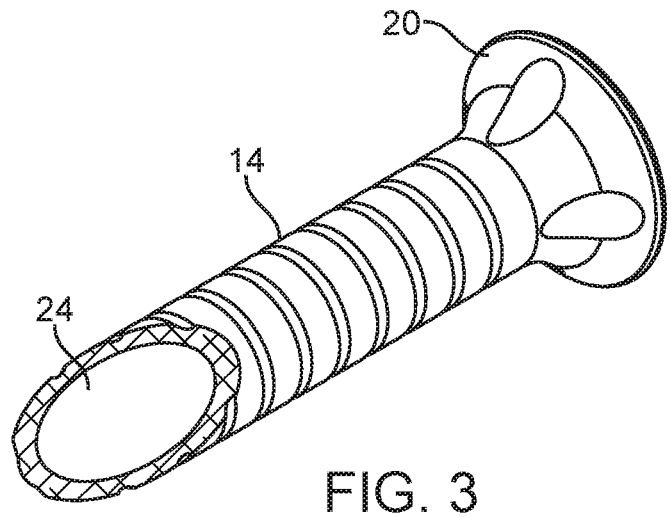
FIG. 3 illustrates a cross-section of a handle.
Figure 4A:
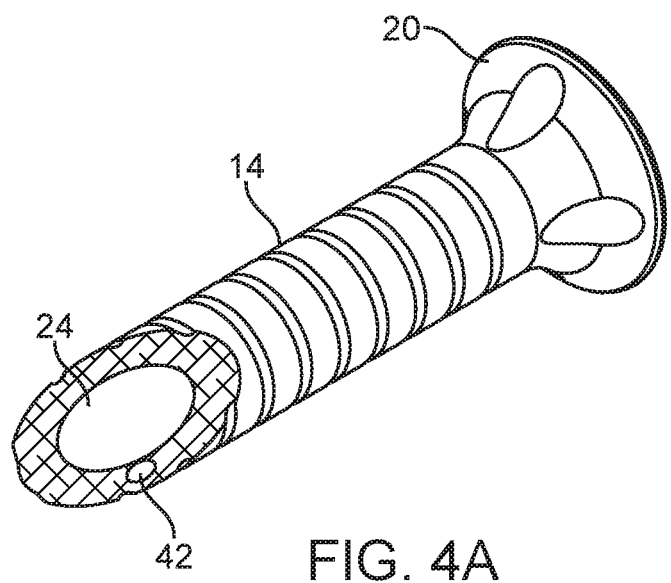
FIGS. 4A-4B illustrate alternative cross-sections of a handle.
Figure 4B:
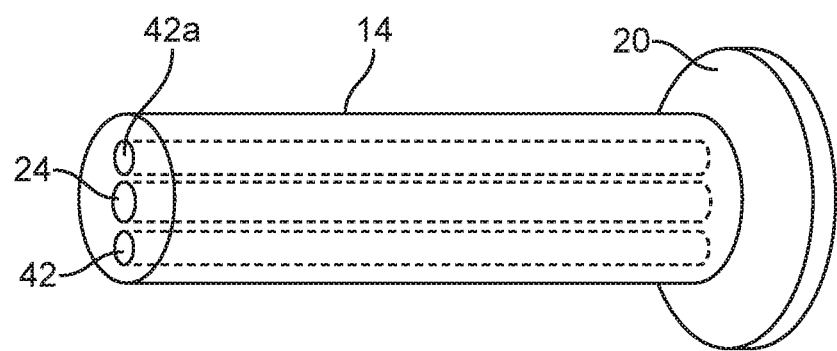

FIG. 3 illustrates a cross-section of handle 14 highlighting the central channel 24 extending therethrough. FIG. 4A illustrates a cross-section of an alternative embodiment of handle 14 having central channel 24 as well as a second channel 42 in a wall of the handle and extending through the handle from proximal to distal ends of the handle. The second channel 42 be used for other cables, tubes, wires, etc. that may be required in the surgical retractor. In preferred embodiments, the second channel 42 is used to hold a vacuum tube (also referred to herein as a suction tube or vacuum line) that can be coupled with the retractor blade to provide suction for evacuation of noxious fumes or smoke, especially during electrosurgery. One of skill in the art will appreciate that any of the handle features disclosed herein may be used in combination with one another. A fiber optic cable may also be disposed in the second channel in order to deliver light from a light source to the illumination blade device. Multiple channels in the wall are also contemplated for suction tubes, fiber optics, electrical wires, or any other cables that may be used such as in FIG. 4B where a fiber optic cable is disposed in channel 42a and a suction line is disposed in channel 42, both channels in a sidewall of the handle 14.

Figure 5:
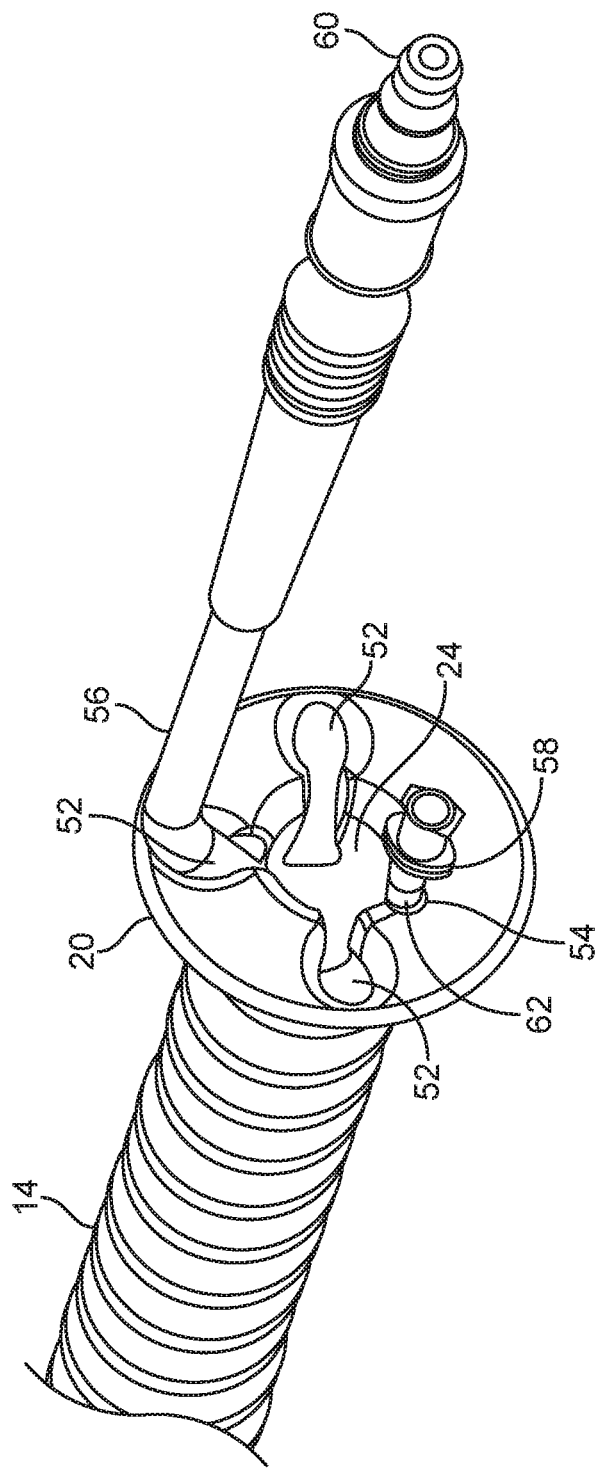
FIG. 5 illustrates a perspective view of the proximal end of a handle.

FIG. 5 illustrates the proximal end of exemplary handle 14. The proximal end includes a plurality of apertures 52 through which cables such as a light input cable 56 may be passed. Light input cable 56 includes a standard optical fitting 60 such as an ACMI coupling for connecting the cable with a light source. The apertures 52 are sized to accommodate various cables, and allow the cables to be press fit and held in position. This laterally displaces the cables to one side of the handle, thereby assisting with cable management and keeping the cables out of the way. The apertures 52 preferably are angled inward and communicate with the central channel 24, thus the cable can be slid into the central channel 24 to the distal end of the handle where it may be optically coupled to an illumination blade device. Similarly, smaller apertures 54 may also be disposed on the proximal end of the handle 14 in order to accommodate other tubing or cables, such as a suction tube 62. A connector 58 such as a Luer connector allows the suction tubing to be fluidly coupled with a vacuum source for smoke or fume evacuation. The suction tube may be advanced into the aperture 54 until the connector 58 is press fit into the aperture, thereby holding the tubing in position. The smaller apertures 54 may also angle inward and merge with the central channel 24, or they may remain a separate channel all the way through the handle, such as channel 42 seen in FIG. 4.

Additionally, the handle may be coupled with a strong arm or other rigid coupling that can hold the retractor in a desired position thereby freeing the surgeon's or assistant's hands. The strong arm may be attached to the operating table, a wall in the operating room, or may be on a separate cart or table. Typically the strong arm is also adjustable in order to hold the retractor in various positions. Weight may also be attached to the handle in order to hold the retractor in a desired position.

Retractor Blade Adjustment

FIG. 6A illustrates a typical retractor blade 12 coupled to a handle 14. The blade 12 forms an angle $\theta$ relative to the handle. In FIG. 6A, the retractor blade is substantially perpendicular relative to handle 14, thus $\theta=90°$. However, in certain circumstances, it is advantageous to adjust $\theta$ to a different angle. Thus, any of the retractors disclosed herein may have an adjustment mechanism that allows angle $\theta$ to be adjusted. This is commonly referred to as adjusting the toe-in or toe-out of the blade. FIG. 6B illustrates how the blade may be moved outward or distally 66 so that $\theta$ is an obtuse angle, while FIG. 6C illustrates actuation of the retractor blade 12 inward or proximally 68 so that $\theta$ is acute.

One of skill in the art will appreciate that any number of mechanisms may be used to allow adjustment of $\theta$. However, in a preferred embodiment of the surgical retractor, an illumination blade device is coupled with the handle and disposed over the retractor blade, a suction tube is coupled with the retractor blade for smoke evacuation, and an optical input cable is coupled with the illumination blade device. Thus, the pivoting mechanism that allows adjustment of toe-in or toe-out must accommodate the suction tube and optical cable, as well as maintaining the position of the illumination blade device relative to the retractor blade. Thus the adjustment mechanism allows the retractor blade to be pivoted without changing the relative position of the illumination blade and retractor blade. Also, the mechanism allows the movement without unnecessarily straining the suction tube and illumination cable.

Figure 7A:
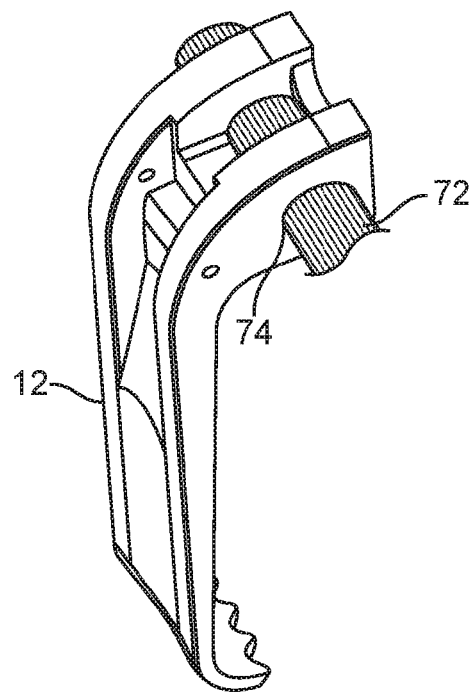
FIG. 7A is a perspective view of a retractor blade that allows adjustment of toe-in and toe-out.
Figure 7B:
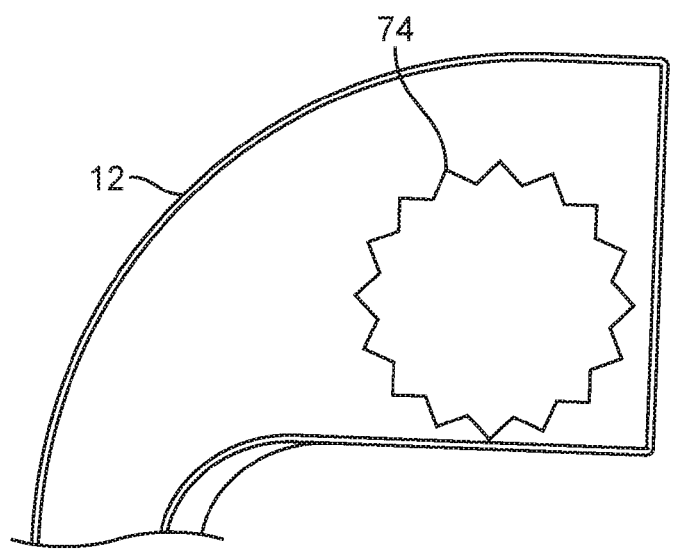
FIG. 7B is a side view of the retractor blade in FIG. 7A.
Figure 7C:
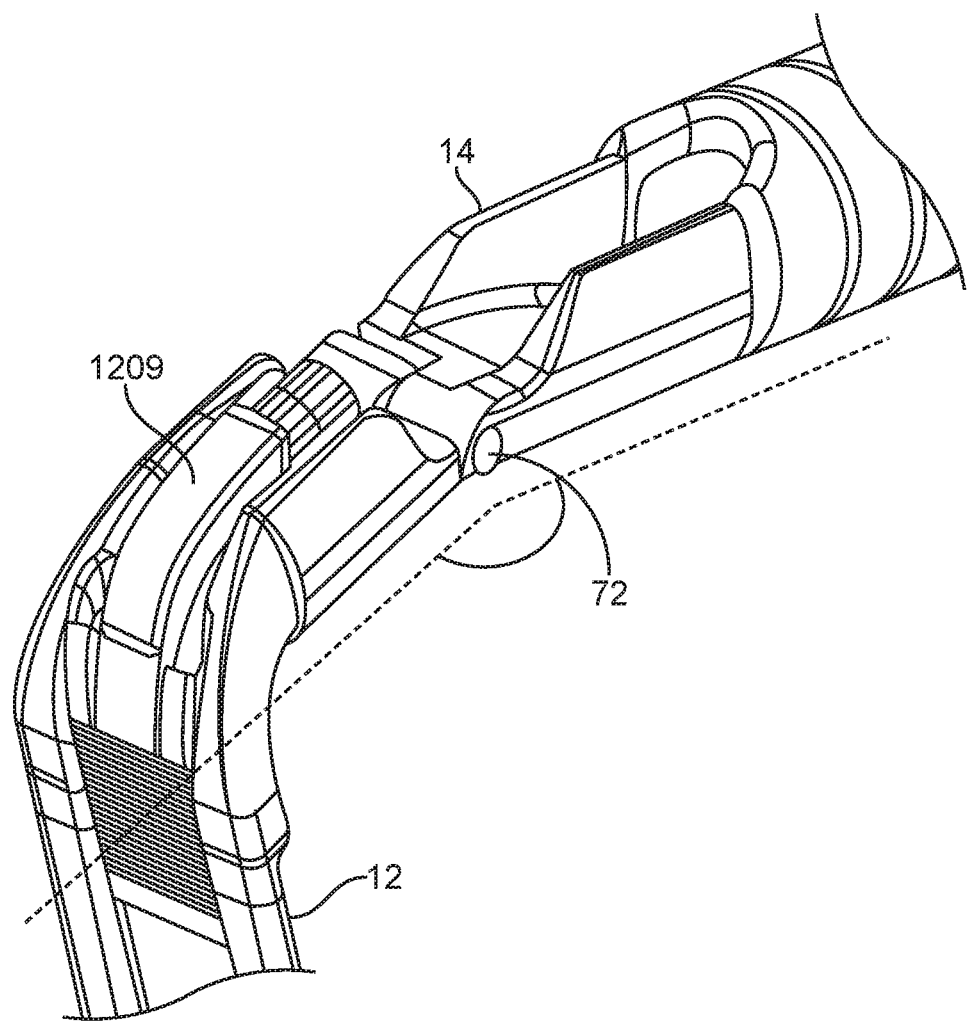
FIG. 7C illustrates the retractor of FIG. 7A coupled to a handle, and with an illumination blade device.

In one exemplary embodiment, the adjustment mechanism may comprise a splined pin disposed laterally in a distal portion of the handle 14. FIG. 7A illustrates retractor blade 12 having a splined channel 74 extending laterally through the retractor blade and splined pin 72 passing therethrough. The splined pin 72 also is disposed in a distal portion of handle 14. FIG. 7B is a side view of retractor blade 12 highlighting the splined channel 74 in the retractor blade. When the splined pin 72 is retracted from the splined channel 74, the retractor blade 12 may be pivoted to adjust θ. Once the desired angle is set, the pin may be placed back in the splined hole 74, thereby locking the retractor blade in position. The splines may be adjusted to any pitch, but in preferred embodiments, the splines are spaced apart so that the retractor blade may be adjusted in increments of every 5°, more preferably every 3°, and most preferably every 2°. One of skill in the art appreciates that any pitch may be used, and thus the exemplary pitches are not intended to be limiting. The splined pin 72 may also be spring loaded so that an operator may push it out of the way to allow retractor blade adjustment, and the spring may be biased to push the splined pin back into engagement with the splined hole 74 to lock the retractor blade into the desired angle. FIG. 7C illustrates the retractor blade 12 coupled with handle 14, and with blade illumination device 1209 coupled to the retractor blade. Splined pin 72 is more clearly illustrated in this view.

Retractor Blade

FIG. 8A illustrates a side view of surgical retractor having a handle 14 and a retractor blade 12. In this exemplary embodiment, the retractor blade 14 is disposed in a plane that is transverse to the plane in which the handle 14 lies. In the embodiment of FIG. 8A, the retractor blade is perpendicular to the handle. The retractor blade 12 includes a distal tip 82 that may be curved upward towards the proximal end of the handle. Any of the surfaces of the retractor blade and/or the distal tip may be textured in order to facilitate grasping of tissue during retraction. FIG. 8B illustrates an end view of the retractor blade in FIG. 8A. An upper surface 88 of the retractor blade may be concave, and a slotted region or channel 86 may extend along the length of the retractor blade. This slotted region accommodates the lighting elements that are described herein. Additionally, a plurality of channels 84 may run along the length of the retractor blade 12 and the channels 84 can be used to suction smoke or fumes from the surgical field as will be described in greater detail below. The length of the retractor blade, width and thickness can be any dimension suitable for the target anatomy. Preferably, several different retractor blades are provided so that the operator may select the retractor blade most suited for the procedure. Additionally, the retractor blade may also include wings 90 on either side of the retractor blade 12, such as in FIG. 9. The wings 90 help increase the area of the retractor blade, thereby allowing more tissue to be retracted, as well as helping to keep tissue from slipping off the retractor blade during retraction. FIG. 9 also illustrates how in some embodiments, the distal tip 82 of the retractor blade may be removable so that it may be replaced with a distal tip better suited for the surgical procedure being performed. These tips may be provided sterile. The distal tip may be press fit, snap fit, or otherwise mechanically coupled to the retractor blade. In other embodiments, the distal tip is fixedly attached to the retractor blade. The distal tip may have any number of geometries that help retract tissue. For example, the distal tip may curve upwards or it may be flat and planar. The distal tip may also include a textured surface 94 to help with grasping tissue during retraction. The texturing may be machined directly into the distal tip 82, or in other embodiments, the texturing may be removably attached to the distal tip. Exemplary texturing may include knurling, teeth, or roughened surfaces. A rubberized surface may also be used to help tissue retention. Additionally, the anti-slip features may be removably applied to the retractor blade using a textured tape, plastic sleeve, fabric sock, or polymer tip. In still other embodiments, the retractor blade may include fenestrations including holes or slots that help to catch tissue that is disposed in the fenestrations during retraction. The retractor blade may also have a hole or slot therethrough that exposes the rear surface of the blade illuminator. The blade illuminator may have protuberances that are integral with the blade illuminator or that are attached thereto and that protrude through the retractor blade hole or slot to help secure the blade illuminator to the retractor blade.

Figure 10A:
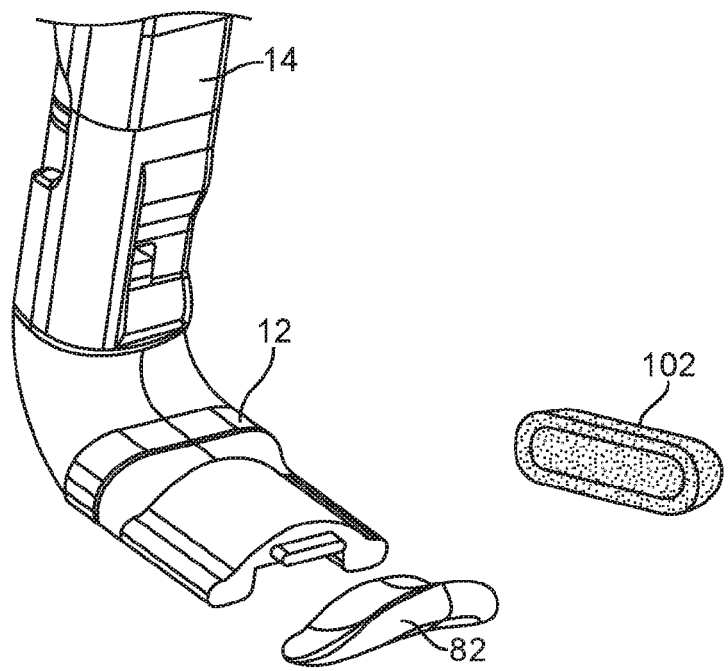
FIGS. 10A-10B illustrate a cover disposed over the distal tip of the retractor blade.
Figure 10B:
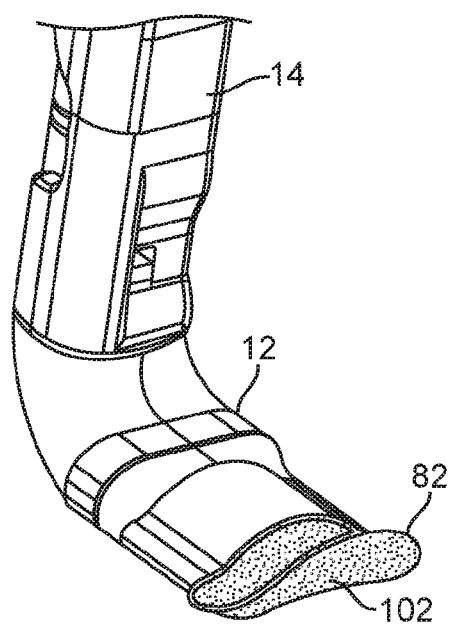
Figure 10C:
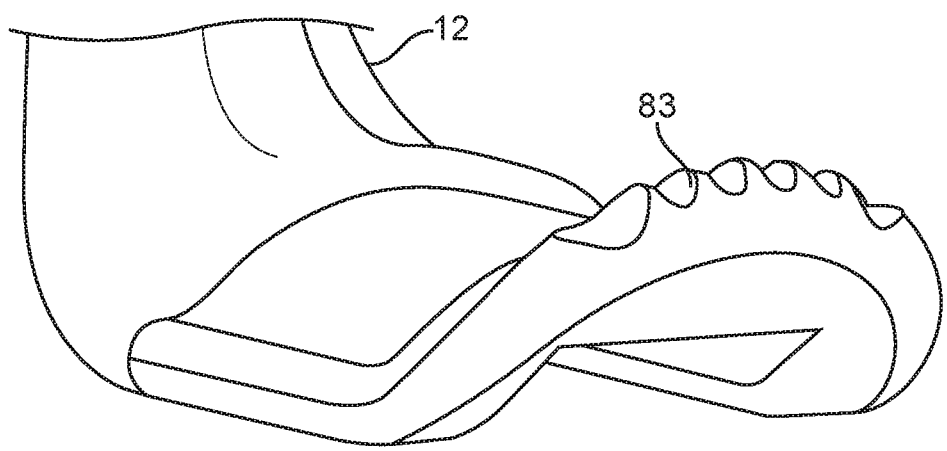
FIG. 10C illustrates teeth on the distal tip of the retractor blade.

FIG. 10A illustrates a surgical retractor having a handle 14 with retractor blade 12 and a removable distal tip 82. A cover 102 may be placed over the distal tip 82 in order to allow different surface textures to be applied to the distal tip. The cover may be removed after the surgical procedure and discarded in order to facilitate cleaning and re-sterilization of the retractor if re-useable. In some embodiments, some or all components of the surgical retractor may be single-use and disposed of after use. FIG. 10B illustrates the distal tip 82 of the retractor blade 12 once the cover 102 has been disposed thereover. In still other embodiments, the retractor blade may have fixed or retractable barbs that help grasp tissue. FIG. 10C illustrates another embodiment where the distal tip of the retractor blade 12 includes teeth 83 for helping to grasp tissue, or to facilitate dissection of tissue with the retractor blade.

Retractors are often used in conjunction with electrosurgical equipment. Because the retractor blades are in close proximity to the electrosurgical probe, unwanted arcing can occur between the retractor blade and electrosurgical probe. It is therefore desirable to insulate all or a portion of the retractor blade. This may be accomplished by fabricating the retractor blade from a non-conductive material such as a polymer or a ceramic, or the blade may be made from a metal and then covered with a non-conductive coating such as a polymer like parylene or anodized. Any of the features of the retractor blade disclosed herein may be used with any of the other embodiments of retractor blades described elsewhere.

Illumination Blade Device

Figure 11A:
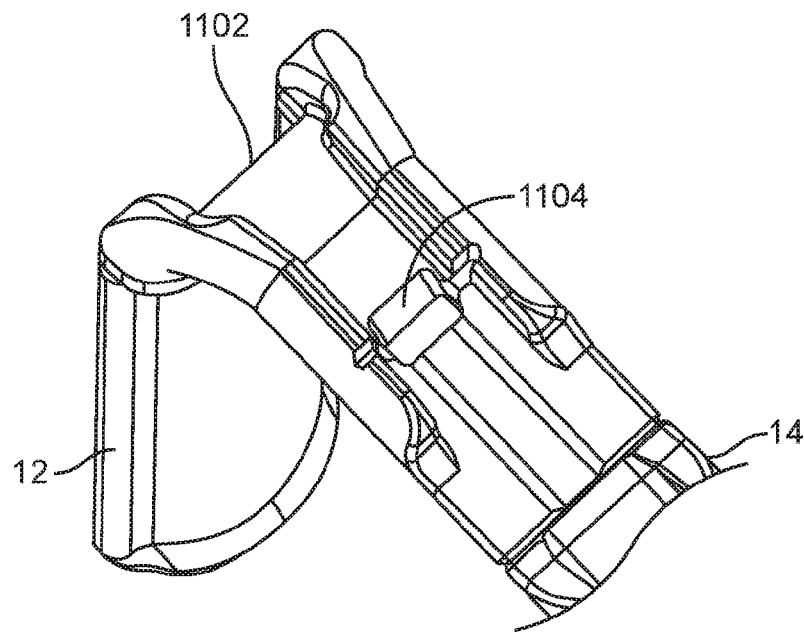
FIGS. 11A-11E illustrate coupling of an illuminator blade with the retractor blade and handle.
Figure 11B:
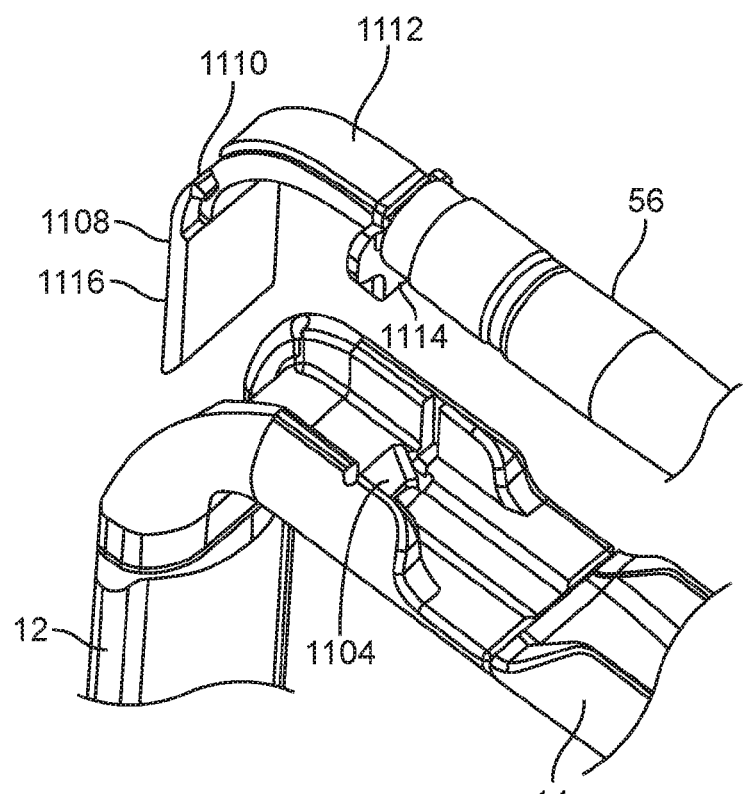

FIGS. 11A-11E illustrate coupling of an illumination blade device with the retractor and the handle. In FIG. 11A, the retractor blade 12 is already coupled with the handle 14, although the retractor blade may be coupled after the illumination device has been coupled with the handle. A distal portion of handle 14 includes a slot 1104 for releasably attaching the illumination device with the handle 14. A channel or slot 1102 in retractor blade 12 allows the illumination blade device to be disposed therein. In FIG. 11B, the illumination blade device 1108 is coupled to cable 56 thereby optically coupling the illumination blade device 1108 with a light source (not shown). In other embodiments, a light pipe or optical fibers may be fixedly coupled to the handle and the illumination blade device may be coupled to a distal end of the light pipe or optical fibers, and the proximal end of the handle is then coupled with a light source. Thus, the cable need not be fed all the way through the handle.

Figure 11C:
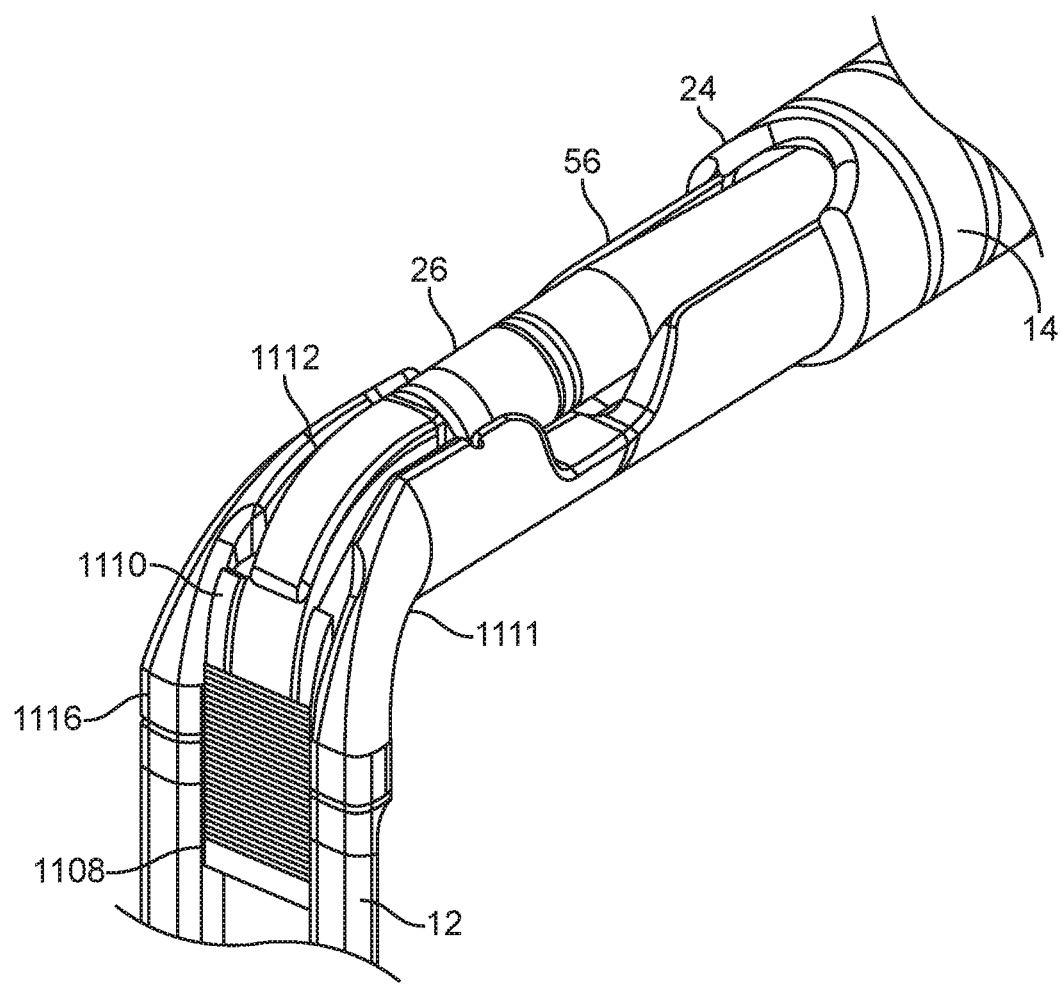
Figure 11D:
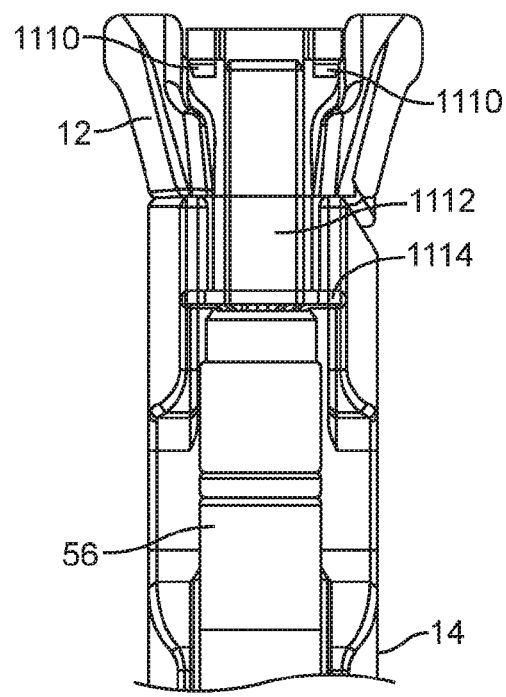
Figure 11E:
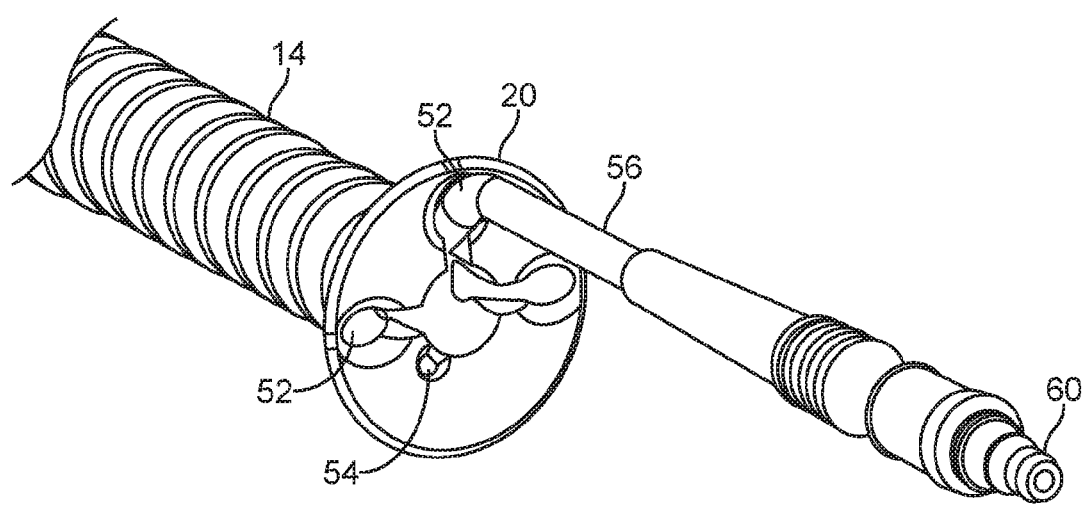

The illumination blade device 1108 preferably includes a light output zone 1116 where light is extracted from the illumination blade and directed toward the surgical field. Additionally, the engagement elements such as tabs 1110 in dead zones of the illumination blade device allow the blade illuminator 1108 to be disposed against the retractor blade while maintaining an air gap between the active zones of the illuminator blade and the retractor blade, as will be discussed in greater detail below. Additionally a shield 1112 disposed over a portion of the blade illumination device prevents it from being scratched or damaged by other surgical instruments being used, as well as preventing glare from shining back into an operator's face. A plate 1114 allows the blade illuminator to be snapped or otherwise releasably coupled with the handle by placing the plate 1114 into slot 1104. FIG. 11C is a perspective view of the surgical retractor after the illumination blade device has been coupled with the handle. Cable 56 is exposed near a distal portion of the handle in an open channel 26, but eventually runs through the channel 24 in handle 14 until the cable exits the proximal end of the handle through a positioning aperture 52 as seen in FIG. 11E. The cable 56 can then be optically coupled with a light source. FIG. 11D is a top view of the surgical retractor showing the illumination blade device coupled with the handle and engaging the retractor blade.

Figure 11F:
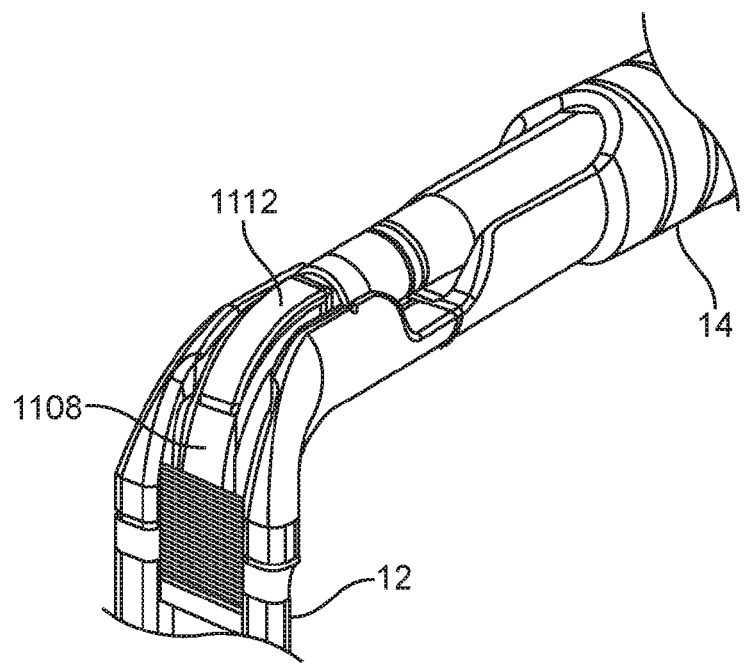
FIGS. 11F-11G illustrate various sizes of illuminator blades.
Figure 11G:
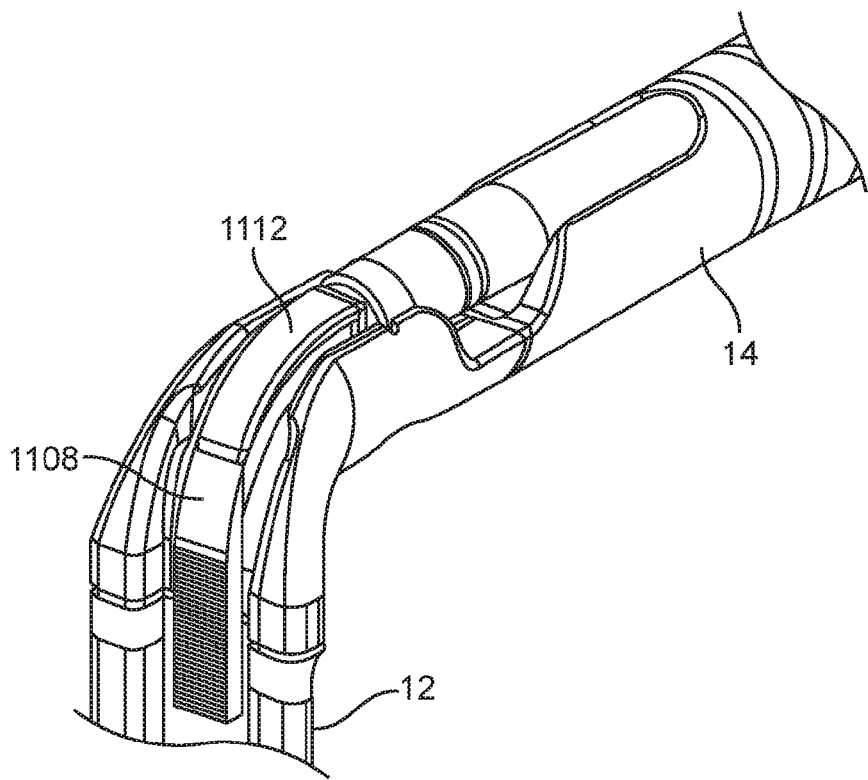

FIGS. 11F-11G illustrate various sizes of illuminator blades 1108 disposed in a channel of the retractor blade 12. The illuminator blades 1108 may have a width that extends across the width of the retractor blade channel as seen in FIG. 11F, or the illuminator blade 1108 may be narrower than the channel as seen in FIG. 11G. Additionally, the illuminator blade length may be any length—from longer than the retractor blade, to shorter than the retractor blade, or it may the same length as the retractor blade.

Figure 12A:
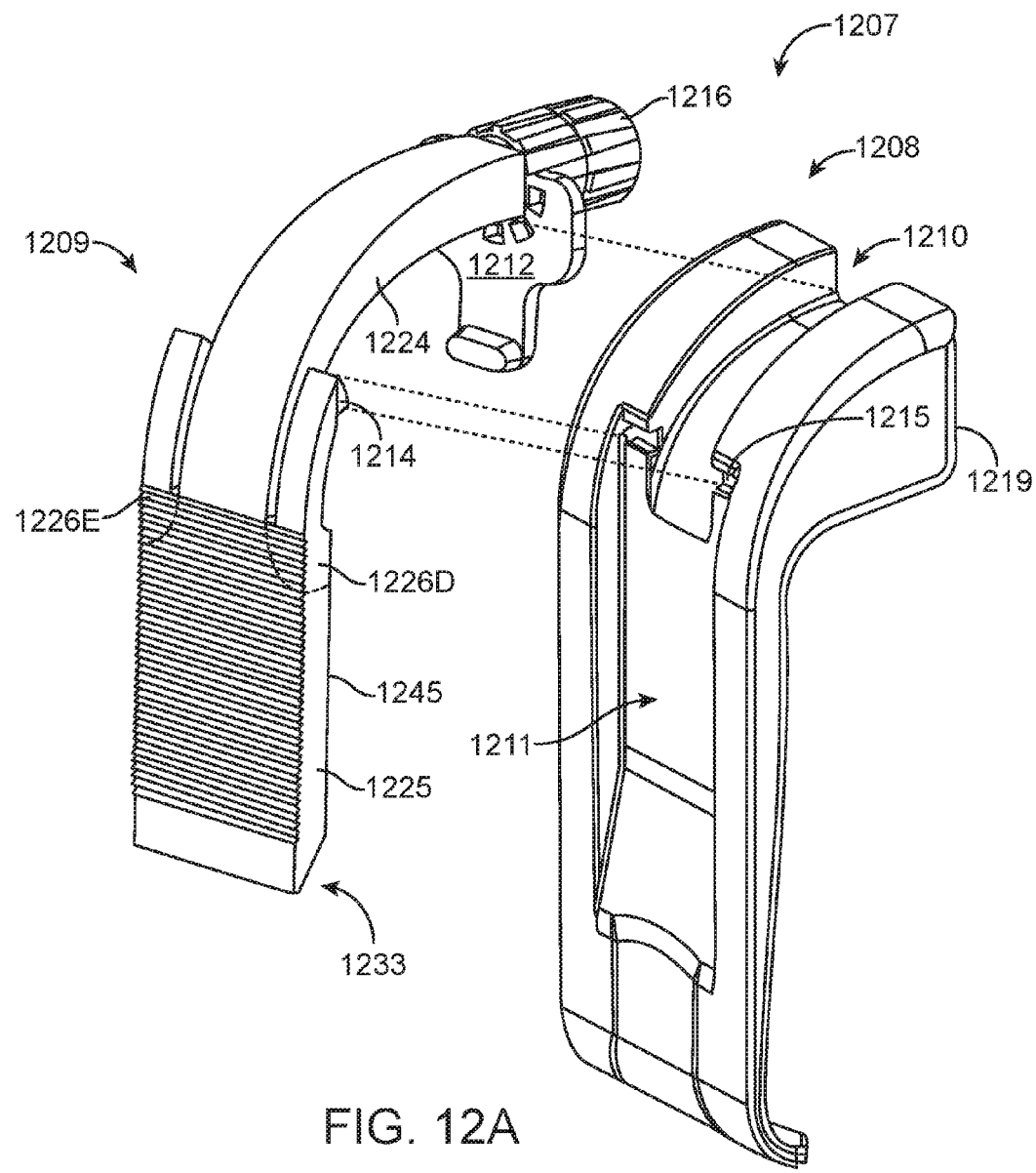
FIG. 12A is a perspective view of an illuminated retractor blade.
Figure 12B:
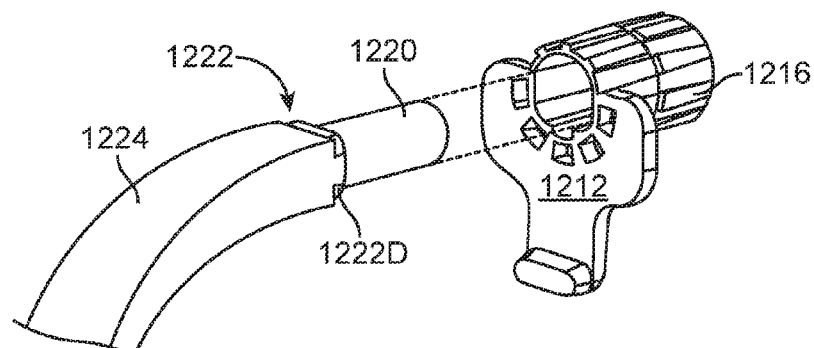
FIG. 12B is an exploded view of the input collar and the illumination blade input of the illuminated retractor blade in FIG. 12A.
Figure 12C:
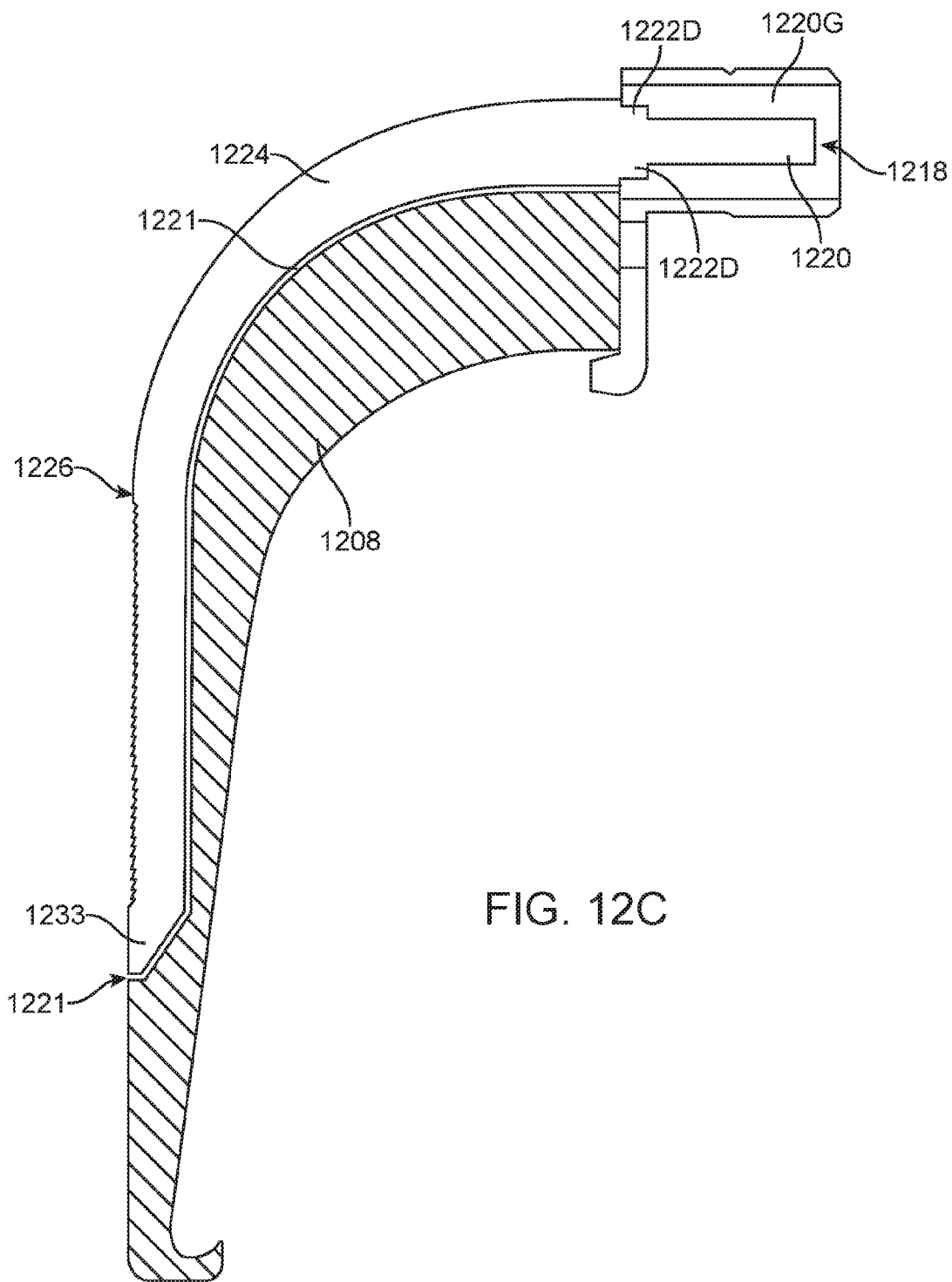
FIG. 12C is a cross-sectional view of the illuminator blade and retractor blade of FIG. 12A.

FIG. 12A more clearly illustrates engagement of the illuminator blade device (also referred to herein as an illuminator blade) with the retractor blade. Illuminated retractor 1207 is composed of retractor blade 1208 and illumination blade 1209. Retractor blade 1208 may be used with any of the embodiments disclosed herein, or it may be used with other retractor systems such as a McCulloch retraction system. Retractor blade 1208 includes one or more mechanical connectors and may be releasably coupled with any of the handles described in this specification. Any of the coupling mechanisms disclosed herein may be used. Neck slot or channel 1210 accommodates neck zone 1224 of the illuminator blade 1209 and blade slot 1211 accommodates output blade 1225 of the illuminator blade 1209 while maintaining an air gap between active zones of the illumination blade and the retractor. Two or more engagement elements such as blade or plate 1212 and tabs 1214 secure illumination blade 1209 to retractor blade 1208. Each tab 1214 engages one or more engagement receptacles such as receptacles or recesses 1215. Plate 1212 is joined to collar 1216, and when collar 1216 removably engages input dead zone 1222D, the collar surrounds illumination blade input 1218 as seen in FIG. 12C. The removable engagement of collar 1216 to input dead zone 1222D also brings plate 1212 into contact with end surface 1219 of the retractor blade. Collar 1216 securely engages dead zone 1222D and surrounds cylindrical input zone 1220 and forms input air gap 1220G. Engagement at dead zones minimizes interference with the light path by engagement elements such a plate 1212 and tabs 1214. Plate 1212 engages end surface 1219 and tabs 1214 resiliently engage recesses 1215 to hold illumination blade 1209 fixed to retractor blade 1208 without contact between active zones of illumination blade 1209 and any part of retractor blade 1208.

Figures 12D, 12E:
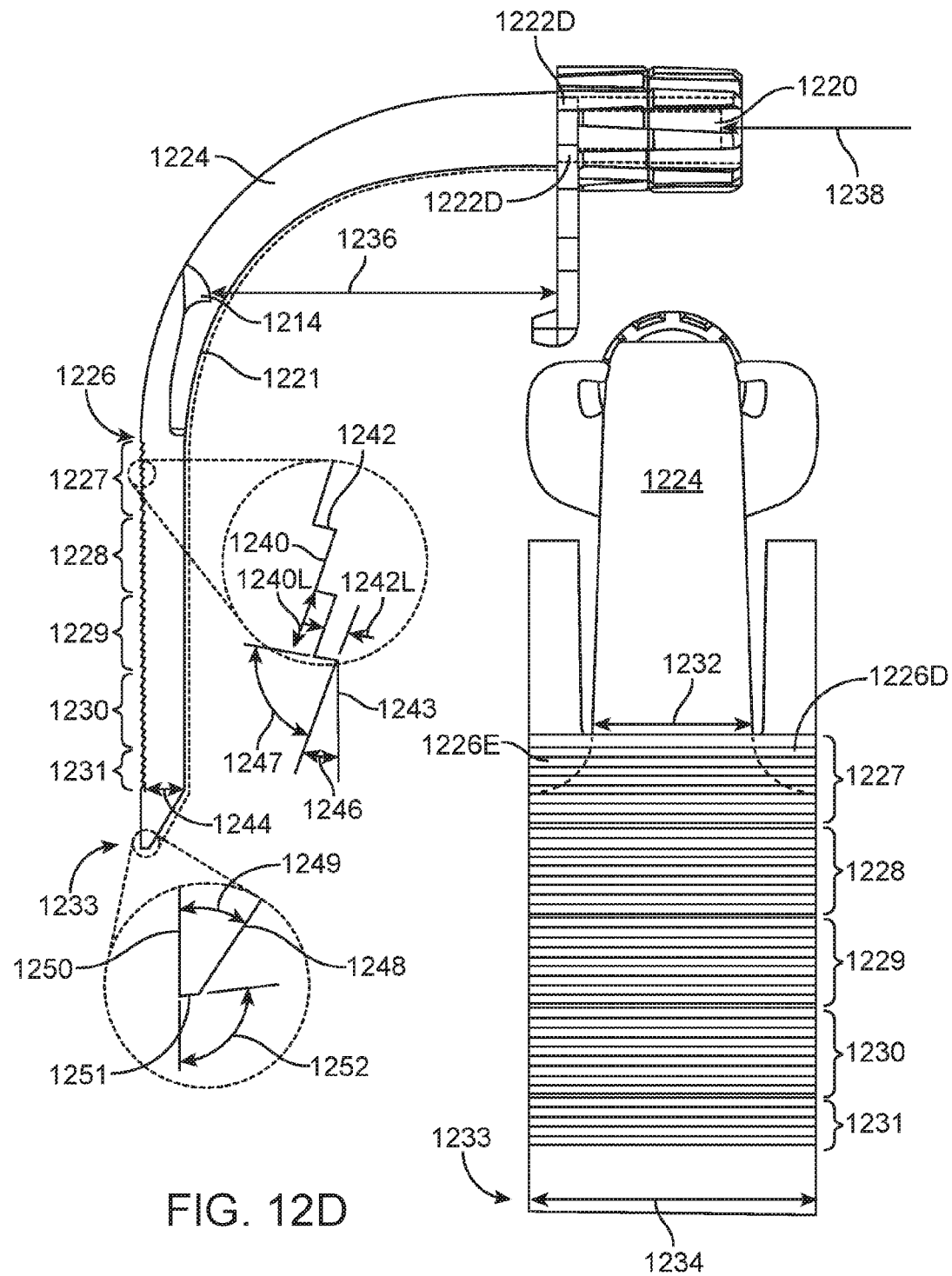
FIG. 12D is a side view of the illuminator blade in FIG. 12A.
FIG. 12E is a front view of the illuminator blade in FIG. 12A.

Illumination blade 1209 is configured to form a series of active zones to control and conduct light from illumination blade input 1218 of the cylindrical input zone 1220 to one or more output zones such as output zones 1227 through 1231 and output end 1233 as illustrated in FIGS. 12D-12E. Illumination blade 1209 also includes one or more dead zones such as zones 1222D, 1226D and 1226E. Dead zones are oriented to minimize light entering the dead zone and thus potentially exiting in an unintended direction. As there is minimal light in or transiting dead zones by total internal reflection they are ideal locations for engagement elements to secure the illumination blade to the retractor.

Light is delivered to illumination blade input 1218 using any conventional mechanism such as a standard ACMI connector having a 0.5 mm gap between the end of the fiber bundle and illumination blade input 1218, which is 4.2 mm diameter to gather the light from a 3.5 mm fiber bundle with 0.5 NA. Light incident to illumination blade input 1218 enters the illumination blade through generally cylindrical, active input zone 1220 and travels through active input transition 1222 to a generally rectangular active retractor neck 1224 and through output transition 1226 to output blade 1225 which contains active output zones 1227 through 1231 and active output end 1233. Neck 1224 is generally rectangular and is generally square near input transition 1222 and the neck configuration varies to a rectangular cross section near output transition 1226. Output blade 1225 has a generally high aspect ratio rectangular cross-section resulting in a generally wide and thin blade. Each zone is arranged to have an output surface area larger than the input surface area, thereby reducing the temperature per unit output area.

In the illustrated configuration illumination blade 1209 includes at least one dead zone, dead zone 1222D, generally surrounding input transition 1222. One or more dead zones at or near the output of the illumination blade provide locations to for engagement elements such as tabs to permit stable engagement of the illumination blade to the retractor. This stable engagement supports the maintenance of an air gap such as air gap 1221 adjacent to all active zones of the illumination blade as illustrated in FIG. 12C. Neck zone 1224 ends with dimension 1232 adjacent to output transition 1226 which extends to dimension 1234 at the output zones. The changing dimensions result in dead zones 1226D and 1226E adjacent to output transition 1226. These dead zones are suitable locations for mounting tabs 1214 to minimize any effects of the engagement elements on the light path.

To minimize stresses on the light input and or stresses exerted by the light input on the illumination blade, the engagement elements are aligned to form an engagement axis such as engagement axis 1236 which is parallel to light input axis 1238.

Output zones 1227, 1228, 1229, 1230 and 1231 have similar configurations with different dimensions. Referring to the detailed view of FIG. 12D, the characteristics of output zone 1227 are illustrated. Each output zone is formed of parallel prism shapes with a primary surface or facet such a primary facet 1240 with a length 1240L and a secondary surface or facet such as secondary facet 1242 having a length 1242L. The facets are oriented relative to plane 1243 which is parallel to and maintained at a thickness or depth 1244 from rear surface 1245. In the illustrated configuration, all output zones have the same depth 1244 from the rear surface.

The primary facets of each output zone are formed at a primary angle 1246 from plane 1243. Secondary facets such as facet 1242 form a secondary angle 1247 relative to primary facets such as primary facet 1240. In the illustrated configuration, output zone 1227 has primary facet 1240 with a length 1240L of 0.45 mm at primary angle of 27 degrees and secondary facet 1242 with a length 1242L of 0.23 mm at secondary angle 88 degrees. Output zone 1228 has primary facet 1240 with a length 1240L of 0.55 mm at primary angle of 26 degrees and secondary facet 1242 with a length 1242L of 0.24 mm at secondary angle 66 degrees. Output zone 1229 has primary facet 1240 with a length 1240L of 0.53 mm at primary angle of 20 degrees and secondary facet 1242 with a length 1242L of 0.18 mm at secondary angle 72 degrees. Output zone 1230 has primary facet 1240 with a length 1240L of 0.55 mm at primary angle of 26 degrees and secondary facet 1242 with a length 1242L of 0.24 mm at secondary angle 66 degrees. Output zone 1231 has primary facet 1240 with a length 1240L of 0.54 mm at primary angle of 27 degrees and secondary facet 1242 with a length 1242L of 0.24 mm at secondary angle 68 degrees. Thus, the primary facet 1240 in preferred embodiments forms an acute angle relative to the plane in which the rear surface 1245 lies, and the secondary facet 1242 in preferred embodiments forms an obtuse angle relative to the plane in which the rear surface 1245 lies. These preferred angles allow light to be extracted from the illuminator blade so that light exits laterally and distally toward the surgical field in an efficient manner, and the illuminator blade to be injection molded and easily ejected from the mold. Other angles are possible, as will be appreciated by one of skill in the art.

Output end 1233 is the final active zone in the illumination blade and is illustrated in detail in FIG. 12D. Rear reflector 1248 forms angle 1249 relative to front surface 1250. Front surface 1250 is parallel to rear surface 1245. Terminal facet 1251 forms angle 1252 relative to front surface 1250. In the illustrated configuration, angle 1249 is preferably 32 degrees and angle 1252 is preferably 95 degrees. This distal tip geometry helps to prevent light from reflecting back proximally toward the physician, thereby helping to prevent glare.

Other suitable configurations of output structures may be adopted in one or more output zones. For example, output zones 1227 and 1228 might adopt a concave curve down and output zone 1229 might remain generally horizontal and output zones 1230 and 1231 might adopt a concave curve up. Alternatively, the plane at the inside of the output structures, plane 1243 might be a spherical section with a large radius of curvature. Plane 1243 may also adopt sinusoidal or other complex geometries. The geometries may be applied in both the horizontal and the vertical direction to form compound surfaces.

In other configurations, output zones may provide illumination at two or more levels throughout a surgical site. For example, output zones 1227 and 1228 might cooperate to illuminate a first surgical area and output zones 1229 and 1230 may cooperatively illuminate a second surgical area and output zone 1231 and output end 1233 may illuminate a third surgical area. This configuration eliminates the need to reorient the illumination elements during a surgical procedure.

Smoke Evacuation

Many surgical retractors are used in conjunction with electrosurgical instruments such as RF probes for cautery. Electrosurgical instruments often generate smoke or other noxious fumes that can obstruct the field of view or be unpleasant. Therefore, surgical retractors may also include a feature for smoke evacuation. Often, smoke or noxious fumes are evacuated with a vacuum tube that is either separate from the retractor, or coupled with the retractor. A vacuum line is coupled to the vacuum tube, and the smoke or fumes may be evacuated. The disadvantage of these systems is that the separate vacuum tube takes up precious space in the already crowded surgical field. With incisions becoming smaller and smaller, it is becoming more important to reduce the volume of surgical instruments. Therefore it would be advantageous to provide a surgical retractor that can evacuate smoke or fumes without taking up additional space.

Figure 13A:
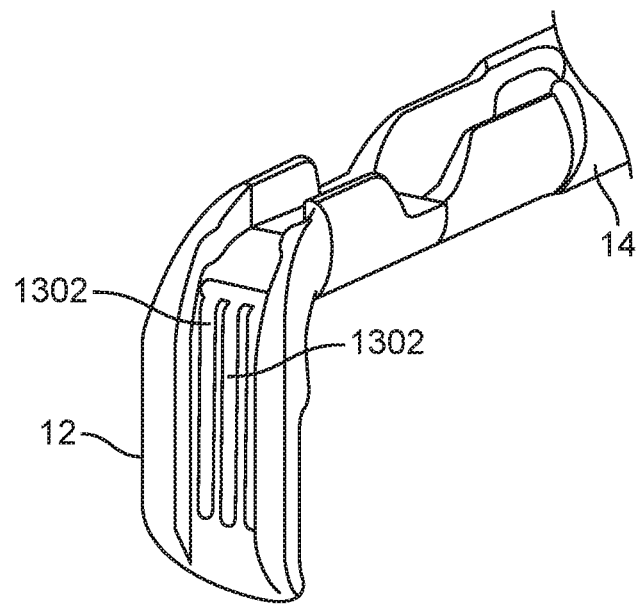
FIGS. 13A-13J illustrate a retractor blade having channels for smoke evacuation.
Figure 13B:
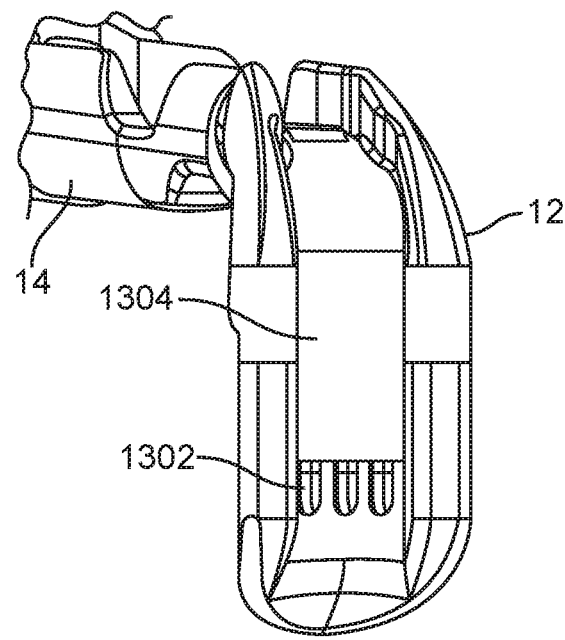
Figure 13C:
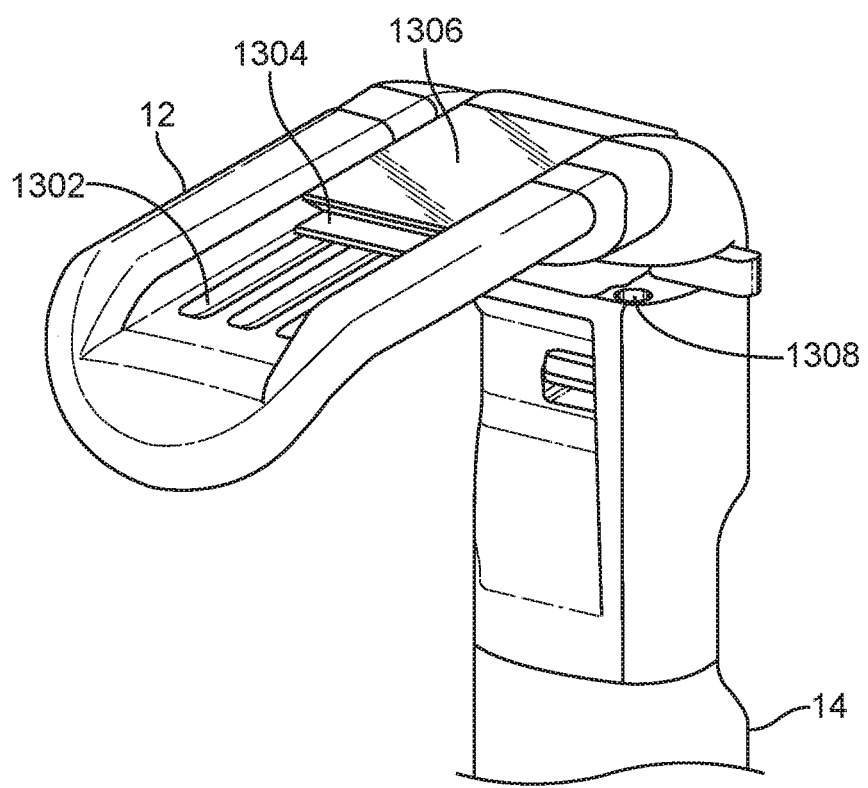

FIGS. 13A-13C illustrate an exemplary embodiment of a retractor having an integral smoke evacuation system. In FIG. 13A, the retractor includes handle 14 and retractor blade 12. The handle 14 and blade 12 may be any of the handles or blades disclosed herein. The retractor blade 12 includes a plurality of longitudinal channels 1302 running along the length of the blade. While only one channel is required, preferred embodiments have multiple channels. When a single wide channel is included, it is possible for other surgical instruments to get caught in the channel, between the retractor blade and any vanes or illumination blades that are disposed thereover. Thus, it can be advantageous to use multiple narrow channels to minimize the opportunity for the instruments to catch. The channels may be parallel with one another, or other geometries are also possible. The illumination blade device, (also referred to as a blade illuminator or illumination blade) may then be sealingly disposed over the channels and coupled with the retractor blade to form a gap or plenum between the channels and the bottom surface of the illuminator blade. A vacuum tube may then be coupled with the retractor blade so that fumes are drawn out of the surgical field along the plenum. Thus, smoke is evacuated without requiring an additional tube that occupies space in the surgical field. Depending on the size and length of the illuminator blade being used to provide light to the surgical field, the blade may not cover the channels enough to allow adequate vacuum to be created for effective smoke evacuation. Thus, in some cases, as seen in FIG. 13B, a cover or vane 1304 may be disposed over the channels to accommodate different illuminator blades, as well as to control the amount of vacuum created. The cover or vane 1304 may be press fit into the retractor blade and disposed over the channels 1302 to form the plenum, or the vane 1304 may be slidably advanced along slots in the retractor blade. In still other embodiments, the vane 1304 may be coupled with the blade illuminator. The blade illuminator and vane is then coupled with the retractor blade such that the vane covers enough area of the channels to create adequate vacuum for smoke evacuation while maintaining an air gap between an upper surface of the vane and a lower surface of active zones of the illuminator blade in order to minimize light loss. FIG. 13C illustrates the blade illuminator 1306 disposed over the vane 1304 which is then positioned over the plurality of channels 1302. The bottom surface of the vane may fit flush against the top surface of the channels to prevent surgical instruments from catching. Similarly, in embodiments where the blade illuminator is disposed directly over the channels without a vane, the tip of the blade illuminator may also fit flush against the top surface of the channels to prevent other surgical instruments from catching. Thus the plenum is formed by assembly of the vane(s) and/or illuminator blade with the retractor blade. A channel such as channel 42 (seen in FIG. 4) may run through the handle wall and exit at a distal aperture 1308 of the handle 14. A vacuum tube may be slidably disposed in the channel 42 and exit aperture 1308 and be coupled to retractor blade 12 so that the plurality of channels 1302 are fluidly coupled with the vacuum tube. In this or other embodiments, the vacuum tube may automatically fluidly connect with the retractor blade when the retractor blade is engaged with the handle. Thus separate coupling and uncoupling of the vacuum tube may not be required.

Figure 13D:
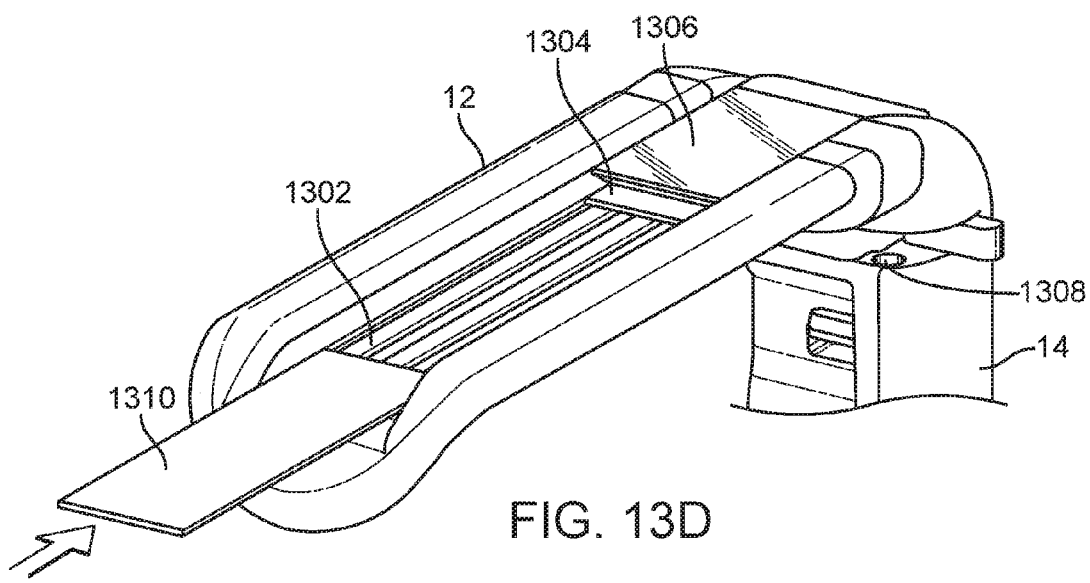
Figure 13E:
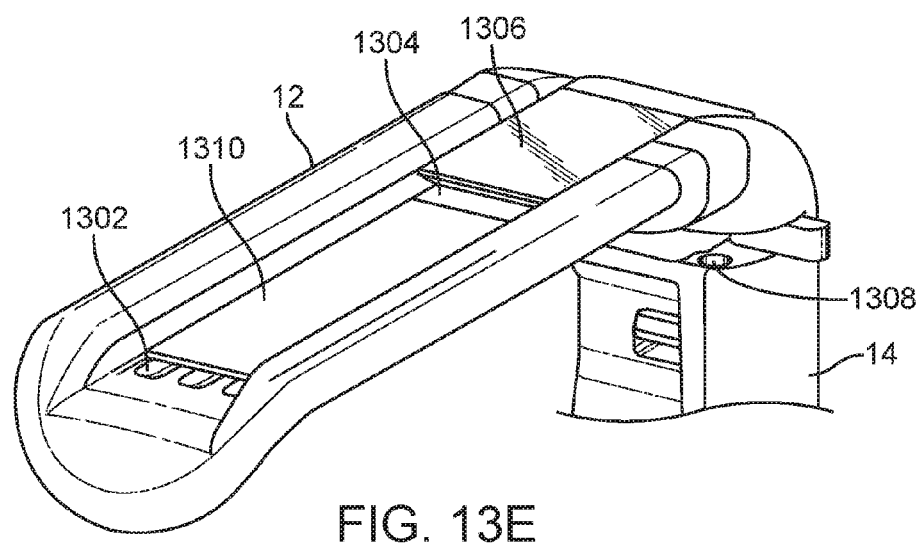
Figure 13F:
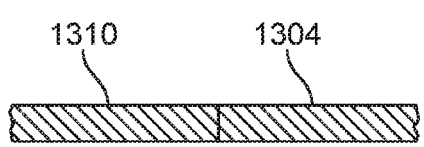
Figure 13G:
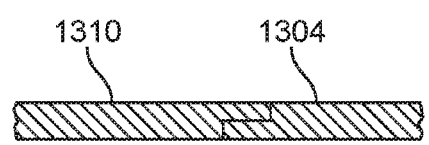
Figure 13H:
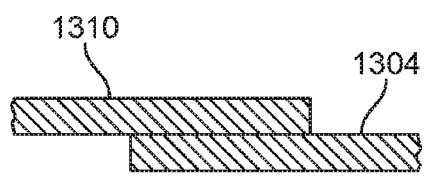

In situations where a long retractor blade 12 is used, the vane 1304 may not be long enough to cover the channels 1302 in the retractor blade 12. This prevents adequate vacuum from being generated. Thus, in some embodiments, a second vane 1310 may be disposed against the retractor blade 12 to control the area of the channels 1302 which are covered and form the plenum. The second vane may be slidably engaged with slots along the retractor blade sides as seen in FIG. 13D, or the second vane may be simply snap fit or otherwise disposed against the retractor blade. A gap is maintained between the bottom of the second vane and the channels so that smoke or fumes may be evacuated. FIG. 13E illustrates the second vane 1302 positioned against the first vane 1304. The two vanes may abut one another end-to-end as seen in FIG. 13F, or a joint such as a scarf joint may be used to couple the ends as seen in FIG. 13G. Many other joints may also be used. In some embodiments, the two vanes may be slidably disposed over one another as seen in FIG. 13H.

In either embodiment with one or two vanes, the vanes may be slidably moved along the longitudinal axis of the retractor blade. Thus some portions of the fume channels will be covered and others will be uncovered. The uncovered portions will allow fume extraction from that position. Thus, by sliding the vanes, the location of fume extraction may be controlled. This is advantageous in deep pockets where procedures are performed at multiple levels. Thus it may be advantageous to extract smoke from a first level and then smoke may be extracted from a second level.

Figure 13I:
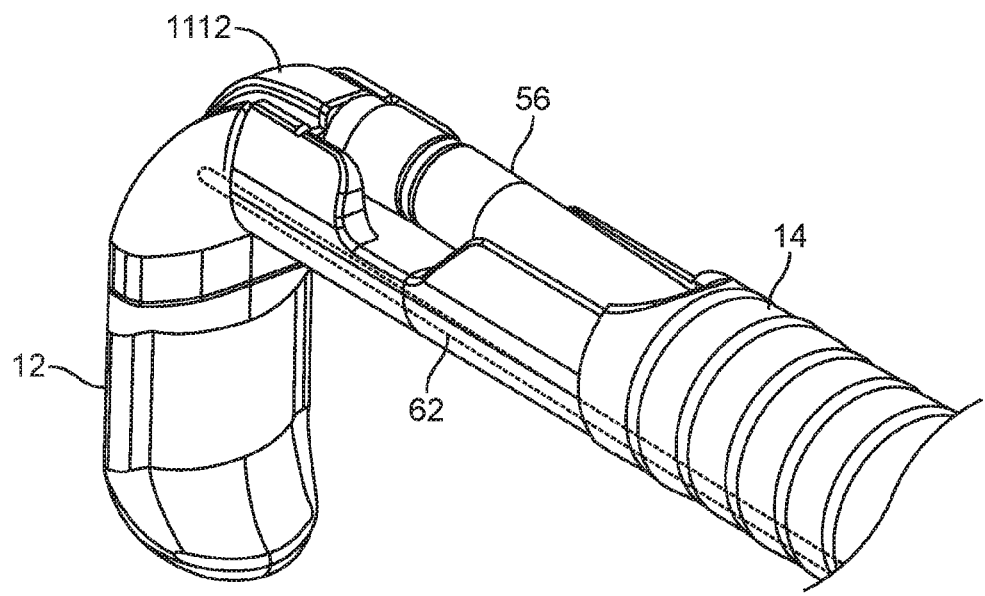
Figure 13J:
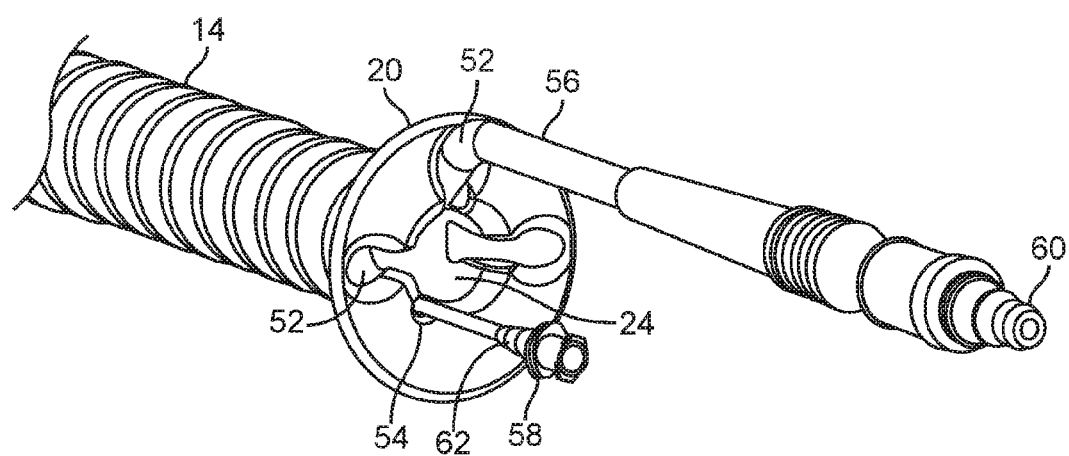

Once the blade illuminator and vanes have been positioned against the retractor blade 12, the light source cable 56 may be coupled to the blade illuminator, and suction tube 62 coupled to the retractor blade as seen in FIG. 13I. FIG. 13J illustrates the proximal end of handle 14 with the light input cable 56 and suction tube 62 extending through the handle as previously described above. One of skill in the art will appreciate that the illuminator blade, handle, retractor blade, light input cable, suction tube, etc. in the embodiment of FIGS. 13A-13J may be substituted for any of the other embodiments of illuminator blade, handle, retractor blade, light input cable, suction tube, etc. disclosed herein.

Figure 13K:
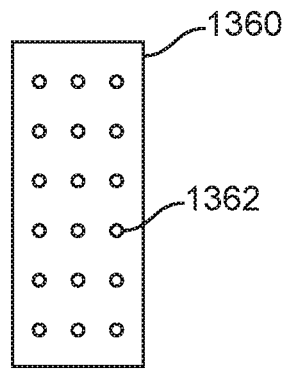
FIGS. 13K-13M illustrate alternative embodiments of vanes used to control suction.
Figure 13L:
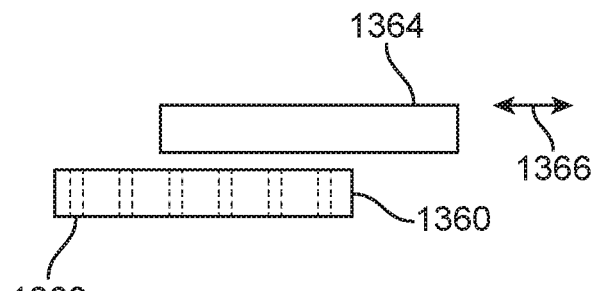
Figure 13M:
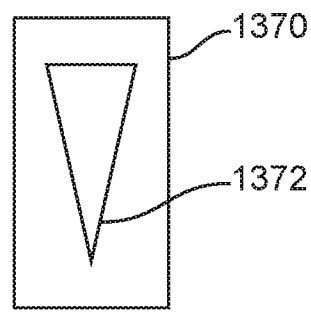

In an alternative embodiment, a first vane 1360 may have a plurality of through holes 1362, as seen in FIG. 13K. The first vane 1360 is disposed against the retractor blade and also against the plurality of channels. A second vane 1364 is slidably disposed over the first vane 1360 as seen in FIG. 13L. The second vane 1364 may be slidably advanced or retracted relative to the first vane as indicated by arrow 1366 in order to control how many of the apertures are exposed, thereby controlling the amount of suction provided by the vacuum. FIG. 13M illustrates an alternative embodiment of the first vane 1370 having a tapered slot 1372 passing through the vane. As the second vane is advanced or retracted, the amount of the slot exposed varies, thereby controlling the suction provided by the vacuum.

Figure 34:
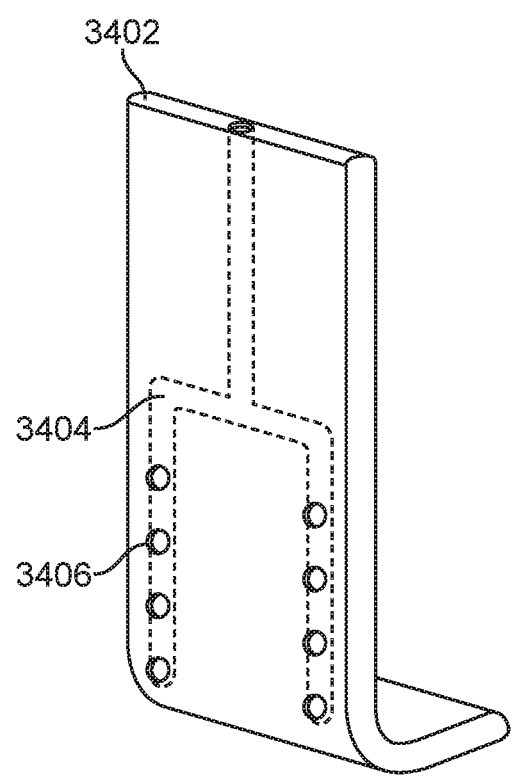
FIG. 34 illustrates an exemplary embodiment of a suction channel in a retractor blade.
Figures 35A, 35B:
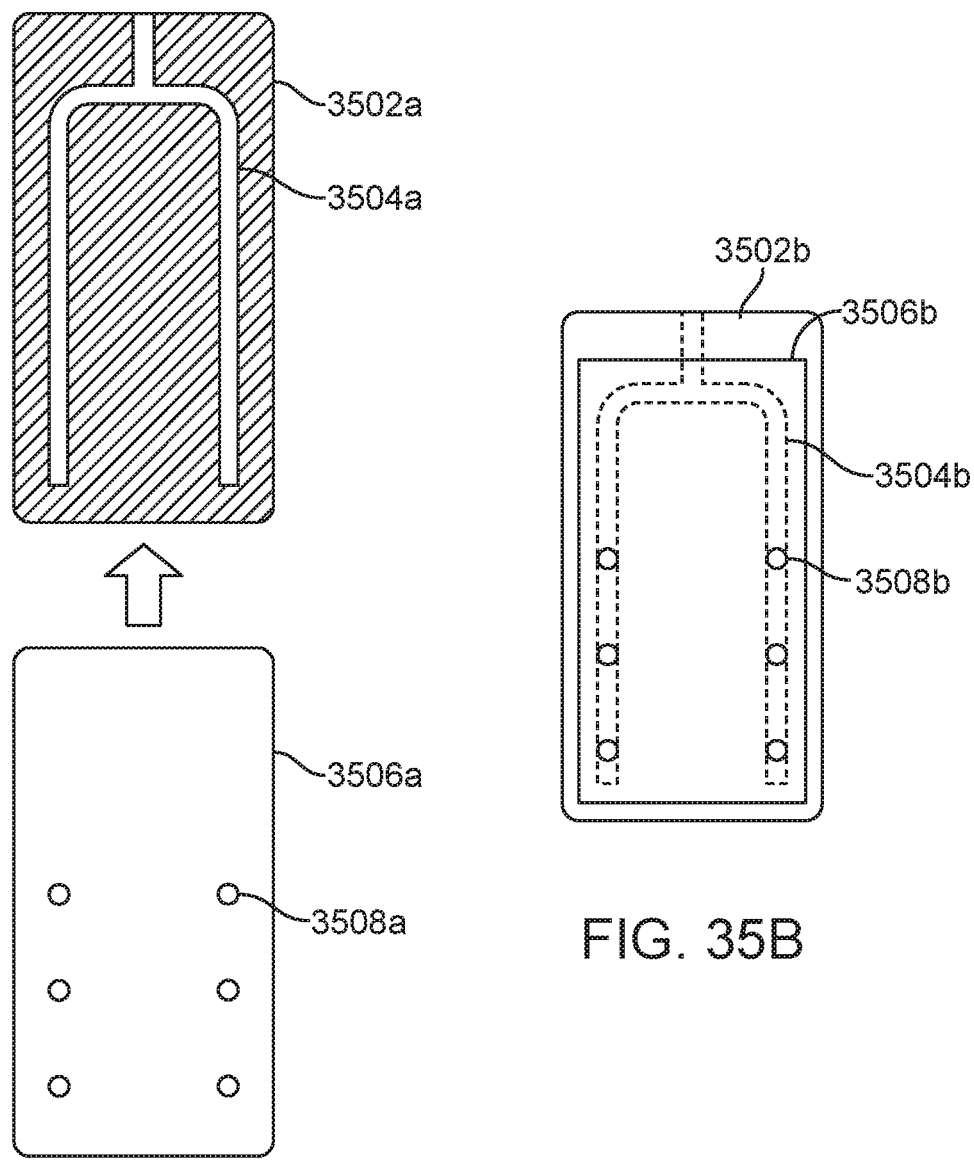
FIGS. 35A-35D illustrate still other exemplary embodiments of a suction channel in a retractor blade.
Figure 35C:
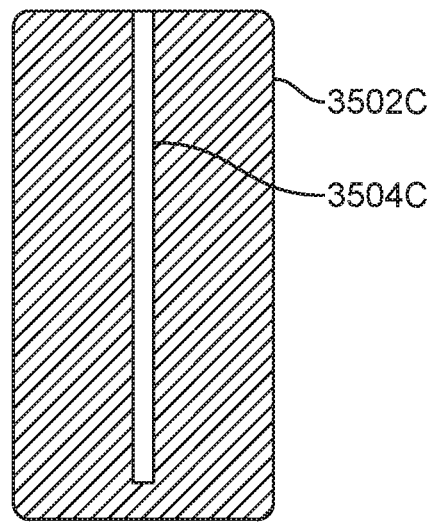
Figure 35D:
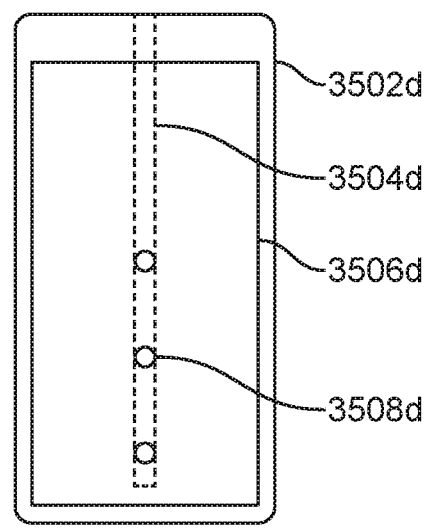

FIGS. 34 and 35A-35D illustrate alternative embodiments of the vacuum channels which may be used in any of the embodiments of illuminated retractors with smoke evacuation disclosed in this specification. The channels may be machined into the part, or they may be injection molded if the blade is molded. FIG. 34 illustrates the retractor blade 3402 having internal channels 3404 (as opposed to the open channels in the embodiment of FIG. 13A-13M). Suction holes are formed through an outer surface of the retractor blade until they are fluidly coupled with the internal channels 3404. The internal channels 3404 may be a single channel or a plurality of channels. Preferably the channels merge into a single channel near the proximal portion of the retractor blade so that the suction may be applied to the retractor blade at a single point. FIGS. 35A-35B illustrate a retractor blade with multiple open channels. For example in FIG. 35A, an open channel 3504*a* is disposed in the retractor blade 3502*a*. Two channels merge into a single channel near the proximal end of the retractor blade. A sliding cover or vane 3506*a* slides over the open channel to allow vacuum to be created and so that suction can be applied through suction holes 3508*a* in the cover 3506*a*. FIG. 35B illustrates a similar embodiment with the major exception being that the cover or vane 3506*b* is fixedly coupled to the retractor blade 3502*b*. Multiple vacuum channels are internal to the retractor blade. Vacuum is then drawn through suction holes 3508*b* in the cover. FIGS. 35C and 35D illustrate embodiments of retractor blades with a single open vacuum channel. In FIG. 35C a single open vacuum channel 3504 is disposed in the retractor blade 3502*c*. A slidable cover or vane 3506*c* may be placed over the channel into engagement with the retractor blade to seal the vacuum channel and allow vacuum to be drawn through suction holes 3508*c* in the cover. FIG. 35D illustrates a similar embodiment except that the cover 3506*d* is fixed to the retractor blade 3502*d*. Vacuum is applied through the single open channel 3504*d* and through suction holes 3508*d* in the cover. Additionally, as disclosed in greater detail in this specification, the blade illuminator may seal against the retractor blade to create the vacuum. Any of these embodiments may be used in the illuminated retractors with smoke evacuation features disclosed herein.

Figure 14A:
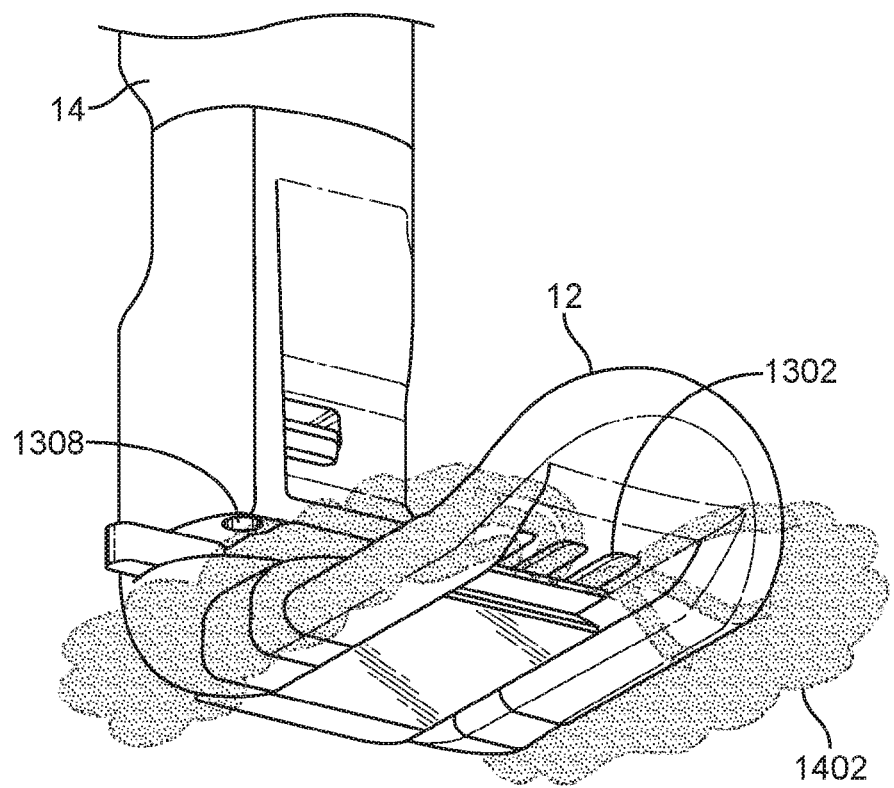
FIGS. 14A-14B illustrate evacuation of smoke using a retractor with channels.
Figure 14B:
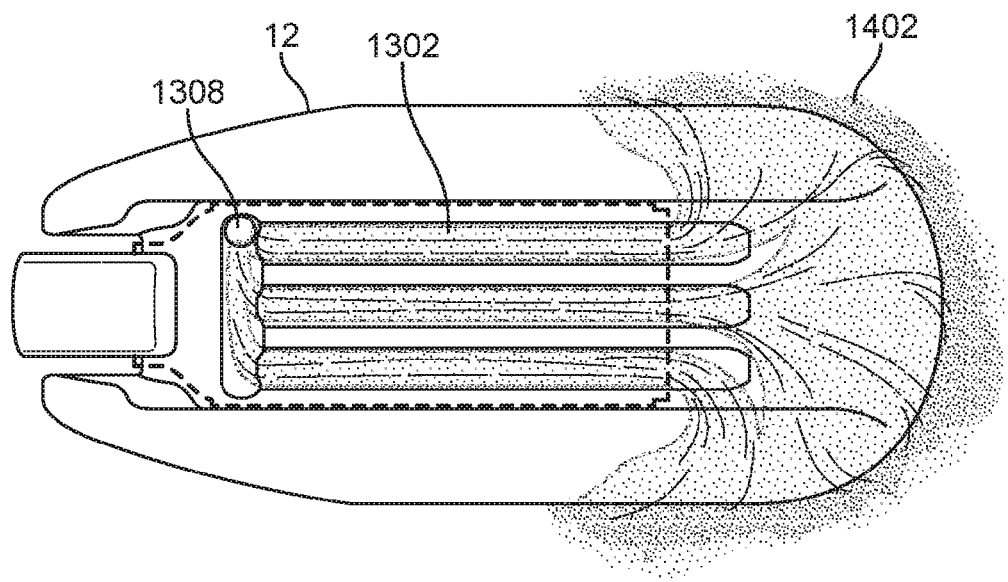

FIG. 14A illustrates a perspective view of the retractor in FIGS. 13A-13J. Smoke 1402 generated by electrosurgery or other noxious fumes is drawn into channels 1302 and then evacuated via a suction tube disposed in aperture 1308 in the handle 14. FIG. 14B illustrates a bottom view of the retractor blade 12 evacuating smoke 1302.

In alternative embodiments, the smoke evacuation channels may be integrated into the blade illumination device rather than in the retractor blade, or in still other embodiments the evacuation channels may be disposed in both the blade illumination device and the retractor blade. Other embodiments may rely on a gap between the vane and a bottom surface of the blade illumination device to create a plenum that allows smoke evacuation.

Retractor Blade and Handle Engagement

Any number of quick release mechanisms for engaging the retractor blade with the handle may be used. The quick release mechanism, or engagement mechanism should be easy to actuate, and in some embodiments allows one handed actuation for one handed engagement or disengagement of the retractor blade from the handle. The mechanism preferably still permits the handle and retractor blade to be easily cleaned and re-sterilized after use. In still other embodiments, the mechanism along with other parts of the retractor including the handle, retractor blade and illuminator blade are single use disposable. The engagement mechanism preferably allows release of the retractor blade from the handle without requiring that any cables (e.g. light input cables) or tubes (e.g. suction tubes) be disconnected from the handle. Additionally, the mechanism preferably allows the retractor blade to be disengaged from the handle without requiring the blade illuminator to be disconnected from the handle. Several embodiments of quick release mechanisms are disclosed herein for exemplary purposes, and they are not intended to be limiting. Any of the quick release mechanisms described herein may be used with any of the other components or features described herein. For example, any of the quick release mechanisms described herein may be used with any of the handle, retractor blade, illuminator blade, or smoke evacuation embodiments disclosed herein.

Figure 15B:
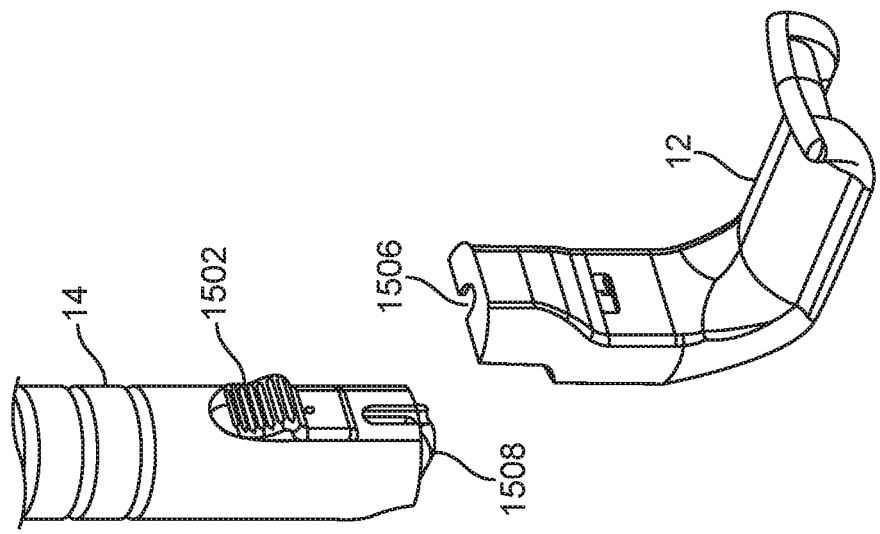
FIGS. 15A-15B illustrate an exemplary embodiment of an engagement mechanism for coupling a retractor blade with a handle.
Figure 15A:
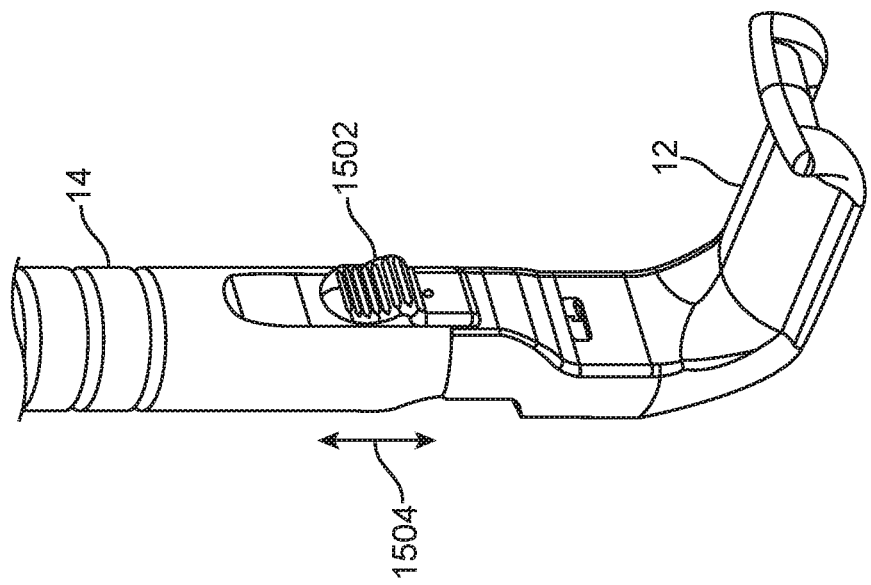

FIGS. 15A-15B illustrate an exemplary embodiment of a quick release mechanism for coupling the handle 14 with the retractor blade 12. In this exemplary embodiment, the quick release mechanism includes an actuator switch 1502 that is slidably actuated as indicated by arrow 1504. The switch 1502 has two positions, an engaged position and a disengaged position. FIG. 15A illustrates the switch in the engaged position wherein the handle 14 is locked with the retractor blade 12. FIG. 15B illustrates the switch in the disengaged position which allows the handle 14 to be released from the retractor blade 12. The actuator mechanism advances and retracts an engagement element 1508 such as a central post having an enlarged head or flanged region that is received in a slot 1506 on the retractor blade 12. When the switch is actuated into the engaged position, the enlarged head is pressed further into the receiving slot 1506 creating a friction fit preventing separation of the two components. Actuating the switch into the disengaged position slightly retracts the head from the receiving slot 1506 relieving the friction fit and allowing separation of the two components. The retractor blade is then released from the handle by advancing the retractor blade in a plane transverse to the handle, and in the direction of the distal end of the retractor blade. One of skill in the art will appreciate that the switch may also work in the opposite direction.

Figure 16A:
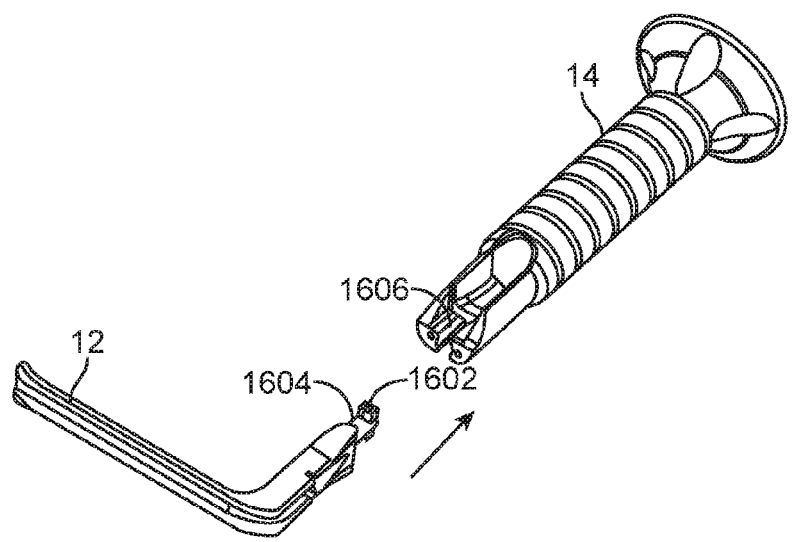
FIGS. 16A-16D illustrate another exemplary embodiment of an engagement mechanism for coupling a retractor blade with a handle.
Figure 16B:
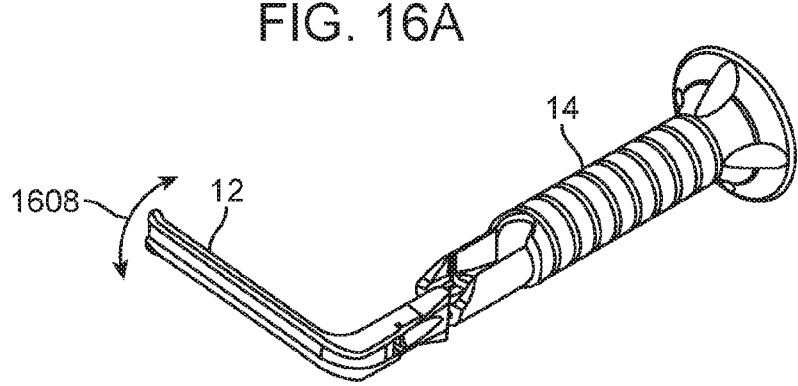
Figure 16C:
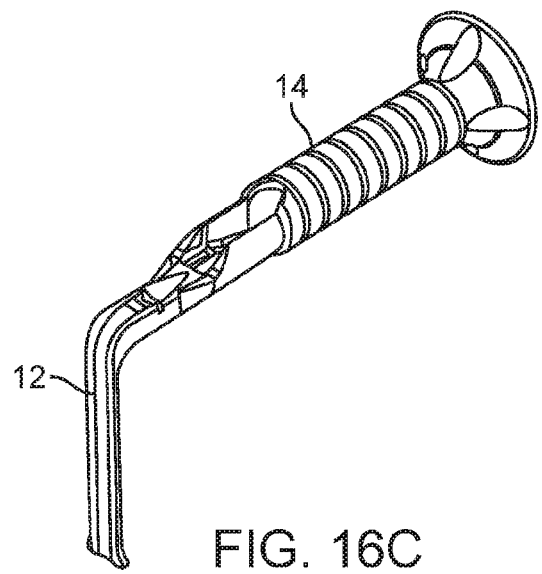
Figure 16D:
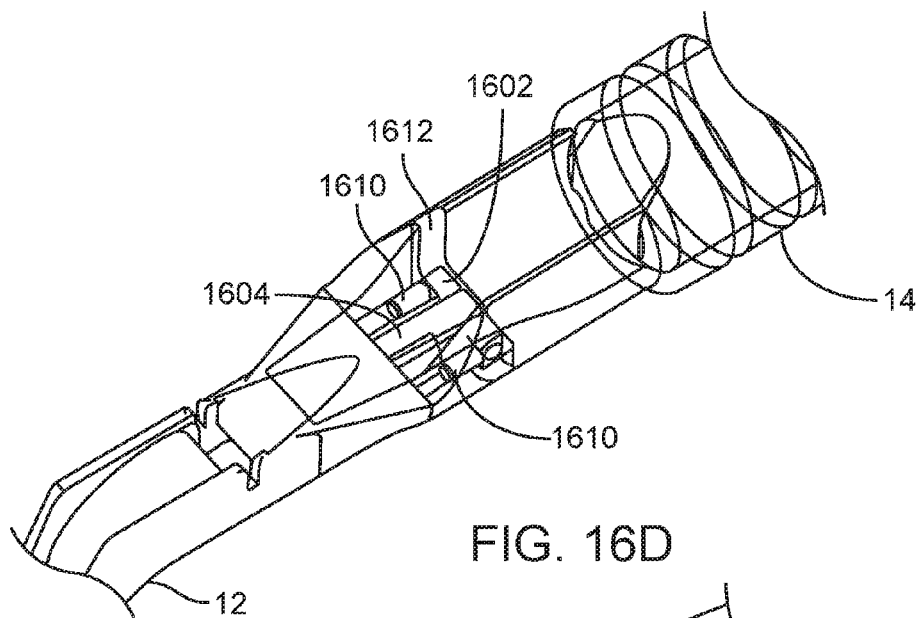

FIGS. 16A-16D illustrate another exemplary embodiment of a quick release mechanism for engaging the handle and retractor blade. FIG. 16A shows the retractor blade 12 disengaged from the handle 14. The engagement mechanism includes a post 1604 having lateral projections forming a T-shaped head 1602 or an enlarged head on the proximal end of the retractor blade. The T-shaped head 1602 is advanced toward a receptacle 1606 with the lateral portions vertically aligned so that the T-shaped head 1602 is received in slot 1606. Once the enlarged head is received in the slot, retractor blade 12 may be rotated 1608 so that the lateral projections of the T-shaped head 1602 become captured in the receptacle 1606. In preferred embodiments, only a quarter turn is required to engage the retractor blade and handle as seen in FIG. 16C. FIG. 16D more clearly illustrates how the lateral projections of the T-shaped head 1602 are captured in slot 1612. Ball detents 1610 disposed on the receptacle press against the lateral projections, thereby holding them in place. Release of the retractor blade from the handle follows the reverse procedure. A quarter turn rotation of the retractor blade relative to the handle releases the lateral projects from the ball detents and disposes them vertically so that the retractor blade may be retracted through the slots in the receptacle and separated from the handle. This embodiment preferably only requires a quarter turn for engagement or disengagement, however other geometries allow more or less rotation of the retractor blade relative to the handle.

Figure 17A:
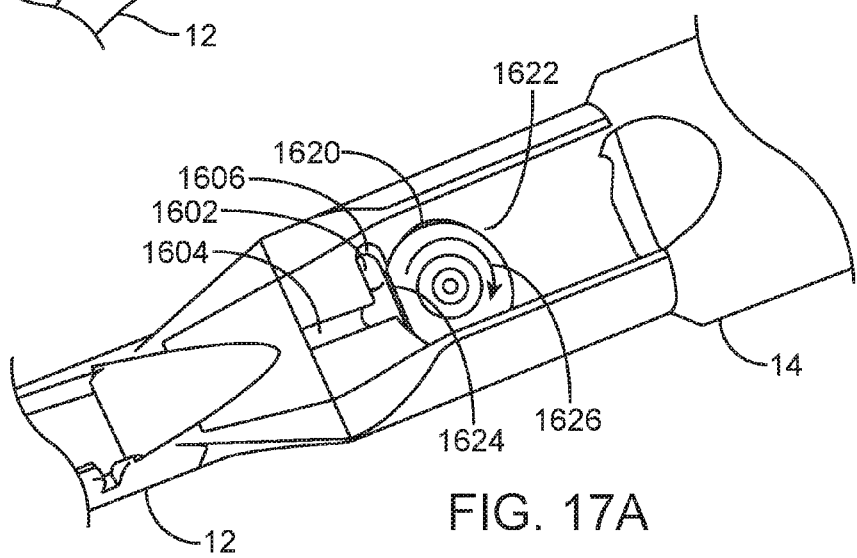
FIGS. 17A-17B illustrate a locking mechanism.
Figure 17B:
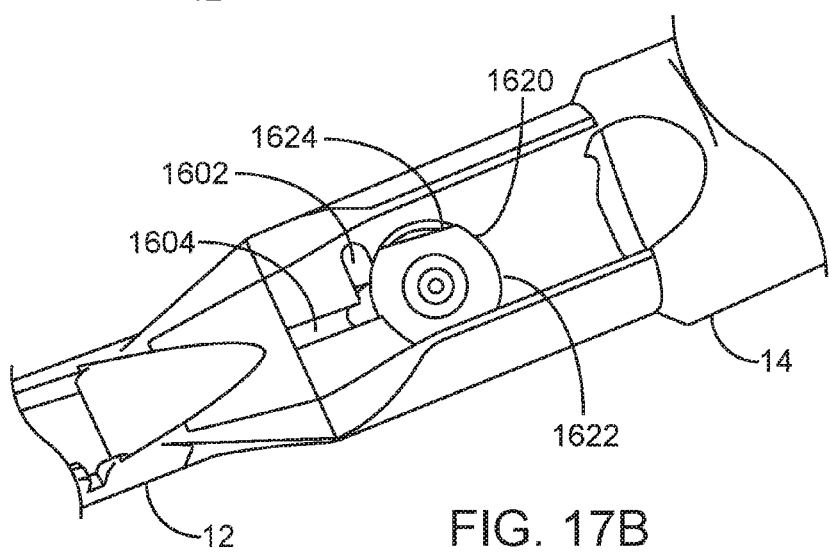

In the embodiment of FIGS. 16A-16D, an optional locking mechanism may also be used to lock the engagement mechanism and prevent inadvertent separation of the retractor blade from the handle. For example, in FIG. 17A a rotating cam 1620 is disposed adjacent the T-shaped head 162 and receptacle 1606. Once the T-shaped head has engaged the receptacle 1606, the cam 1620 may be rotated 1626 to lock the engagement mechanism. The cam has a round portion 1622 and a flat portion 1624. When the flat portion 1624 is adjacent the receptacle 1606 as seen in FIG. 17A, the flat portion does not obstruct the slot and thus the enlarged head may be placed in or removed from the receptacle. However, when the cam is rotated such that the round portion is adjacent the receptacle, the round portion obstructs the slot, thereby preventing the enlarged head from sliding out of the receptacle, thereby ensuring that it is locked. FIG. 17B illustrates the cam in the locked position.

Figure 18A:
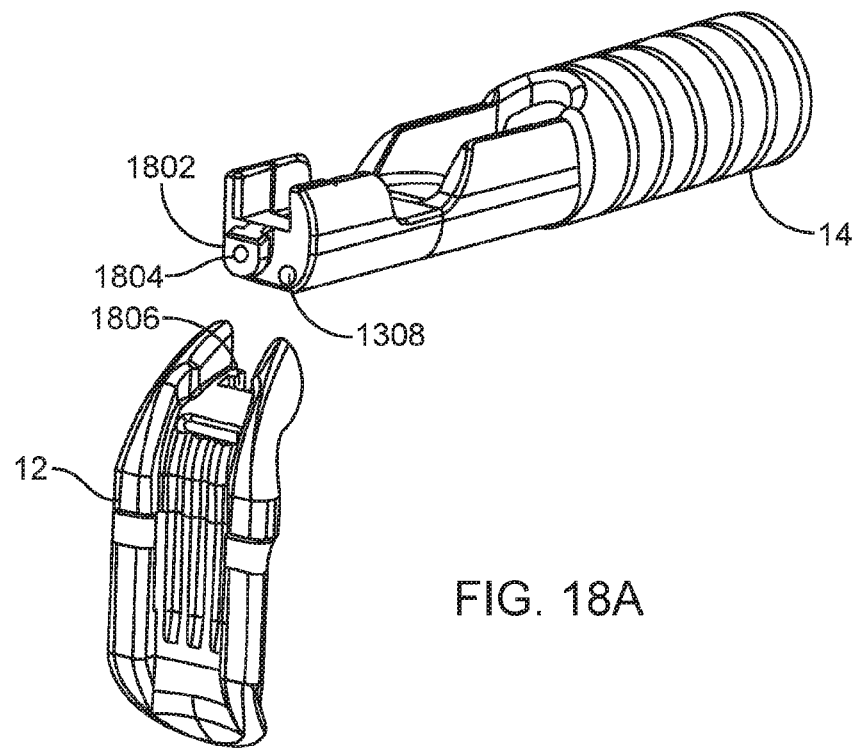
FIGS. 18A-18F illustrate another exemplary embodiment of an engagement mechanism for coupling a retractor blade with a handle.
Figure 18B:
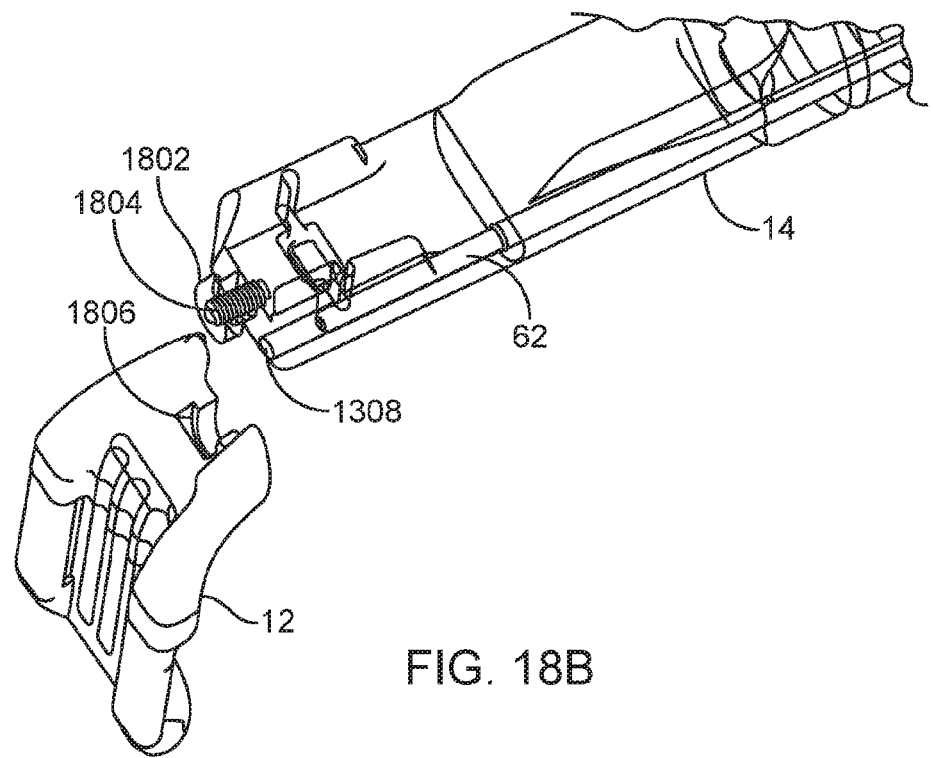
Figure 18C:
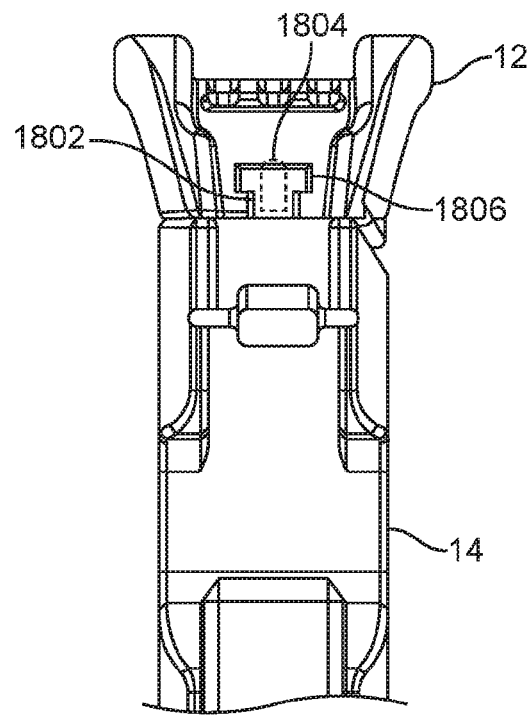
Figure 18D:
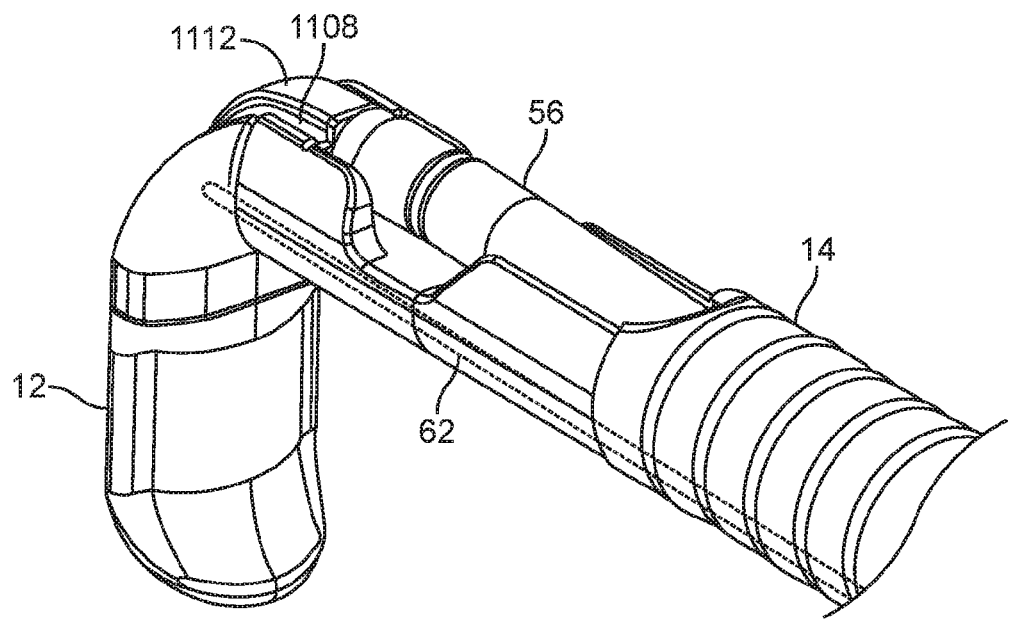
Figure 18E:
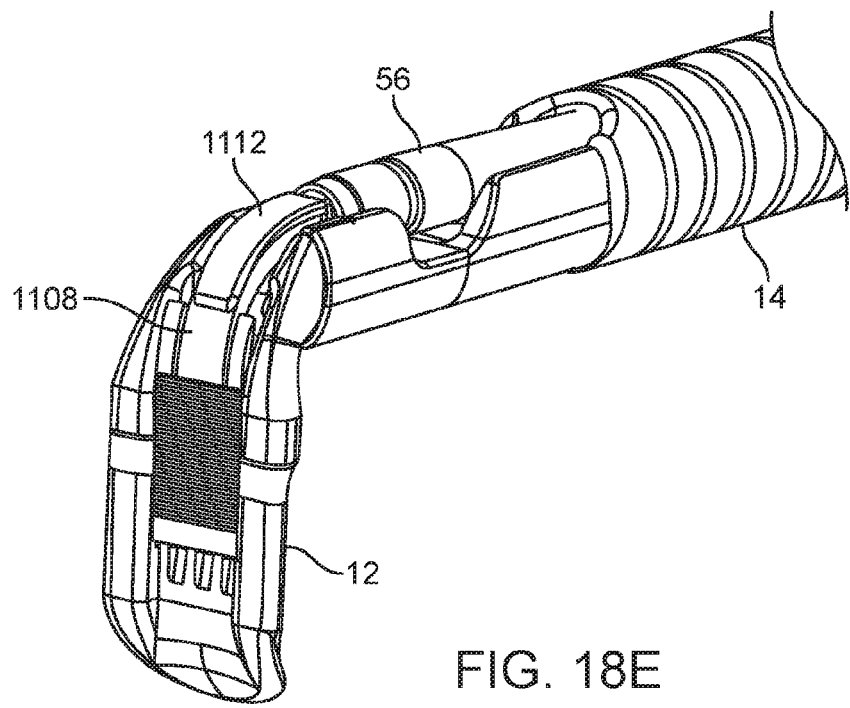
Figure 18F:
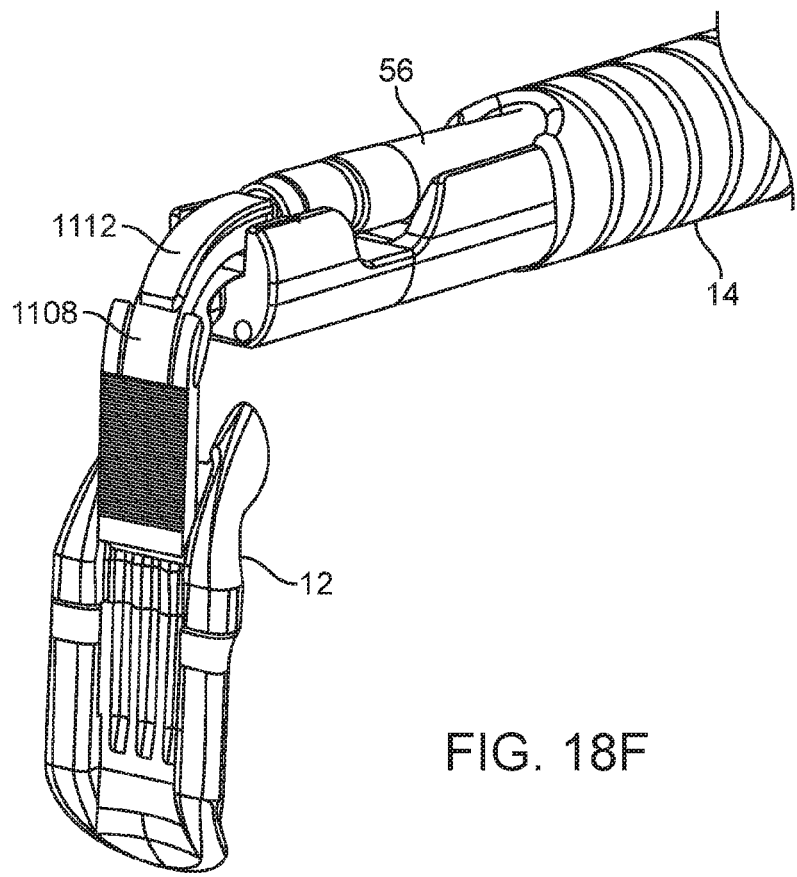

FIGS. 18A-18F illustrate another exemplary embodiment of an engagement mechanism for coupling a retractor blade with a handle. FIG. 18A shows the handle 14 having an engagement element 1802 extending from the distal end of the handle. The engagement element preferably has a central post with an enlarged head or flanged region attached to the central post. A spring loaded ball detent 1804 is disposed on the engagement element 1802. The retractor blade 12 includes a slotted region 1806 that has a geometry that is sized and shaped to receive the central post and enlarged head. A receptacle (not illustrated) in the slotted region 1806 is sized to receive the ball detent 1804. FIG. 18B more clearly illustrates the engagement mechanism. Thus, in operation, the retractor blade is advanced toward the handle and the proximal end of the retractor blade is slidably loaded over the central post and enlarged head so that they are received in the slot on the retractor blade. A slight upward force is applied to the retractor blade so that the ball detent then snaps into its corresponding receptacle, thereby engaging the retractor blade and handle together. The retractor blade in this embodiment is raised in a plane that is transverse to, and preferably substantially parallel to the handle plane for engagement. FIG. 18C illustrates engagement of the handle and retractor blade and also shows the central post 1802 and enlarged head 1804 disposed in the receiving slot 1806. Either before engagement of the retractor blade and handle, or after, the blade illumination device 1108 with or without shield 1112 may be coupled with light input cable 56 and then coupled with the handle 14 and retractor blade 12. Also suction tube 62 may be slidably disposed in the handle and coupled with the retractor blade as previously discussed. The retractor blade may be removed using the reverse procedure. By sliding the retractor blade downward in a plane transverse and preferably substantially perpendicular to the plane of the handle, the ball detent will disengage from its corresponding receptacle, and then the retractor blade may be dropped downward away from the handle and disengaged. Thus, the retractor blade may be disengaged without requiring any cables (e.g. light input cable) or blade illumination devices to be removed. The suction tube 56 helps prevent disengagement of the retractor blade from the handle and therefore must be retracted proximally to disconnect it from the retractor blade. Another advantage of this mechanism as well the others disclosed herein is that the retractor blade can also be removed from the handle without touching the blade illumination device. This mechanism is advantageous because it allows the retractor blade to be separated from the handle easily, without disconnecting cables (such as light input cable 56), nor does the blade illumination device 1108 or shield 1112 need to be uncoupled from the handle, as seen in FIGS. 18E-18F where the retractor blade is released away from the blade illumination device and cable 56.

An alternative embodiment of that in FIGS. 18A-18F includes handle 14 having an engagement element 1802 extending from the distal end of the handle. The engagement element preferably has a central post with an enlarged head or flanged region attached to the central post. It may include spring loaded ball detent 1804 which is disposed on the engagement element 1802. The retractor blade 12 includes a slotted region 1806 that has a geometry that is sized and shaped to receive the central post and enlarged head. A receptacle (not illustrated) in the slotted region 1806 is sized to receive the ball detent 1804. Once the retractor blade is engaged with the handle, suction tube 62 may be slidably advanced into engagement with the retractor blade thereby coupling the handle with the retractor blade and preventing unwanted separation. Removal of the suction tube allows the retractor blade to be separated from the handle in a similar manner as previously described.

Figure 19A:
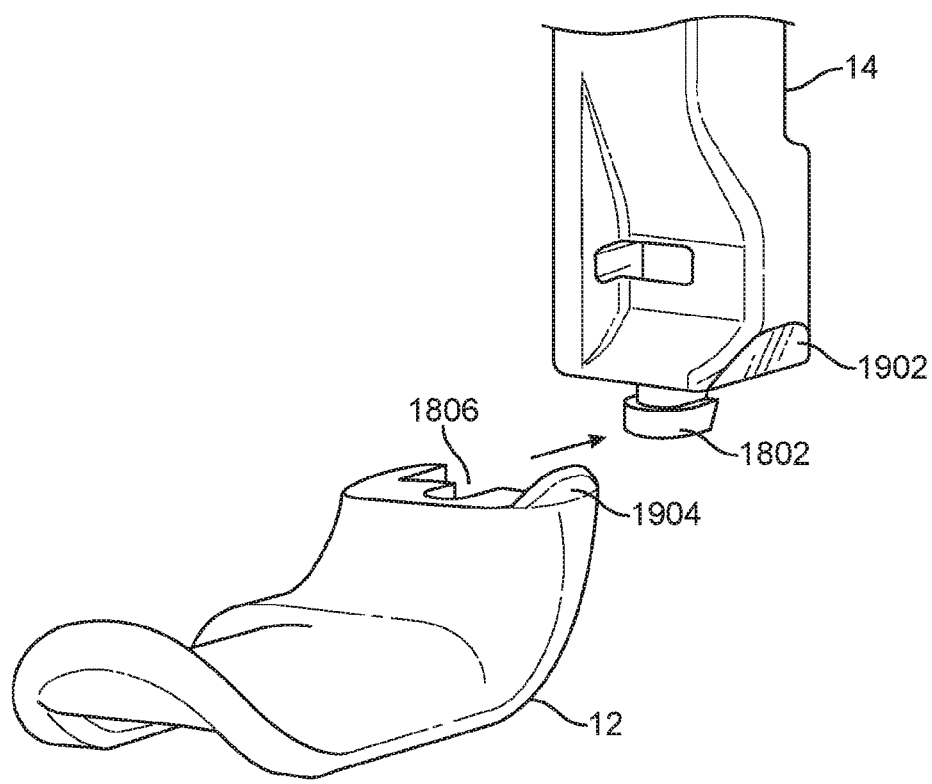
FIGS. 19A-19B illustrate an alignment feature for facilitating engagement of a retractor blade with a handle.
Figure 19B:
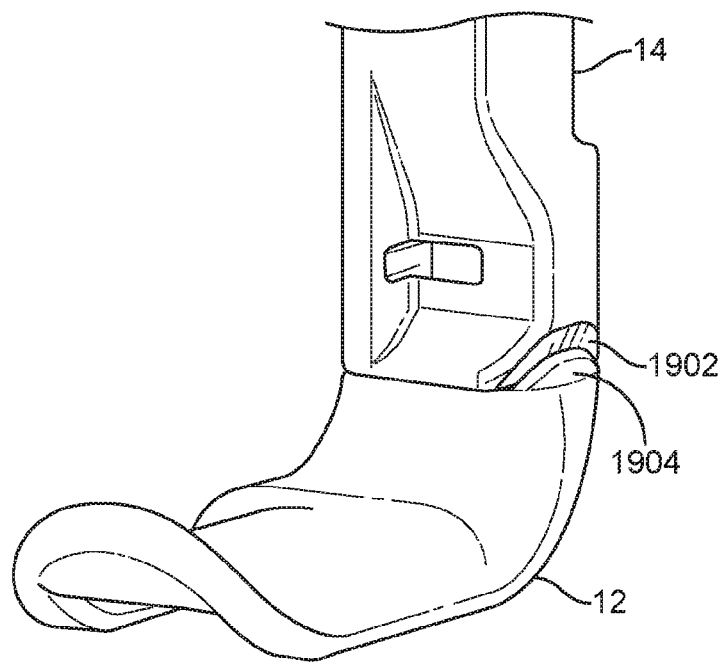

FIGS. 19A-19B illustrate an alignment feature that may be used with the embodiment in FIGS. 18A-18D or with any of the other embodiments disclosed herein. One side of the distal end of the handle 14 may include a rail 1902, and a mating rail 1904 may also be included one side of the proximal end of the corresponding retractor blade 12. Thus, as the retractor blade is advanced toward and engaged with the handle, the two rails 1902, 1904 will contact one another and slide relative to one another. This helps ensure proper alignment of the retractor blade and handle. It also provides a key mechanism that ensures that the retractor blade is inserted in the proper orientation, and not backwards. FIG. 19A shows the retractor blade disengaged from the handle, and FIG. 19B shows the two components engaged, with the alignment rails engaged with one another.

Figure 20:
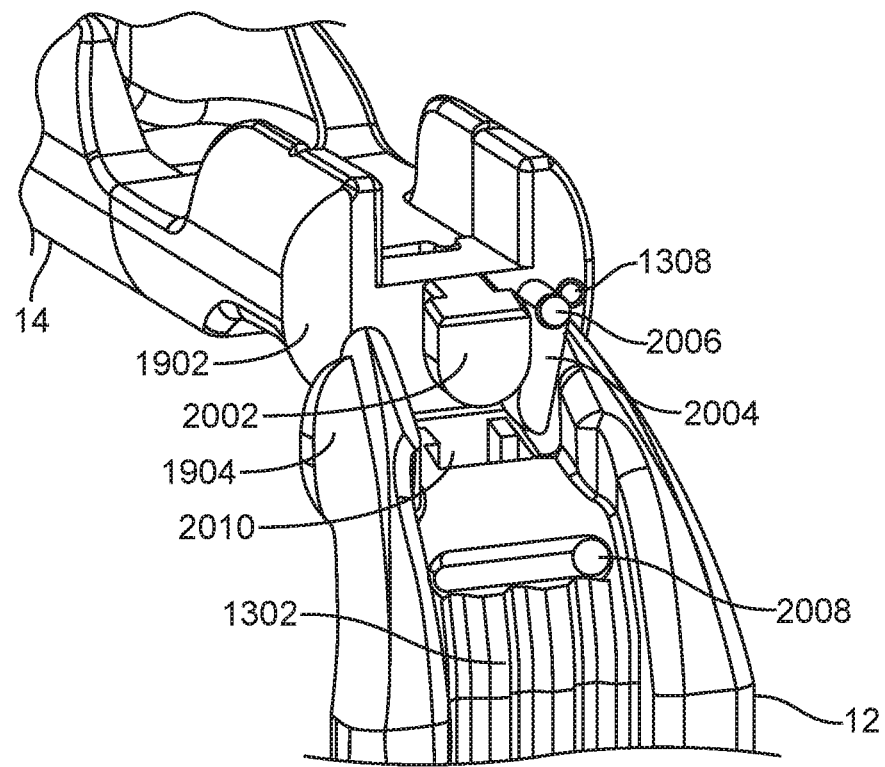
FIG. 20 illustrates still another exemplary embodiment of an engagement mechanism for coupling a retractor blade with a handle.

FIG. 20 illustrates another exemplary embodiment of an engagement mechanism for coupling any of the retractor blades and handles disclosed herein together. Additionally, any of the other features such as blade illumination devices, suction, etc. may also be used with this embodiment. Handle 14 includes an engagement element 2002 extending distally from the distal portion of the handle. The engagement element 2002 includes a central post and an enlarged head or flanged area similar to that described above. A slot 2010 on the proximal end of the retractor blade 12 is sized and shaped to receive the engagement element. Unlike the embodiment described previously, this embodiment does not have a spring loaded ball detent on the engagement mechanism, but alternative embodiments may include it. A rotatable lever 2004 is coupled to the distal end of the handle, and a spring loaded ball detent is included on a portion of the lever. Other features such as the smoke evacuation channels 1302, alignment rails 1902, 1904, vacuum port 1308 generally take the same form as previously described. FIG. 20 also illustrates an aperture 2008 in the retractor blade which is aligned with vacuum portion 1308 when assembled so that the channels 1302 are fluidly coupled with the vacuum. In use, the retractor blade may be raised into engagement with the handle such that the alignment element 2002 is received in slot 2010. The lever 2004 is then rotated from an unlocked position (pointing down in this embodiment) to a locked position (rotated outward) to lock the retractor blade into engagement with the handle. The ball detent 2006 snaps into a receptacle (not illustrated) on the retractor blade and provides adequate force to prevent accidental disengagement of the lever. Additional details on the engagement mechanism are disclosed in greater detail below.

Figure 21A:
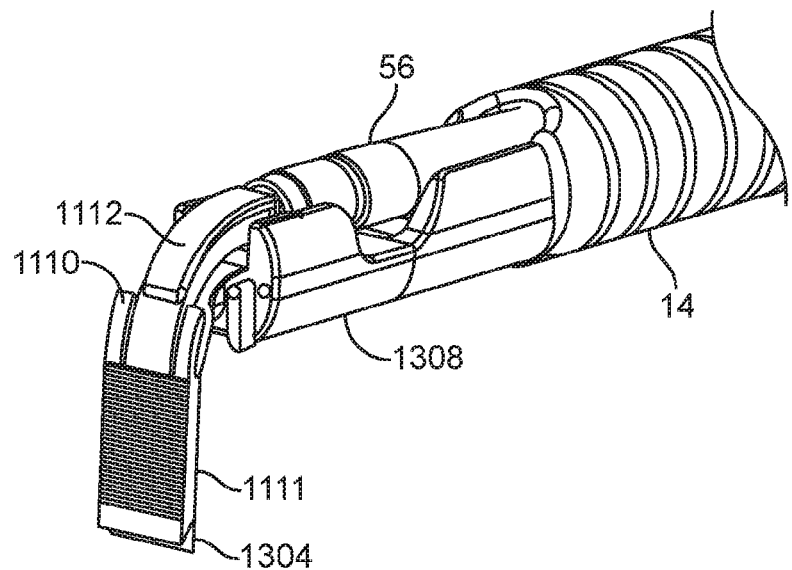
FIGS. 21A-21C illustrate coupling of a retractor blade with a handle using the engagement mechanism in FIG. 20.
Figure 21B:
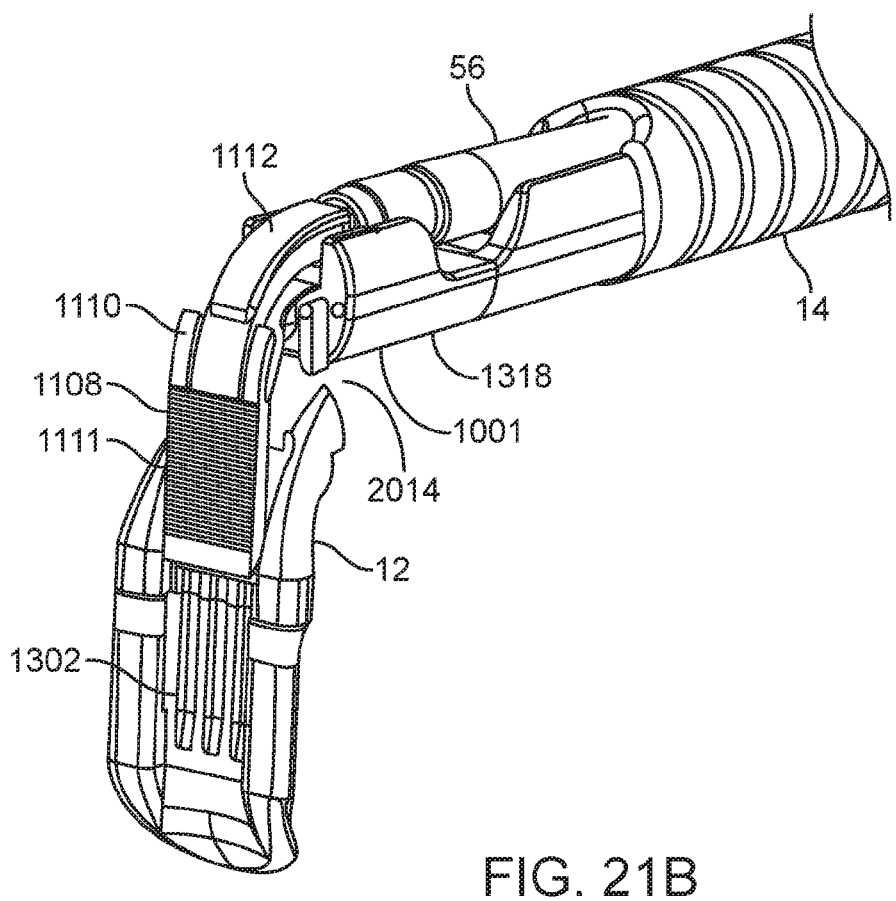
Figure 21C:
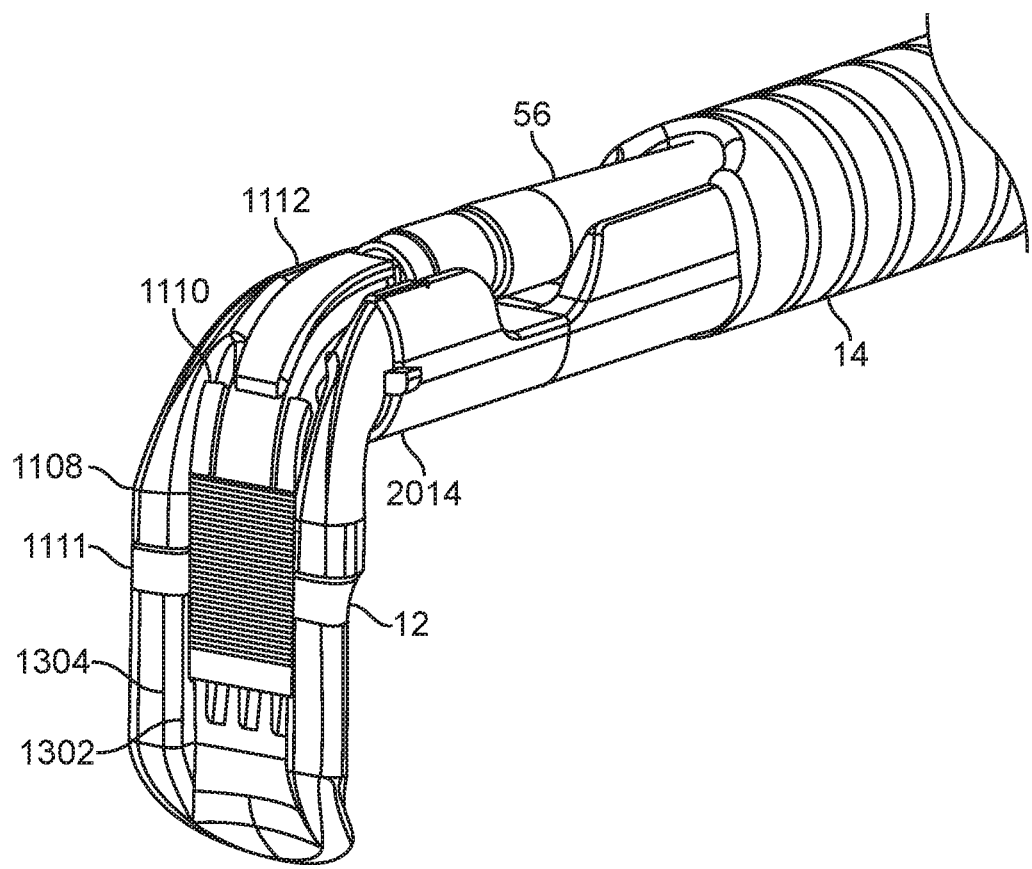

The engagement mechanism of FIG. 20 allows a retractor blade to be coupled with the handle either before or after a blade illumination device has been coupled with the handle. The engagement mechanism allows the attachment and detachment of the retractor blade without requiring the operator to touch the blade illumination device, and cables such as the light input cable need not be disconnected. FIGS. 21A-21C illustrate an embodiment where the blade illumination device is coupled with the handle before the retractor blade is coupled with the handle. In FIG. 21A, the blade illumination device 1108 is attached to the handle 14 and light input cable 56 is also optically coupled with the blade illumination device. The blade illumination device generally takes the same form as the embodiment in FIG. 12A-12E, and may be attached to the handle in the same manner as described above in FIGS. 11A-11E. The embodiment in FIG. 21A also includes vane 1304 attached to a portion of shield 1112. The vane 1304 may be any of the embodiments of previously described above and used to create a plenum for smoke evacuation. The lever 2004 is in the disengaged position, and then the retractor blade 12 is advanced toward the handle as illustrated in FIG. 21B. The blade illumination device 1108 and vane 1304 are slidably disposed in a central channel of the retractor blade, and the retractor blade is raised vertically relative to the handle. The retractor blade is raised in a plane transverse to the plane of the handle, and preferably substantially perpendicular to the handle. Once the retractor blade is aligned with the handle and the blade illumination device is properly disposed adjacent the retractor blade, the lever 2004 may be rotated into the engaged position as seen in FIG. 21C thereby locking the retractor blade with the handle.

Figure 22A:
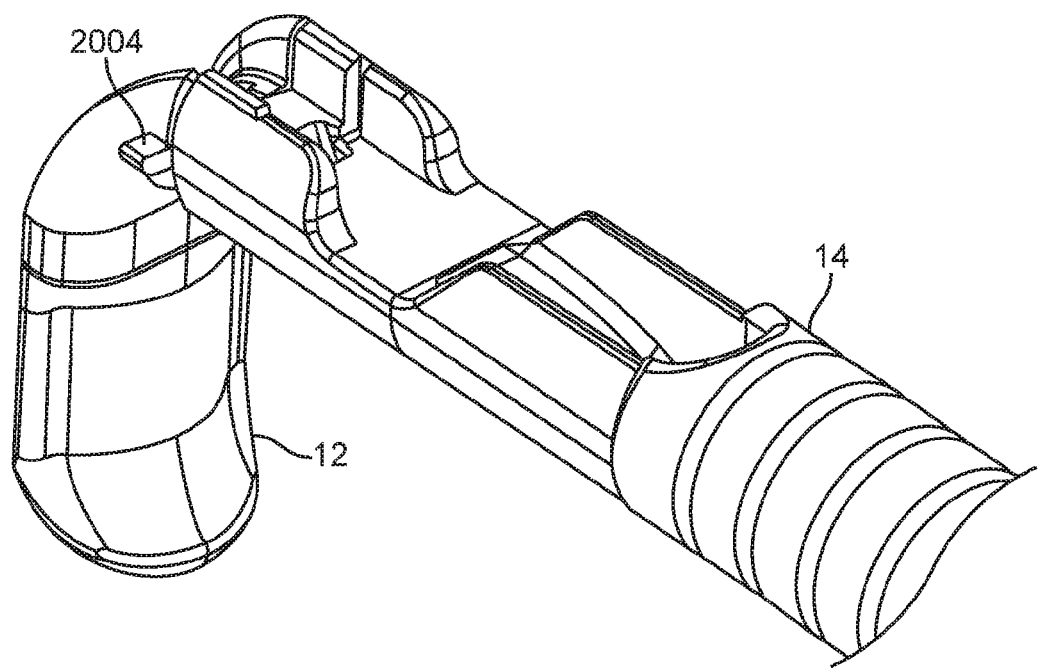
FIGS. 22A-22B illustrate another exemplary method of coupling a retractor blade and handle together using the engagement mechanism of FIG. 20.
Figure 22B:
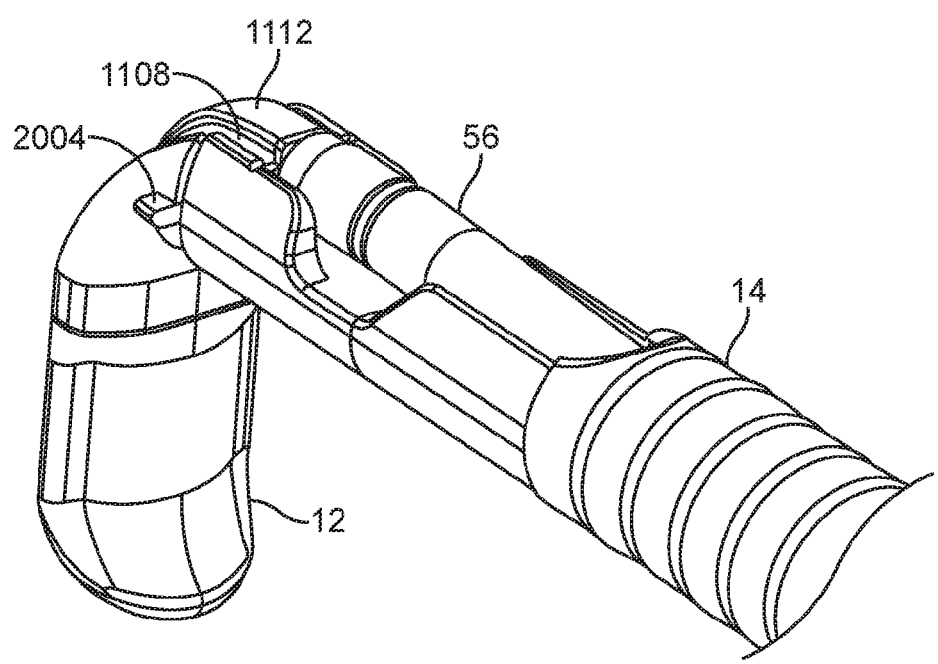

In alternative embodiments, the retractor blade may be attached to the handle first, then the blade illumination device may be coupled with the handle as seen in FIGS. 22A-22B. In FIG. 22A, retractor blade 12 is engaged with handle 14 and the lever 2004 is rotated into the locked position, similarly as described above. The blade illumination device 1108 with shield 1112 is then coupled with the handle and disposed against the retractor blade. Cable 56 then optically couples the blade illumination device 1108 with a light source.

Figure 23A:
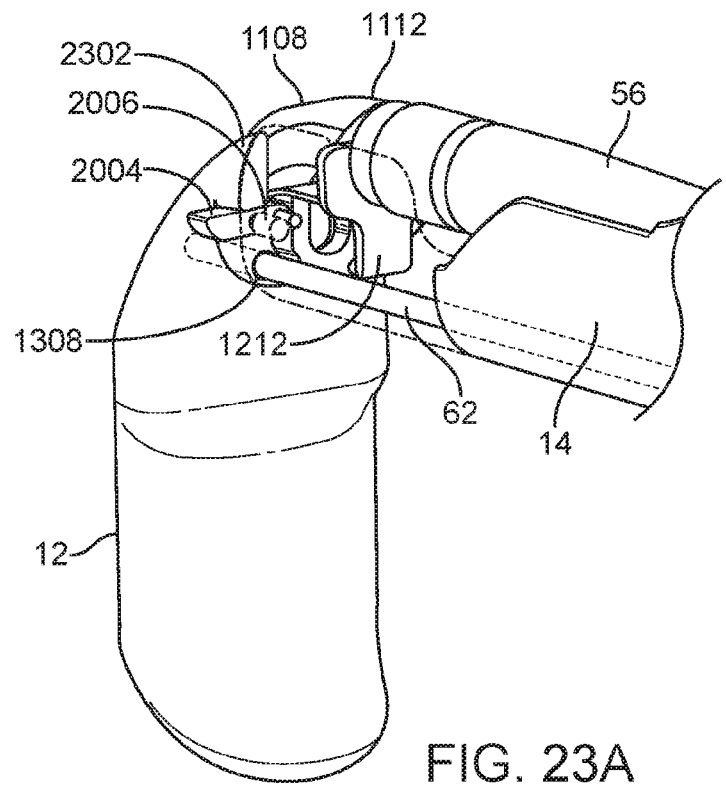
FIGS. 23A-23E illustrate disengagement and re-engagement of a retractor blade with a handle using the mechanism of FIG. 20.
Figure 23B:
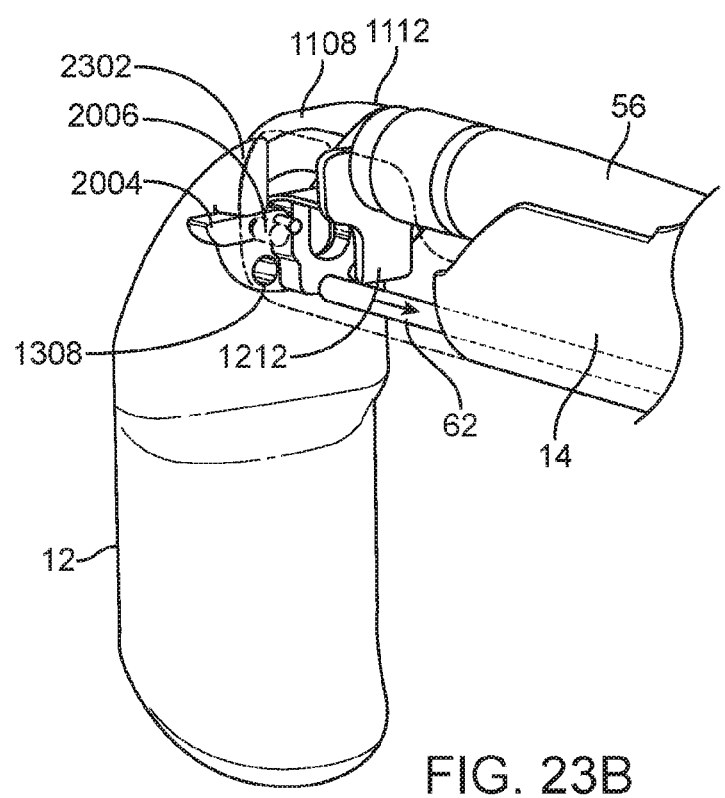
Figure 23C:
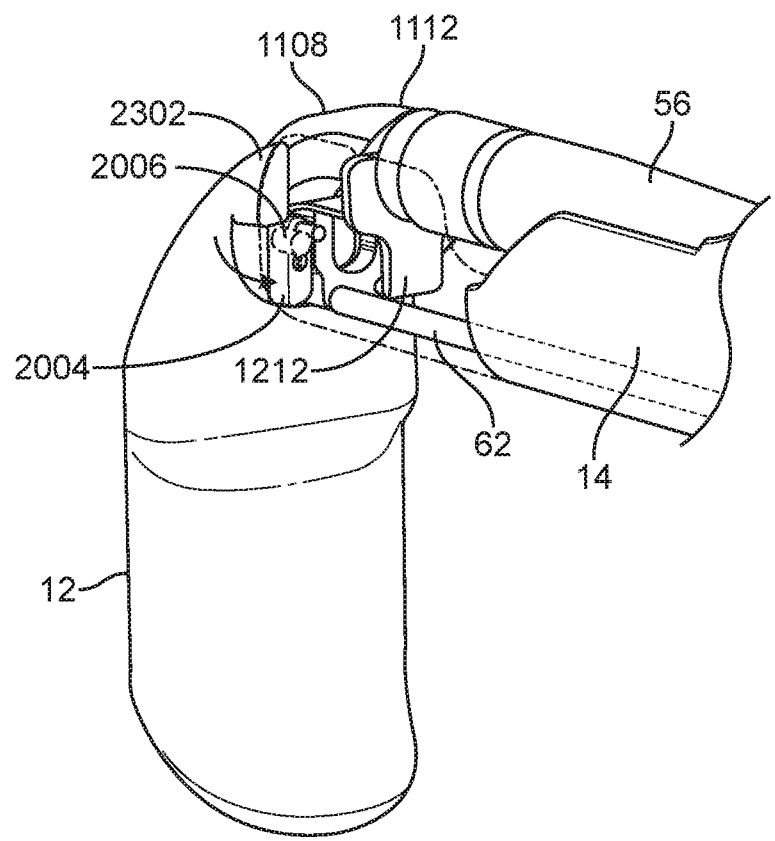
Figure 23D:
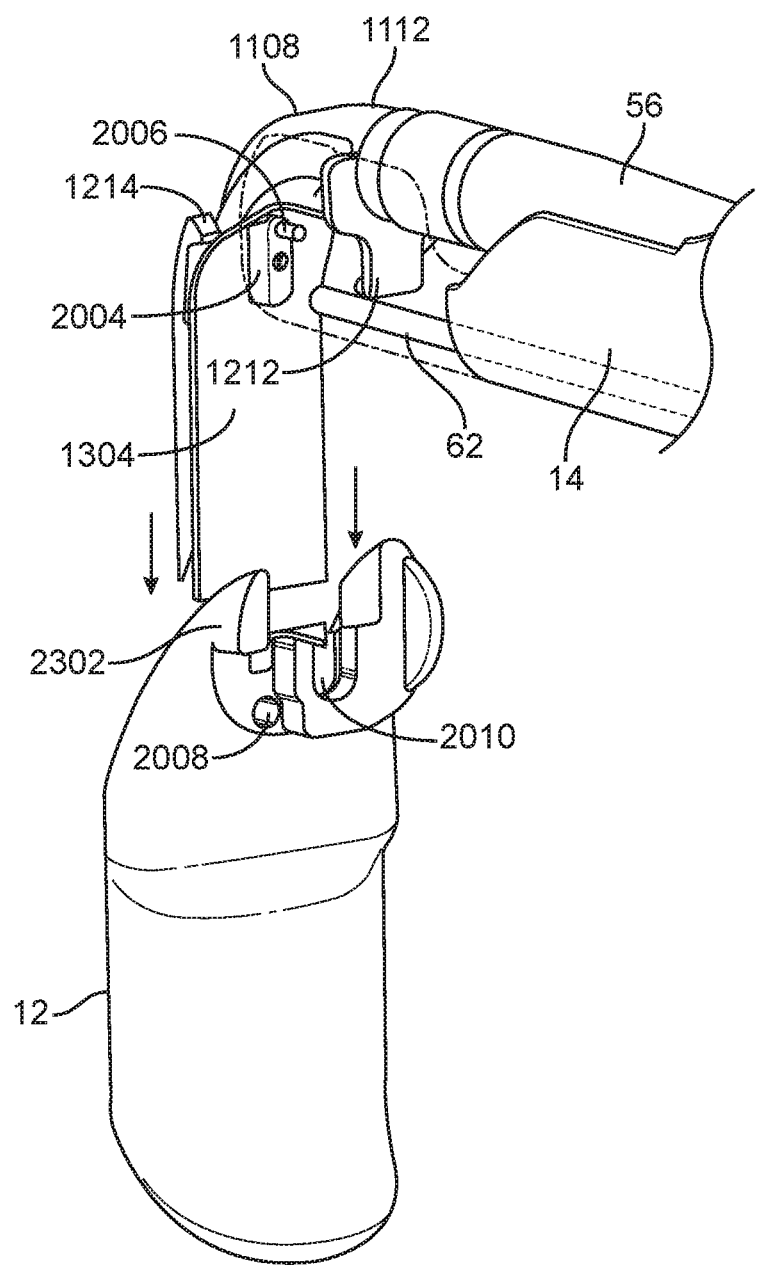
Figure 23E:
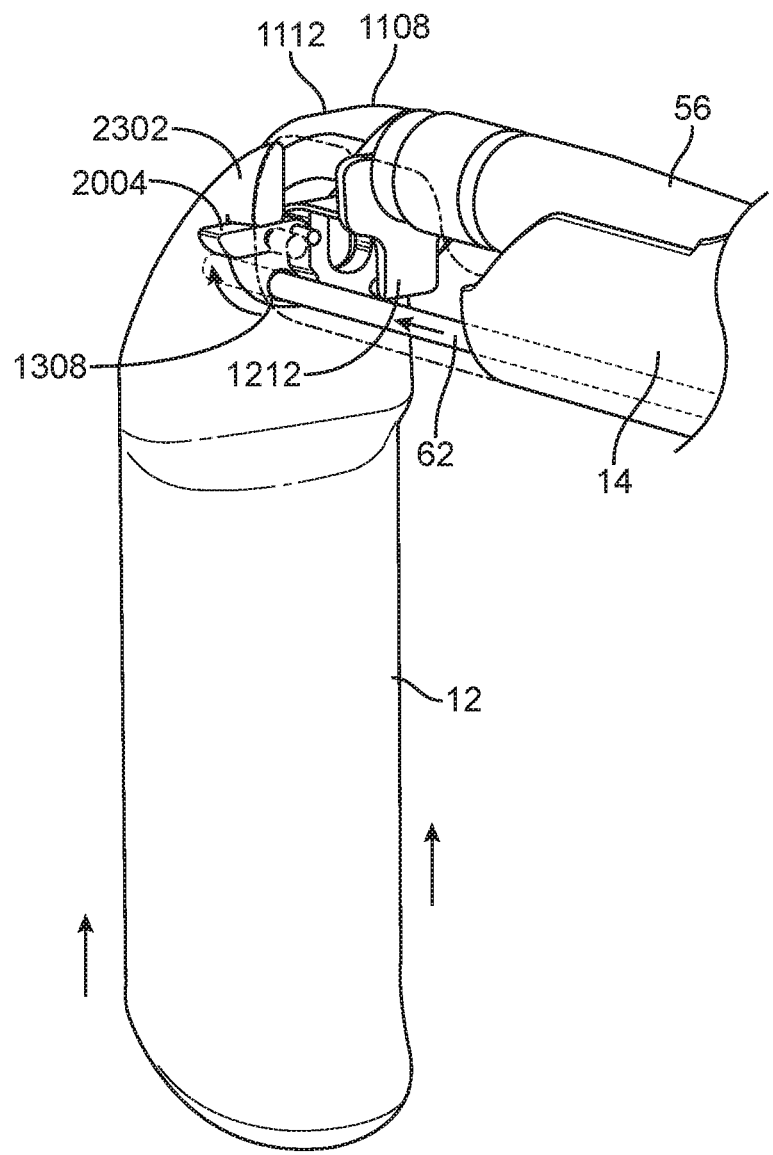

FIGS. 23A-23E illustrate more clearly how the mechanism in FIG. 20 allows quick release of a retractor blade with a handle. In FIG. 23A, retractor blade 12 is already engaged with handle 14. Lever 2004 is in the engaged position which forms a horizontal surface against which shoulder 2302 rests, preventing the retractor blade from slidably disengaging from the handle. The blade illumination device 1108 with shield 1112 is snapped into the handle and disposed against the retractor blade. Cable 56 optically couples the blade illuminator device with the retractor blade. Suction tube 62 is in fluid communication with the retractor blade via aperture 1308 to allow smoke or fumes to be evacuated from the surgical field. Suction tube 62 prevents the rotation of the lever thereby locking the lever into the engaged position. When the operator desires to change the retractor blade, the suction tube 62 is proximally retracted as seen in FIG. 23B so that it is released from aperture 1308. Engagement lever 2004 is then rotated in FIG. 23C into the release position, here rotated counter clockwise into a six o'clock position so that the lever is no longer engaged with shoulder 2302 of the retractor blade. The lever is also out of the path of the shoulder 2302 so that retractor blade slides downward away from the handle 14, and the engagement element 2002 is released from slot 2010. The retractor blade is disengaged in a plane transverse to the plane of the handle, and preferably substantially parallel thereto. This is also in a distal direction toward the distal end of the retractor blade. Light from the illumination blade device is also extracted and directed in this direction. The retractor blade may be disengaged from the handle without touching the blade illumination device 1108 and without requiring cables such as light input cable 56 to be disconnected from the blade illumination device. Also, the blade illumination device 1108 with vane 1304 does not have to be disconnected from the handle during retractor blade change out. FIG. 23D shows disengagement of the retractor blade from the handle with the blade illumination device remaining coupled to the handle. Once the original retractor blade is removed, a second retractor blade may be slid back into position and engaged with the handle as seen in FIG. 23E using the opposite procedure. Once engaged, the lever 2004 may be rotated to lock the retractor blade with the handle by forming a shelf that prevents shoulder 2302 from moving. The suction tube 62 is then re-advanced into apertures 1308 and coupled with the retractor blade. Again, this process is performed without touching the blade illumination device or requiring disconnection of any cables as discussed above, and the blade illumination device may remain coupled to the handle during the engagement.

Figure 32A:
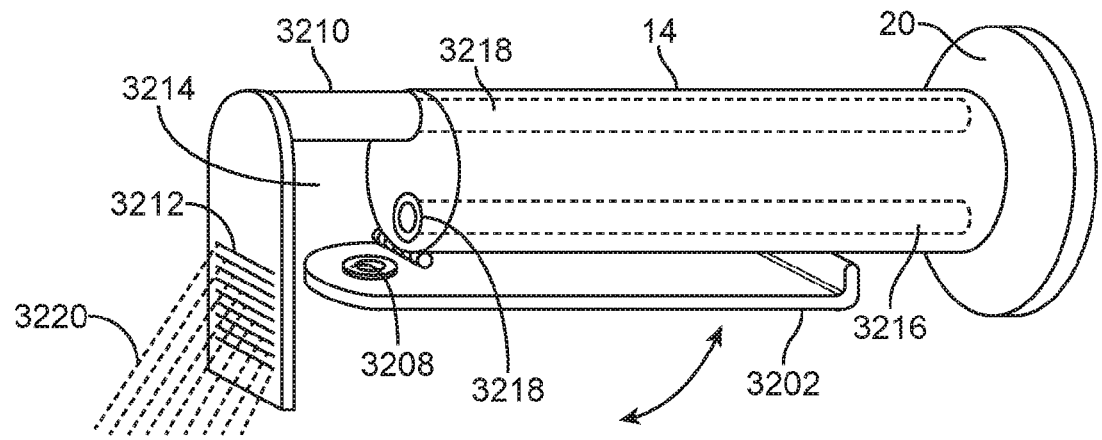
FIGS. 32A-32B illustrate an alternative embodiment of an illuminated retractor with releasable blade.
Figure 32B:
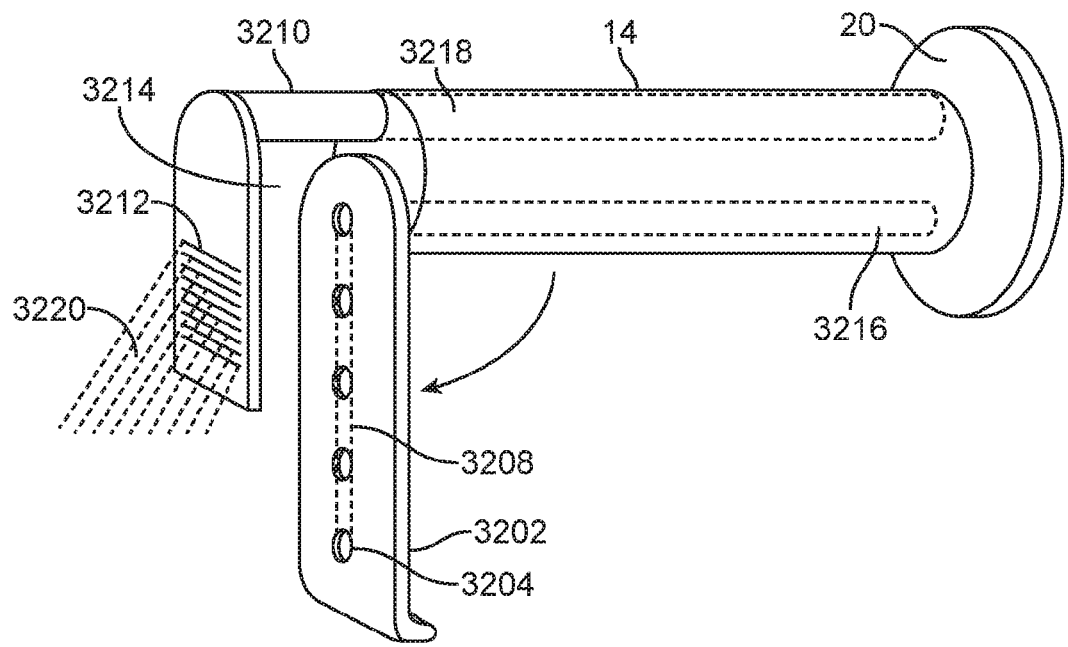

Other engagement mechanisms may be used to releasably couple the retractor blade with the handle. For example, spring clasps with or without latches, sliding prongs, and threaded fasteners may also be used. FIGS. 32A-32B illustrate another exemplary embodiment of an illuminated retractor with a releasably blade. The retractor includes a handle 14, a blade 3202, and a blade illuminator 3210. The handle 14 includes a flanged portion 20 to help the physician retract tissue and channels 3216, 3218 for a suction tube and a fiber optic respectively in the wall of the handle 14. A blade illuminator 3210 is either fixedly or releasably coupled to the handle 14 and optically coupled with a fiber optic cable disposed in channel 3218. The retractor blade 3202 includes a vacuum channel 3206 in the blade and vacuum holes 3204 which allow noxious fumes and smoke to be drawn into the vacuum channel 3206. The retractor blade 3202 is pivotably coupled to the handle 14 so that the retractor blade has a retracted position (seen in FIG. 32A) and an extended position (seen in FIG. 32B). In the retracted position, the retractor blade lies substantially parallel with the handle body 14. When the retractor blade is pivoted outward away from the handle, the retractor blade is extended preferably into a position that is orthogonal to the handle plane where it locks into position with detents or other locking mechanisms well known in the art. Once the retractor blade locks into the extended position, the blade is substantially parallel to the blade illuminator. Additionally a vacuum fitting 3208 on the retractor blade couples with a port 3218 on the handle that is coupled with the suction lumen 3216. Thus, when the retractor blade is extended, the suction automatically is coupled with the handle. Additionally, the retractor blade may retract into engagement with the blade illuminator and the two elements may snap together. In an alternative embodiment, the vacuum channel is an open channel, and the retractor blade sealingly engages the illuminator blade thereby sealing the channel so that suction may be applied to the vacuum holes 3204. Retractor blade fits in the space 3214 created between the blade illuminator and the distal end of the handle. Once the retractor blade is extended, it may be inserted into a surgical field for retraction of tissue. Light 3220 is extracted from the blade illuminator via surface features 3212 and directed toward the surgical field. The retractor blade may also be releasably coupled with the handle so that it may be replaced with a retractor blade having a different configuration. Any of the features of previously embodiments may be combined with or substituted with features of the embodiment in FIGS. 32A-32B. Similarly, features of the embodiment in FIGS. 32A-32B may be used in any of the embodiments disclosed elsewhere in this disclosure.

Figure 33:
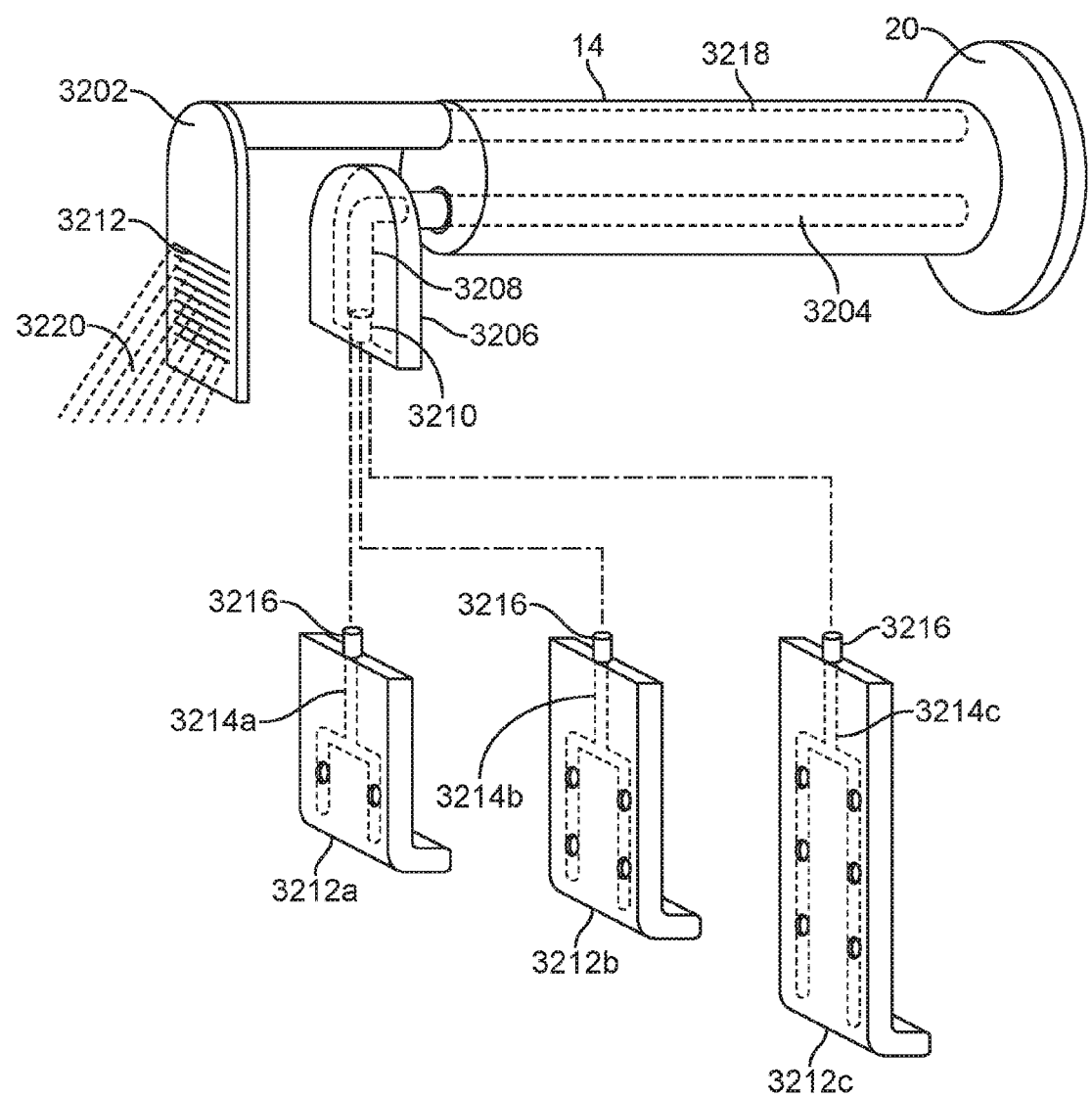
FIG. 33 illustrates another exemplary embodiment of an illuminated retractor with releasable blade.

FIG. 33 illustrates still another exemplary embodiment of an illuminated retractor with a releasable retractor blade. The handle 14 and flange 20 generally take the same form as previous embodiments. A blade illuminator 3202 is also fixedly or releasably coupled to the handle 14 along with a short section 3206 of a retractor blade having a vacuum channel 3208 and a fitting 3210. The short section 3206 may be shorter than, the same length as, or longer than the blade illuminator 3202. Various length and geometry retractor blade extensions 3212a, 3212b, 3212c can then be coupled with the short section 3206 depending on the anatomy being treated. Fittings 3216 on the various retractor blade extensions 3212a, 3212b, 3212c allow the retractor blade to be releasably coupled with fitting 3210 and with the short section 3206 of the retractor blade. The suction lumen 3208 in the short section 3206 may be coupled with the suction lumen 3214a, 3214b, 3214c in the extensions. A suction line in the handle 3204 is coupled with the suction lumen 3208 in the short section and may be coupled to an external source of vacuum. Any of the features of this embodiment may be substituted with or combined with features of any of the other embodiments disclosed herein. Similarly, any of the features in this embodiment may be used in any of the other embodiments disclosed herein.

Surgical Method

Once a preferred retractor blade 12 and handle 14 have been selected and engaged using any of the engagement mechanisms described herein, and preferably a blade illumination device 1108 is coupled to the handle and a light input cable 56 optically couples the blade illumination device with a light source, the retractor may be used to retract tissue, illuminate the surgical field, and evacuate smoke or fumes therefrom as seen in FIGS. 24A-24E.

Figure 24A:
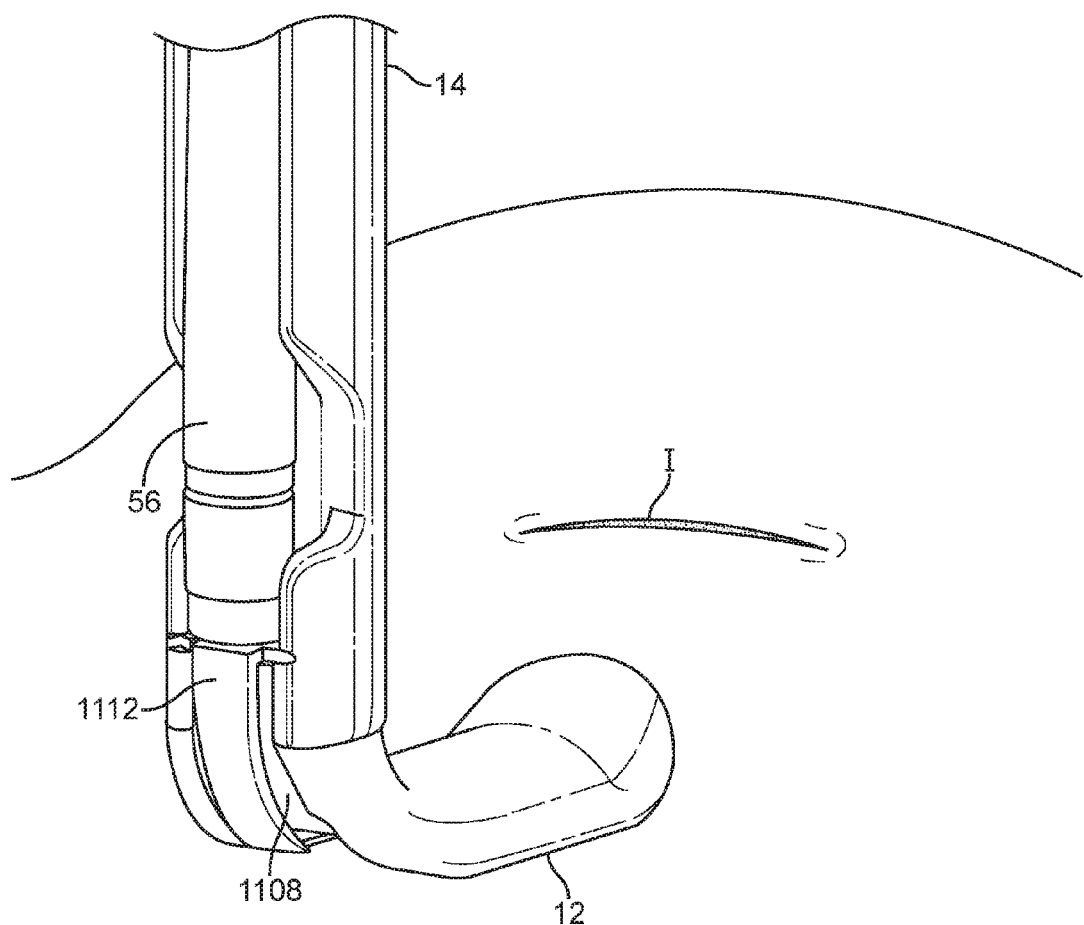
FIGS. 24A-24E illustrate exemplary use of an illuminated surgical retractor to retract tissue, illuminate the surgical field, and evacuate smoke.
Figure 24B:
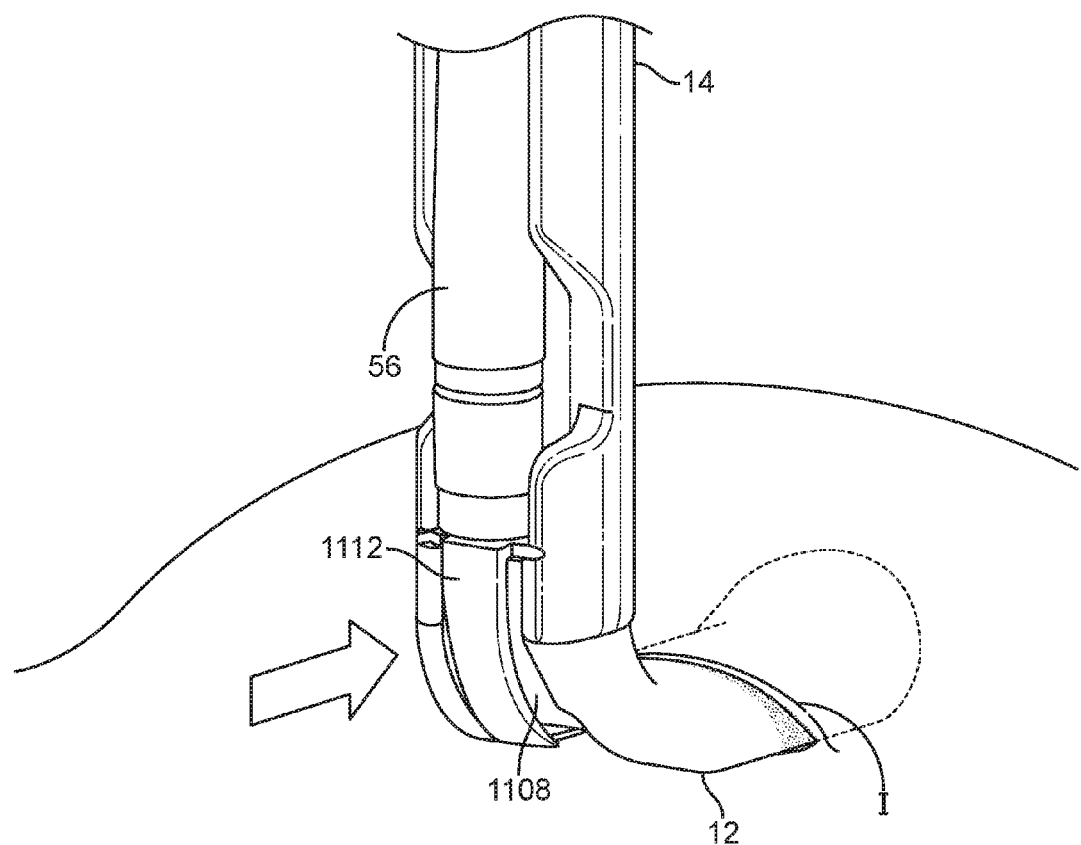
Figure 24C:
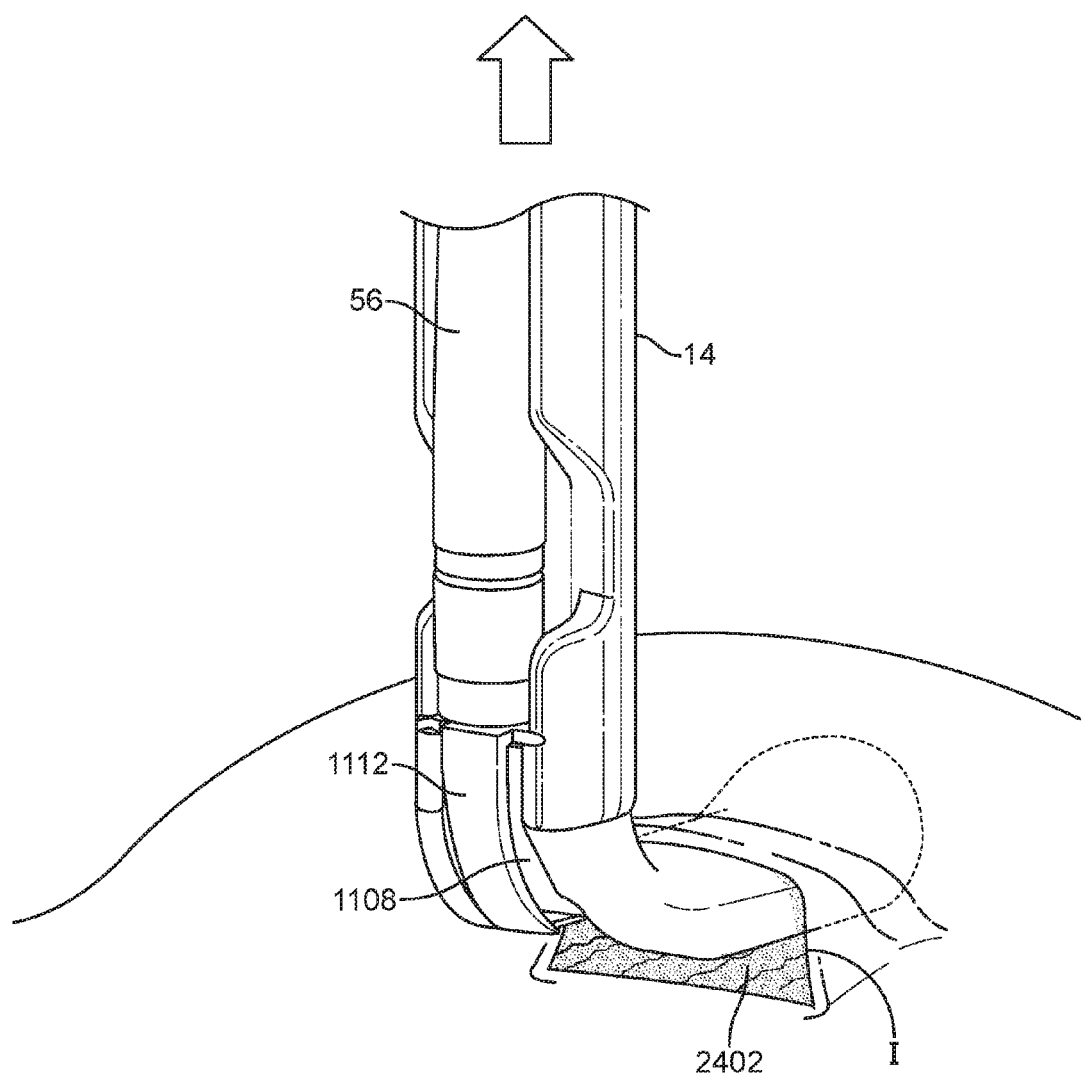
Figure 24D:
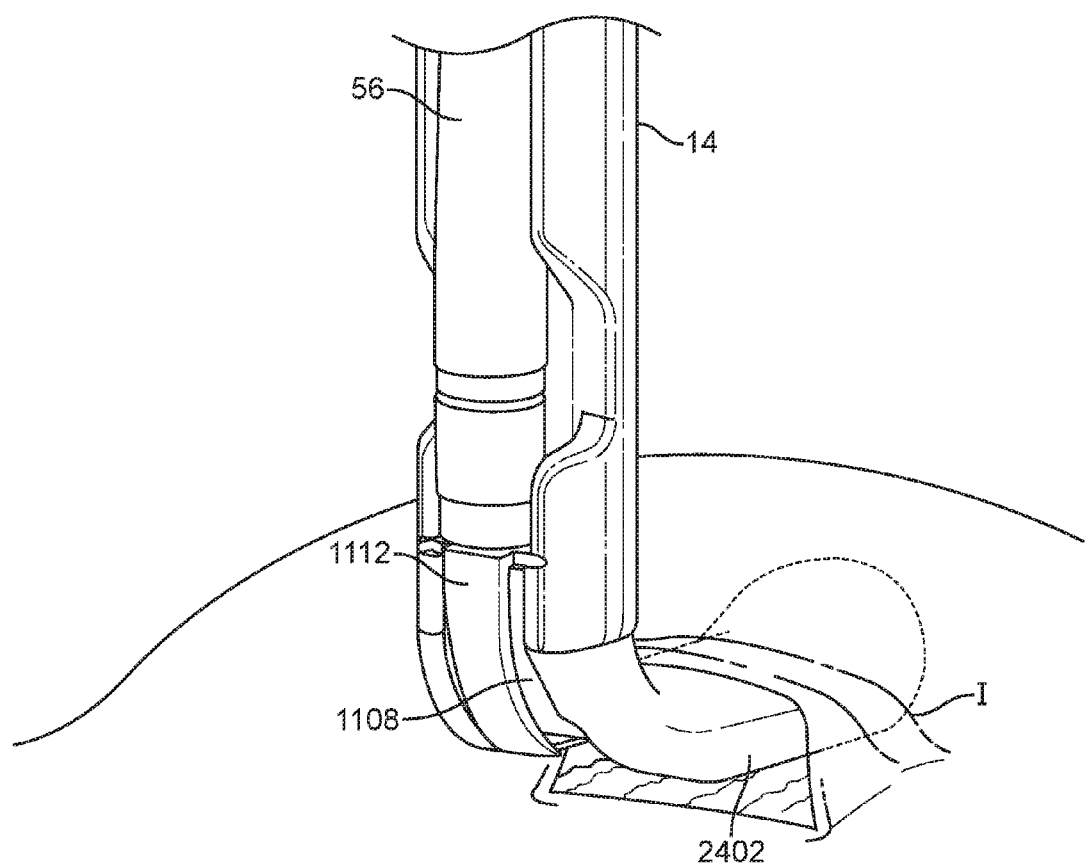
Figure 24E:
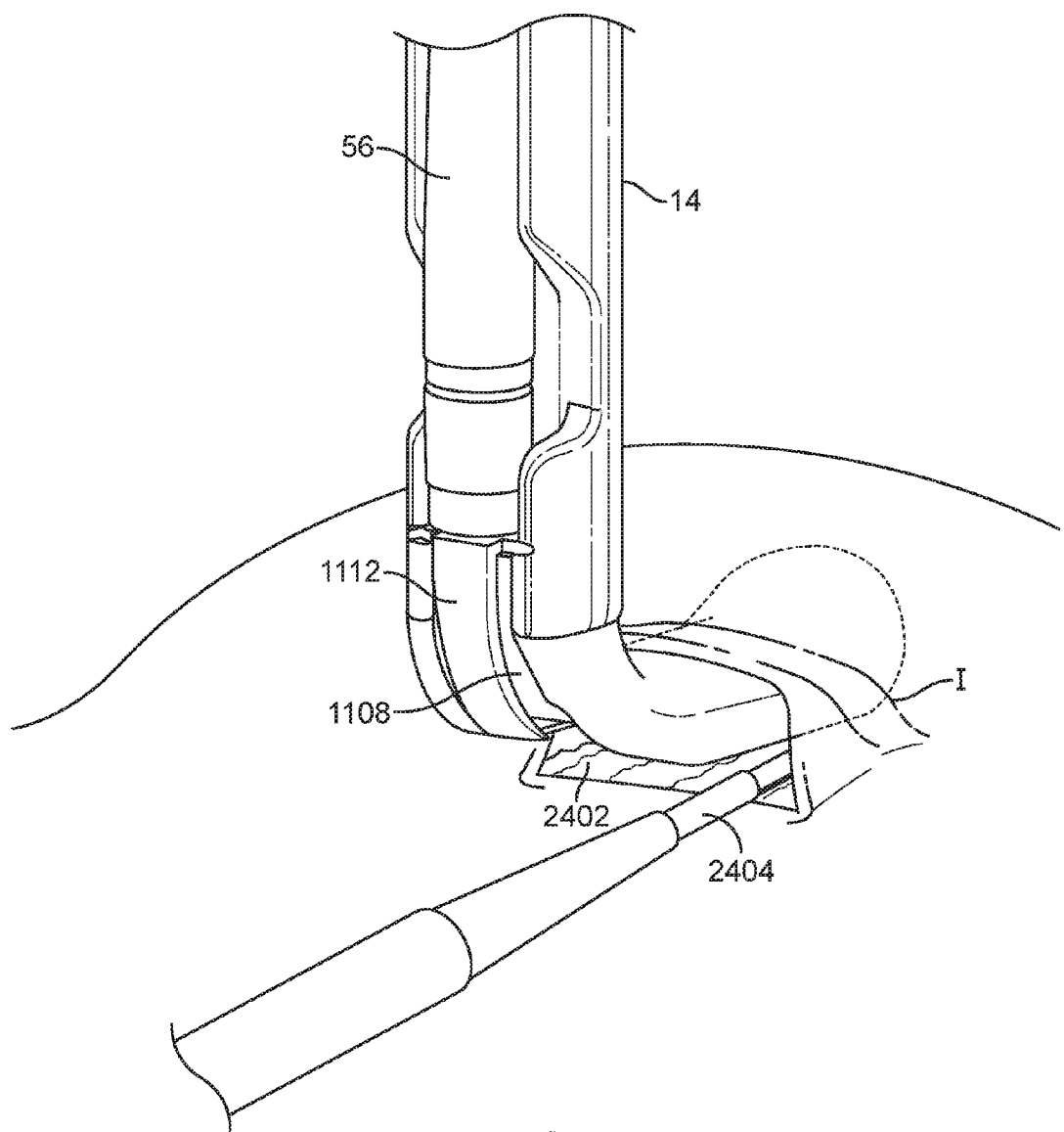

FIG. 24A illustrates the assembled retractor being positioned adjacent an incision I. The retractor may be used to retract any tissue, but preferably is used to retract soft tissue such as in breast or thyroid surgery. In FIG. 24B, the distal tip of the retractor blade is advanced into the incision, and in FIG. 24C, the retractor blade is retracted proximally, here in a vertical direction to retract tissue and create a pocket 2402. Surgical instruments, equipment, as well as the surgeon's hands may be placed in the pocket 2402 to perform diagnostic or therapeutic procedures. Since it will be difficult to see in the pocket, the blade illumination device 1108 is also advanced into the pocket as the retractor blade is inserted into the pocket, thereby illuminating the pocket as seen in FIG. 24D. Additionally, electrosurgical instruments 2404 such as cautery devices may be used during the procedure as seen in FIG. 24E, and this may generate smoke or other noxious fumes which can be evacuated using the smoke features previously described above. The physician may change retractor blades at any time during the procedure in order to accommodate various anatomies, retraction direction, as well as physician position. As mentioned before, any of the features previously described herein may be used in this exemplary method, and thus one of skill in the art will appreciate that any number of combinations or substitutions are possible.

Thyroid Retractor

The surgical retractor embodiments described above are preferably used for retraction of soft tissue during procedures such as breast surgery. The following alternative embodiments are similar to those previously described, but have modifications that are preferable for accommodating soft tissue retraction in other anatomies and procedures, such as during thyroid surgery. The following embodiments may be combined with or substituted with any of the features previously described above. For example, any of the handle, retractor blade or blade adjustment features may easily be incorporated into the embodiments described below. Additionally, the illumination blade features, smoke evacuation, and blade-handle engagement mechanisms may also be used in the embodiments described below. Thus, one of skill in the art will appreciate that any combination of the features described above may be used with or substituted for any of the features described herein. Similarly, any of the features described below may be used with or substituted with the embodiments previously described above.

Figure 25:
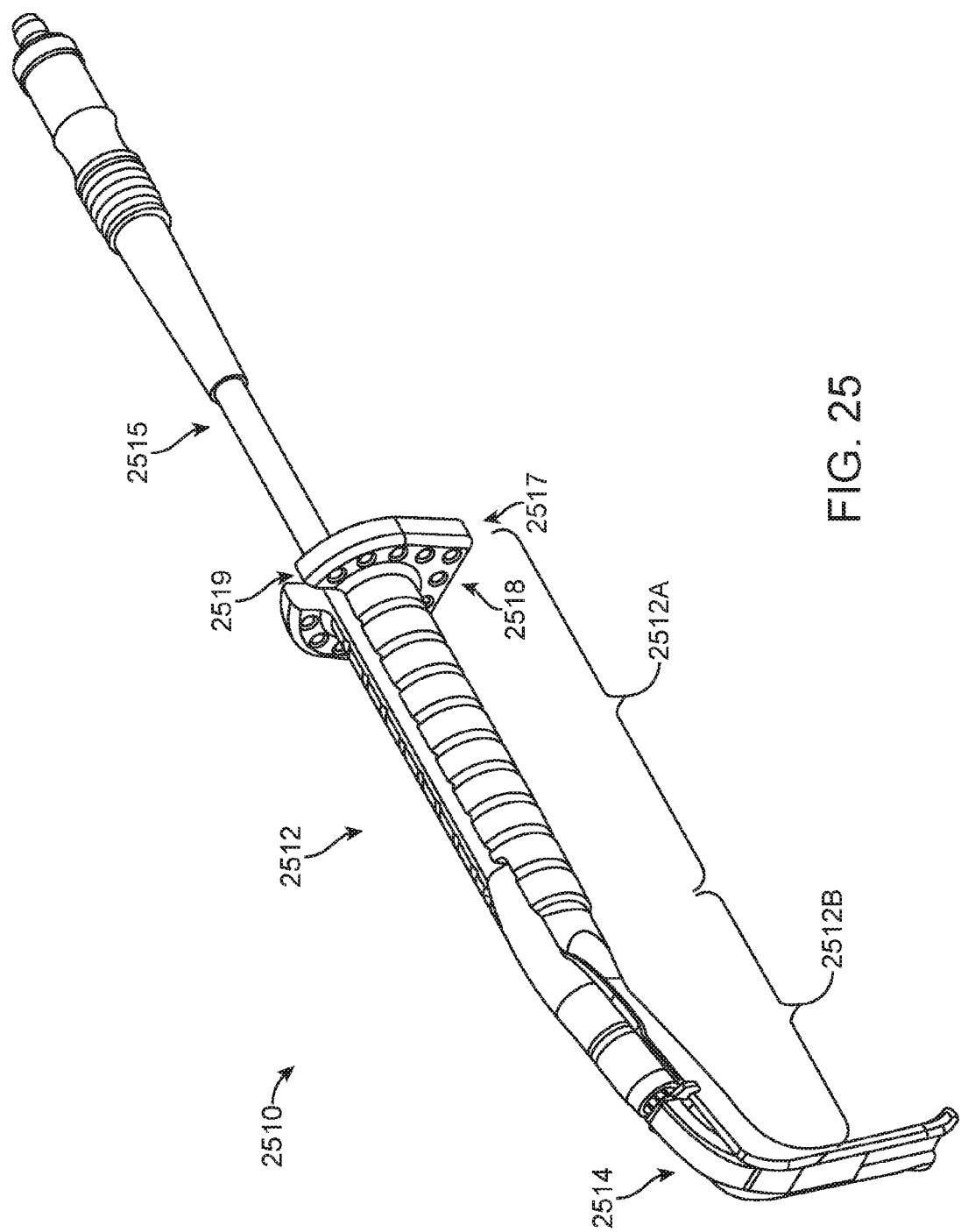
FIG. 25 is a perspective view of another illuminated soft tissue retractor.

Referring to FIG. 25, illuminated soft tissue retractor 2510 includes retractor assembly 2512, illumination waveguide assembly 2514 and illumination assembly 2515. Proximal projection 2517 extends generally perpendicular from retractor body 2512A. Retractor blade 2512B is coupled with a distal portion of the retractor body 2512A and may include a proximal portion that generally lies in the same plane as the retractor body 2512A, and a distal portion which is transverse thereto. In some embodiments, the distal portion of the retractor blade is orthogonal to the proximal portion of the retractor blade, although other angles may be used. Proximal projection 2517 optimizes application of counter traction without the need for squeezing retractor body 2512A which often leads to fatigue. Proximal projection 2517 may be weighted to balance the instrument as well as enabling the retractor to provide counter traction by itself. Proximal projection 2517 may be formed of heavier material than retractor body 2512A or retractor blade 2512B. Alternatively, one or more weights may be secured within proximal projection 2517 such as weights 2516 (best seen in FIG. 28) to control the location of center of mass 2525 as shown in FIG. 28. The weights 2516 maybe releasably connected to the proximal projection 2517 by disposing the weights in a plurality of apertures. The weights may be threadably engaged, press fit, or otherwise coupled with the proximal projection. The apertures may also be machined or otherwise formed into the proximal projection for proper weighting of the assembly.

The configuration of proximal projection 2517 further enables self-retraction by including a generally flat foot or surface 2518 to prevent rolling and sliding of the retractor when it is providing self-retraction. Retractor body 2512A includes channel 2519 to accommodate and engage illumination assembly 2515 within the general profile of retractor body 2512A. The illumination assembly 2515 preferably includes a cable for optically coupling the waveguide assembly 2514 with a light source (not illustrated). A proximal end of the illumination assembly 2515 optically may include a standard optical connector such as an ACMI connector for coupling the cable with the light source.

Figure 26:
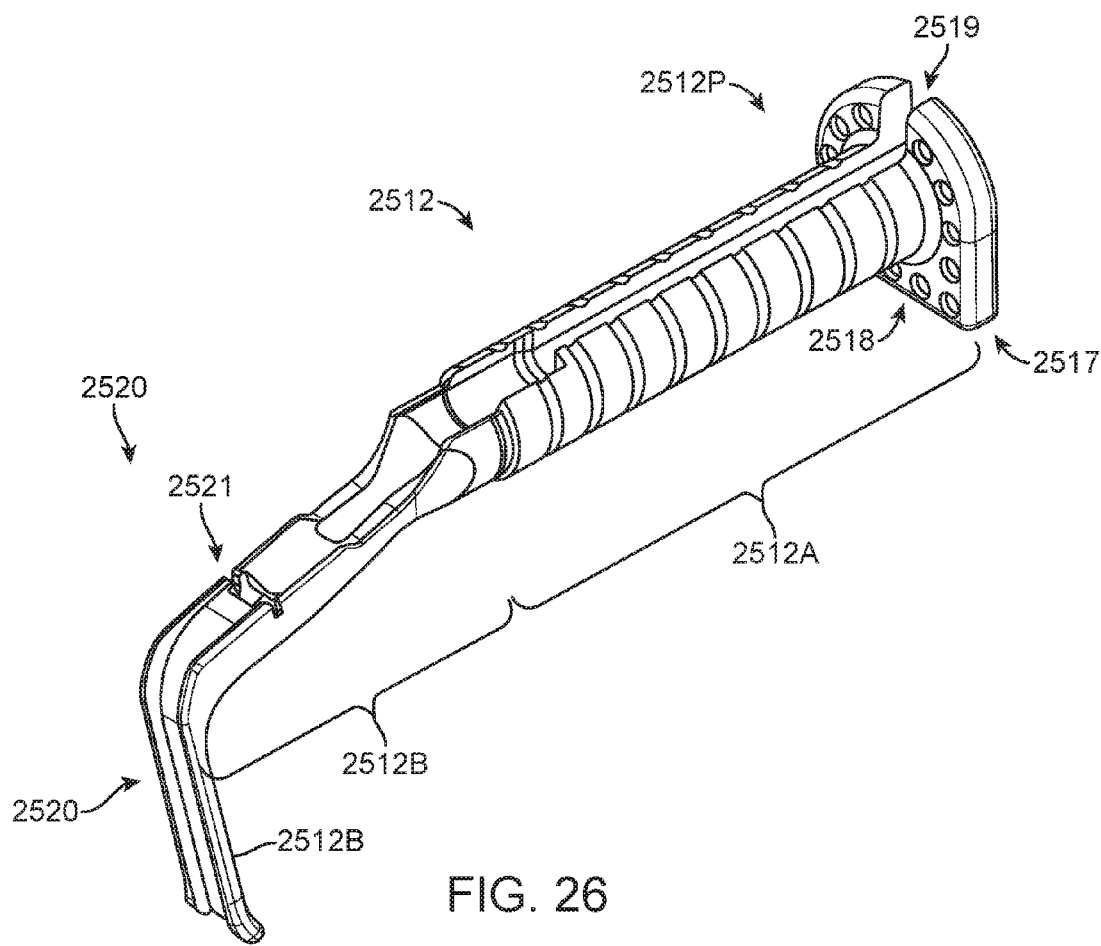
FIG. 26 is a perspective view of the illuminated soft tissue retractor seen in FIG. 25.

Referring now to FIG. 26, retractor assembly 2512 has a distal end 2512D and a proximal end 2512P. Proximal end 2512P includes proximal projection 2517, and distal end 2512D includes retractor blade 2512B. Retractor blade 2512B includes waveguide socket 2520 for engaging illumination waveguide assembly 2514. One of more additional waveguide securing elements may also be included such as clip socket 2521 for further engaging illumination waveguide assembly 2514 and maintaining total internal reflection (TIR) of the light conducted through the waveguide by minimizing contact between retractor blade 2512B and waveguide assembly 2514. When contact between retractor blade 2512B and waveguide assembly 2514 cannot be eliminated, transmission efficiency is maintained by controlling where contact is made and minimizing the possibility of light escaping at the point(s) of contact. The waveguide may have active zones where light is transmitted through the waveguide by total internal reflection, and dead zones where substantially no light is transmitted by total internal reflection. Contact between the waveguide and the retractor blade is preferably limited to the dead zones of the waveguide in order to minimize light loss. Additionally, in preferred embodiments, an air gap is maintained between the active zones of the waveguide and the retractor blade, again to minimize light loss.

Figure 27:
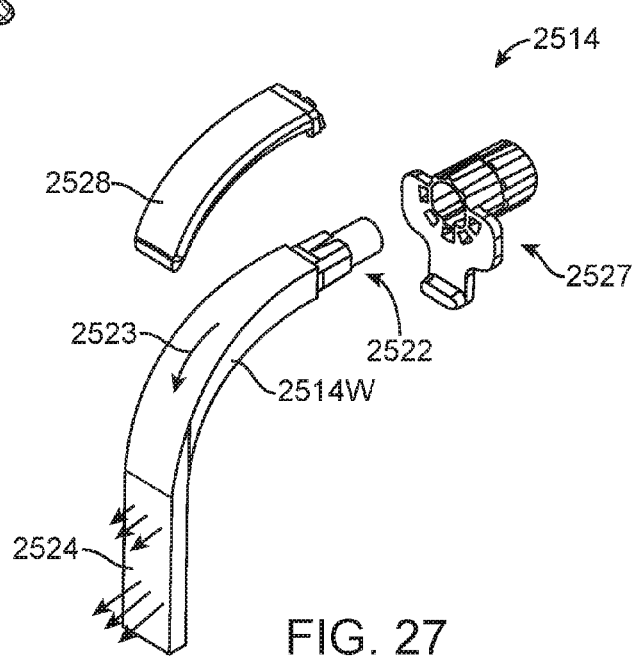
FIG. 27 is an exploded perspective view of the illuminated soft tissue retractor of FIG. 25.

Referring now to FIG. 27, waveguide assembly 2514 includes waveguide 2514W which is configured to provide optimal light conduction using total internal reflection (TIR) of the incident light introduced through light input 2522. Light input 2522 preferably has a round or cylindrical input transitioning into a square or rectangular section that is then coupled with the remainder of the waveguide. This transition zone creates dead zones in the square or rectangular portion of the light input 2522 where substantially no light is transmitted by TIR, and thus this portion of the waveguide may be coupled to the clip 2527 in order to minimize light loss due to contact between the waveguide and the clip. The use of TIR provides optimal efficiency and enables maximum light available and optimal direction of light 2523 at first output surface 2524 and second output surface 2526 (best seen in FIG. 30). Light from the first output surface 2524 preferably is directed distally and laterally from the waveguide to illuminate the surgical field as indicated by the arrows emanating from output surface 2524. Configured for use, waveguide 2514W may engage a clip such as clip 2527 for securing waveguide 2514W to the retractor blade connections such as clip socket 2521. The clip also allows a light input cable (not illustrated) to be releasably coupled with the light input 2522, and the clip also maintains an air gap around the cylindrical or round portion of the input 2522 to maximum light transmission efficiency. One or more shields such as light shield 2528 may also be included in waveguide assembly 2514. The shield may be coupled with the clip 2527 to prevent direct contact with the waveguide, and the shield helps to protect the waveguide from damaged caused by other instruments in the surgical field, as well as shielding the operator from glare which may shine back into his/her eyes. FIG. 30 illustrates a side view of the waveguide assembly 2514 seen in FIG. 37.

Referring now to FIG. 28, retractor assembly 2512 includes retractor body 2512A and retractor blade 2512B. Retractor blade 2512B is joined to retractor body 2512A at transition zone 2529 along interface 2513. Transition zone 2529 is configured to create drop angle 2530 between blade axis 2532 and retractor axis 2534. Drop angle 2530 is ideally between 5 and 35 degrees although any other suitable angle may be used. For thyroid surgery, drop angle 30 is about 15 degrees. Retractor blade length 2536 and retractor blade depth 2537 may adopt any suitable dimensions depending on the type of surgery anticipated. For thyroid surgery, blade length of 30 to 50 mm and blade depth of 25 to 60 mm are currently preferred. Of course, any dimensions may be used, and the exemplary ranges are not intended to be limiting. The inclination angle, angle 2538, of the retractor blade may adopt any suitable angle. For thyroid surgery, blade inclination angle 38 of 90 degrees is currently preferred.

Retractor blade 2512B has a proximal end 2540 which is secured to retractor body 2512A at interface 2513. Distal end 2542 of the retractor blade is configured for optimal utility in minimally invasive surgery. Retractor blade 2512B is generally narrow along depth 2537. In minimally invasive procedures it becomes important to enable tools to perform more than one function to save time and minimize movements of the surgical team. Distal end 2542 is configured with a trapezoidal tip 2543. In the procedure outlined below and in other procedures, an illuminated soft tissue retractor such as retractor 2510 may be used for blunt dissection as well as tissue retraction. Around delicate structures it is necessary to control the amount of force applied to the tissues being dissected and extending tip width 2544 expands the area of contact with the tissue being retracted and lessens the force per unit area applied to the tissue being retracted.

Retractor body 2512A may also include a source of illumination such as light 2546 and a portable source of energy such batteries 2547 to generate illumination. FIG. 29 illustrates a front perspective view of the retractor in FIG. 28.

Illuminated soft tissue retractor 2510 may be used to perform many different minimally invasive and open surgical procedures. The following example of a thyroid procedure is by way of example and is not limiting. In practice, the illuminated soft tissue retractor is used to perform a minimally invasive thyroidectomy as described below.

Figure 31:
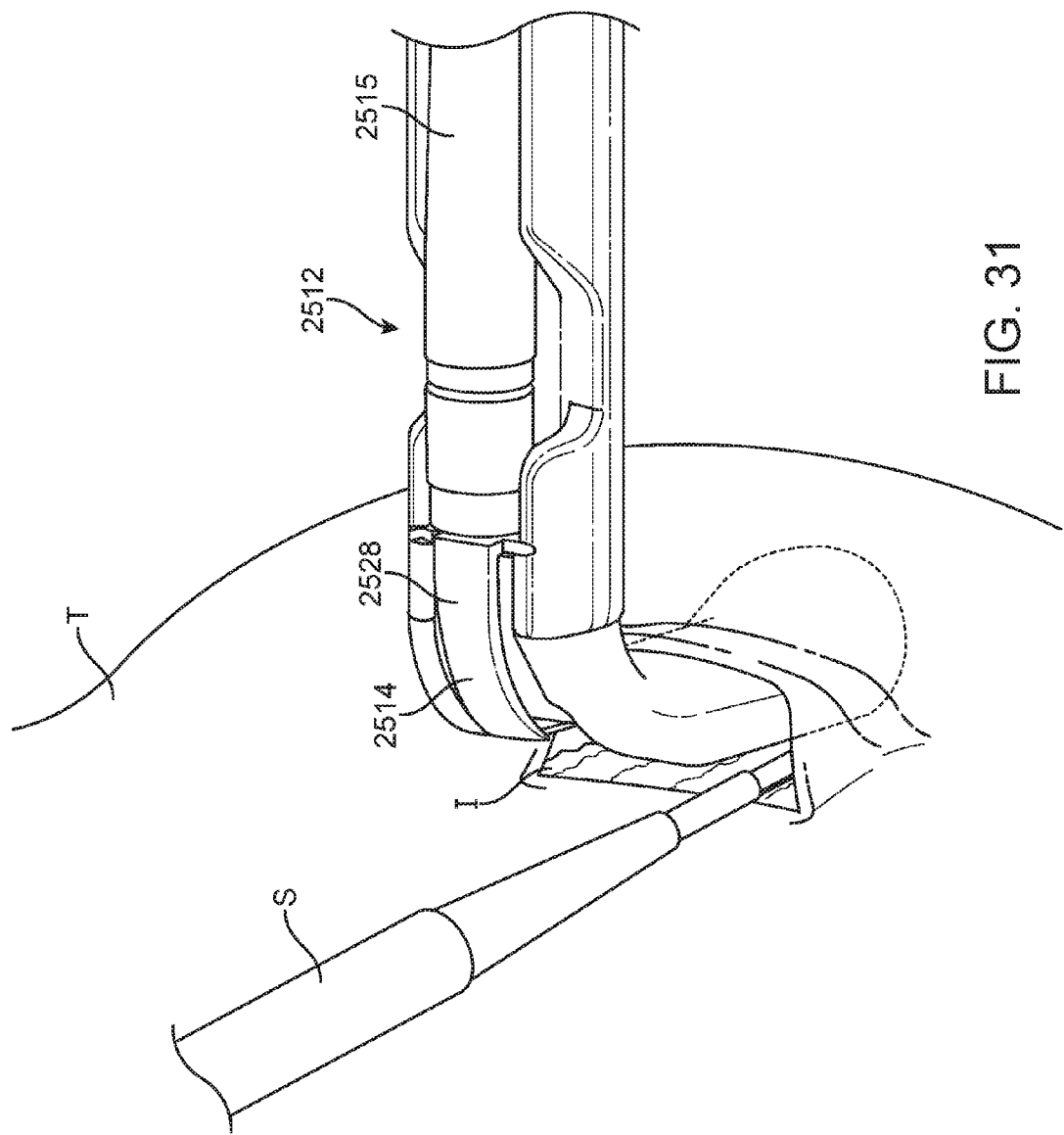
FIG. 31 illustrates use of the retractor in FIG. 25 to retract tissue.

FIG. 31 illustrates an illuminated retractor such as the embodiment described in FIGS. 25-30 above used in a thyroid procedure. The retractor 2512 is inserted into an incision I and is used to retract tissue T as described in greater detail below. This creates space for the surgeon to work and also allows surgical instruments S to be inserted into the surgical field such as an electrocautery device.

The patient is placed the supine position. Arms padded and tucked at the patient's side. A shoulder roll is placed to extend the neck and a foam donut placed to provide head support. A pillow is placed under the patient's knee and thigh high sequential hose applied. The head of the O.R. table is raised about 10 degrees and the foot lowered 10 degrees. The patient is then prepped and draped. Drapes are placed allowing access from the suprasternal notch to the chin and laterally to the margins of the sternocleidomastoid muscles.

After draping the cricoid cartilage is located by palpation. A skin marker is used to mark the incision no more than 1 cm below the cricoid cartilage and 3-4 cm long. If the incision is made lower than 1 cm the thyroid superior poles will be more difficult to dissect. The incision is made with a #15 blade through the skin and underlying platysma muscle. Double prong skin hooks are used to retract and lift the superior skin flap. A Kelly clamp is used to dissect the subplatysma plane. The inferior platysma plane is dissected in the same fashion. Grasping the proximal projection, the illuminated thyroid retractor is now used to retract the superior skin flap and illuminate the surgical site. The connective tissue between the strap muscles may be readily identified due to the improved illumination in the surgical site. Dissection is performed through the connective tissue with a Kelly clamp and electrocautery. The strap muscles are dissected both superiorly and inferiorly. Blunt dissection is utilized along with traction-counter traction to mobilize the strap muscles from the thyroid. A peanut sponge is used for blunt dissection. Similarly, the distal end of the illuminated soft-tissue retractor may be used for blunt dissection with improved visualization of adjacent structures owing to the illumination from the TIR waveguide. The blade of the illuminated thyroid retractor is placed under the strap muscles and the proximal projection is pulled laterally to provide the necessary counter traction.

The proximal projection provides a suitable location for application of counter traction without requiring the fatiguing tension that must often be applied to conventional retractors. At this point the overhead surgical lights do not provide adequate light. The illuminated soft tissue retractor provides the light necessary to continue the procedure in the surgical cavity. Careful blunt dissection is continued with counter traction to sweep the adherent connective tissue from the thyroid lobe. This dissection is done medially to far lateral thus mobilizing the thyroid from the adjacent structures including the carotid artery.

Dissection of the thyroid superior pole is now performed with a peanut sponge and counter traction with the illuminated thyroid retractor. Once the connective tissue is dissected the thyroid lobe is retracted inferiorly and medially. The space between the thyroid gland and cricothyroid muscles is identified. A Kelly clamp and peanut sponge is used to free the thyroid gland from the cricothyroid muscle. A Babcock clamp is placed on the gland to aid retraction and place tension on the superior pole. A Kelly clamp is used to identify and dissect the superior pole vessels. The superior parathyroid gland is also identified and dissected at this time. Counter traction and illumination is maintained with the illuminated thyroid retractor while the superior poles vessels are ligated.

Once the superior pole vessels are ligated the thyroid lobe is reflected medially and superiorly. The illuminated thyroid retractor is repositioned laterally to expose the lateral and inferior structures of the thyroid gland. Peanut sponges are used to dissect the remaining connective tissue. A Mosquito clamp is used to dissect and identify the inferior parathyroid gland, thyroid vessels, and the recurrent laryngeal nerve. Meticulous dissection is required to avoid injury to the recurrent laryngeal nerve. Remaining thyroid vessels are ligated. The connective tissue between the thyroid gland and trachea are dissected with a Mosquito clamp and peanut sponges. The dissection is continued medially to the Ligament of Berry. A Mosquito clamp is used to dissect and clamp the Ligament of Berry. Sharp dissection with a #15 blade and the remaining tissue is ligated. (The same technique is then performed in the same order on the opposite lobe). Once the thyroid resection is completed hemostasis is obtained. The strap muscles are re-approximated with 3-0 absorbable suture. The dermis is closed with 5-0 absorbable suture. A 5-0 subcutiular suture is used to close the skin. Any suitable op-site dressing is used to dress the wound.

Traction-countertraction is a technique used to provide tissue dissection and visualization of the recurrent laryngeal nerves and parathyroids in a minimally invasive thyroid surgery as described above. It is critical that these structures are preserved and not injured during the thyroidectomy surgery. The traction-countertraction technique is conventionally accomplished by using a USA or Army-Navy retractor to pull the strap muscles and carotid artery sheath away from the thyroid gland and at the same time retracting the thyroid gland in the opposite direction.

In order to see into the surgical site a headlight may be used. The headlight provides a unidirectional beam of light that is aimed by the surgeon. As the thyroid is dissected, the surgeon has to constantly change the position of his head, neck, and upper body in order to shine the light beam onto the different areas being dissected. Constantly having to change positions adds stress to the surgeon and in some instances he is unable to aim the light where it is needed. Therefore the illuminated retractors described herein may be used with the headlight or alone to illuminate the surgical field.

Illuminated soft tissue retractor 2510 has a longer and narrower retractor blade than conventional thyroid surgery retractors. The trapezoidal tip flares out providing increased surface area for retraction and dissection. The proximal projection easily engages the surgeon's hand lessening fatigue. The drop angle of 15 degrees allows the surgeon to retain his arm and shoulder in a more neutral position compared to conventional retractors. The inclusion of the TIR waveguide optimizes tissue visualization in deep surgical sites without the use of fatiguing headlamps.

In an alternate configuration, retractor assembly 2512 may be formed of separable elements. Retractor blade 2512B may be replaceable and may be separated from retractor body 2512A at interface 2513.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An illuminated surgical instrument for illuminating a surgical field, said instrument comprising:
   a handle having a proximal portion, a distal portion, and a longitudinal axis;
   a retractor blade releasably coupled to the distal portion of the handle, the retractor blade having a front surface and back surface, wherein the back surface is configured to engage and retract tissue and the front surface faces away from the back surface;
   an illumination element coupled to the distal portion of the handle, wherein the illumination element is configured to illuminate the surgical field and extends in a direction transverse to the longitudinal axis of the handle, and
   wherein the retractor blade is releasable from the handle while the illumination element remains coupled with the handle, and
   wherein the illumination element extends in substantially a same direction as the retractor blade, and
   wherein the illumination element is disposed adjacent the front surface of the retractor blade.

2. The instrument of claim 1, further comprising a cable coupled to a proximal portion of the illumination element, wherein the cable remains coupled to the illumination element while the retractor blade is released from the handle.

3. The instrument of claim 2, wherein the cable is disposed inside the handle.

4. The instrument of claim 1, wherein the illumination element comprises a waveguide.

5. The instrument of claim 1, wherein the retractor blade comprises a channel extending along a longitudinal axis of the retractor blade, and wherein the illumination element is disposed in the channel.

6. The instrument of claim 1, further comprising a quick release mechanism coupled to the handle, the quick release mechanism configured to release the retractor blade therefrom.

7. The instrument of claim 1, further comprising a suction tube coupled to the handle, the suction tube configured to remove smoke or noxious fumes from the surgical field.

8. The instrument of claim 1, wherein the retractor blade is uncoupled from the handle with movement of the retractor blade in a transverse direction relative to the longitudinal axis of the handle.

9. The instrument of claim 1, wherein the illumination element further comprises optical structures disposed thereon, the optical structures configured to extract and direct light from the illumination element toward the surgical field.

10. The instrument of claim 1, wherein the illumination element is releasable from the handle while the retractor blade remains coupled to the handle.

11. The instrument of claim 1, further comprising a collar surrounding at least a portion of the illumination element.

* * * * *